United States Patent
Robertson et al.

(10) Patent No.: US 11,590,295 B2
(45) Date of Patent: *Feb. 28, 2023

(54) SYSTEMS, APPARATUS, AND METHODS FOR FILTERING AIR FROM A FLUID LINE

(71) Applicant: 410 Medical, Inc., Durham, NC (US)

(72) Inventors: Galen C. Robertson, Apex, NC (US); Andrew W. Lane, Rolesville, NC (US); Savannah K. Carlsen, Durham, NC (US); Mark D. Piehl, Chapel Hill, NC (US); Robert W. Titkemeyer, Wimberley, TX (US); Stephen Latham, Sun Prairie, WI (US); Douglas Rodenkirch, Sun Prairie, WI (US); Jesse Darley, Madison, WI (US); Curtis Irwin, Madison, WI (US); Amrish Chourasia, Beloit, WI (US)

(73) Assignee: 410 Medical, Inc., Durham, NC (US)

(*) Notice: Subject to any disclaimer, the term of this patent is extended or adjusted under 35 U.S.C. 154(b) by 57 days.

This patent is subject to a terminal disclaimer.

(21) Appl. No.: 16/880,380

(22) Filed: May 21, 2020

(65) Prior Publication Data

US 2020/0384211 A1 Dec. 10, 2020

Related U.S. Application Data

(63) Continuation of application No. 16/459,016, filed on Jul. 1, 2019, now Pat. No. 10,661,029.
(Continued)

(51) Int. Cl.
*A61M 5/40* (2006.01)
*A61M 5/142* (2006.01)
(Continued)

(52) U.S. Cl.
CPC .............. *A61M 5/40* (2013.01); *A61J 1/10* (2013.01); *A61M 5/1424* (2013.01);
(Continued)

(58) Field of Classification Search
CPC ...... A61M 5/40; A61M 5/1411; A61M 39/24; A61M 2039/7536; A61M 5/1685; A61M 5/36
See application file for complete search history.

(56) References Cited

U.S. PATENT DOCUMENTS 2,879,784 A * 3/1959 Cutter .................... A61M 5/40
D24/129
3,207,372 A 9/1965 Evans
(Continued)

FOREIGN PATENT DOCUMENTS

DE 628167 3/1936
GB 2028975 A * 3/1980 ............ A61M 39/24
(Continued)

OTHER PUBLICATIONS

International Search Report and Written Opinion for International Application No. PCT/US2019/040166 dated Sep. 20, 2019, 9 pages.
(Continued)

*Primary Examiner* — Laura A Bouchelle
(74) *Attorney, Agent, or Firm* — Cooley LLP

(57) ABSTRACT

In some embodiments, a housing can define a reservoir. A lower cap can be coupled to the housing and define an outlet, and an upper cap can be coupled to the housing and can define an inlet. The upper cap can include an extending portion extending laterally a distance beyond an outermost extending portion of the lower cap relative to a central axis of the housing such that, when the lower cap and the extending portion of the upper cap contact a horizontal surface, the central axis of the housing is transverse to the
(Continued)

surface and a sealing member is configured to sealingly engage a sealing surface of a valve seat prior to a liquid fluid level within a reservoir decreasing below a minimum threshold fluid level.

27 Claims, 53 Drawing Sheets

Related U.S. Application Data

(60) Provisional application No. 62/692,390, filed on Jun. 29, 2018.

(51) Int. Cl.
  *A61J 1/10* (2006.01)
  *F16K 7/12* (2006.01)
  *B01D 19/00* (2006.01)
  *A61M 39/24* (2006.01)

(52) U.S. Cl.
  CPC ........ *A61M 5/14216* (2013.01); *A61M 39/24* (2013.01); *B01D 19/0031* (2013.01); *F16K 7/12* (2013.01); *A61M 2039/248* (2013.01); *A61M 2205/7536* (2013.01)

(56) References Cited

U.S. PATENT DOCUMENTS

| | | | |
|---|---|---|---|
| 3,465,784 A * | 9/1969 | Cofoid | A61M 5/40 137/430 |
| 3,954,623 A | 5/1976 | Hammer et al. | |
| 4,038,983 A | 8/1977 | Mittleman et al. | |
| 4,055,176 A * | 10/1977 | Lundquist | A61M 5/1411 604/254 |
| 4,143,659 A | 3/1979 | Biedermann | |
| 4,447,230 A | 5/1984 | Gula et al. | |
| 4,731,060 A | 3/1988 | Catalano | |
| 4,900,308 A | 2/1990 | Verkaart | |
| 4,959,053 A | 9/1990 | Jang | |
| 5,445,623 A | 8/1995 | Richmond | |
| 5,527,295 A | 6/1996 | Wing | |
| 5,569,208 A | 10/1996 | Woelpper et al. | |
| 5,779,674 A | 7/1998 | Ford | |
| 5,934,519 A | 8/1999 | Kim et al. | |
| 5,961,700 A * | 10/1999 | Oliver | B01D 19/0057 96/171 |
| 6,013,061 A | 1/2000 | Kelley | |
| 6,261,267 B1 * | 7/2001 | Chen | A61M 5/40 604/254 |
| 6,336,916 B1 | 1/2002 | Bormann et al. | |
| 8,328,770 B2 | 12/2012 | Wang | |
| 8,523,829 B2 | 9/2013 | Miner et al. | |
| 8,568,368 B2 | 10/2013 | Lampropoulos et al. | |
| 9,072,831 B2 | 7/2015 | Kelly et al. | |
| 10,016,564 B2 | 7/2018 | Piehl et al. | |
| 10,322,227 B2 | 6/2019 | Piehl et al. | |
| 10,391,257 B2 | 8/2019 | Piehl et al. | |
| 10,661,029 B2 * | 5/2020 | Robertson | A61M 5/40 |
| 2004/0243069 A1 | 12/2004 | Feith et al. | |
| 2005/0283123 A1 * | 12/2005 | Lyde | A61M 5/40 604/254 |
| 2006/0135939 A1 | 6/2006 | Brown | |
| 2009/0259199 A1 | 10/2009 | Lampropoulos et al. | |
| 2016/0166761 A1 | 6/2016 | Piehl et al. | |
| 2017/0281875 A1 | 10/2017 | Piehl et al. | |
| 2017/0319783 A1 | 11/2017 | Piehl et al. | |
| 2020/0001021 A1 | 1/2020 | Robertson et al. | |

FOREIGN PATENT DOCUMENTS

| | | |
|---|---|---|
| WO | WO 2014/145354 A1 | 9/2014 |
| WO | WO 2014/171761 A1 | 10/2014 |
| WO | WO 2016/099596 A1 | 6/2016 |
| WO | WO 2016/138018 A2 | 9/2016 |
| WO | WO 2020/006566 A1 | 1/2020 |

OTHER PUBLICATIONS

Extended European search report and European search opinion, dated Apr. 7, 2022, for EP 19826792.4 (8 total pages).

* cited by examiner

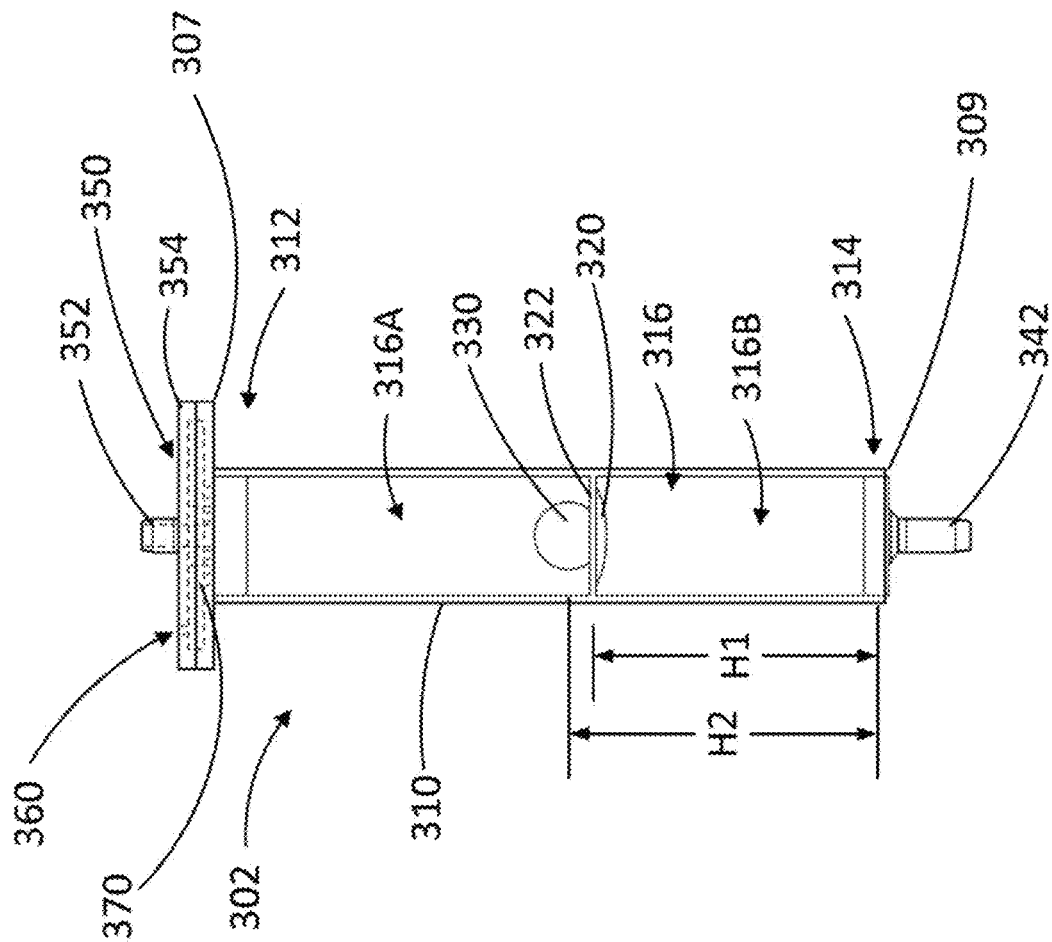

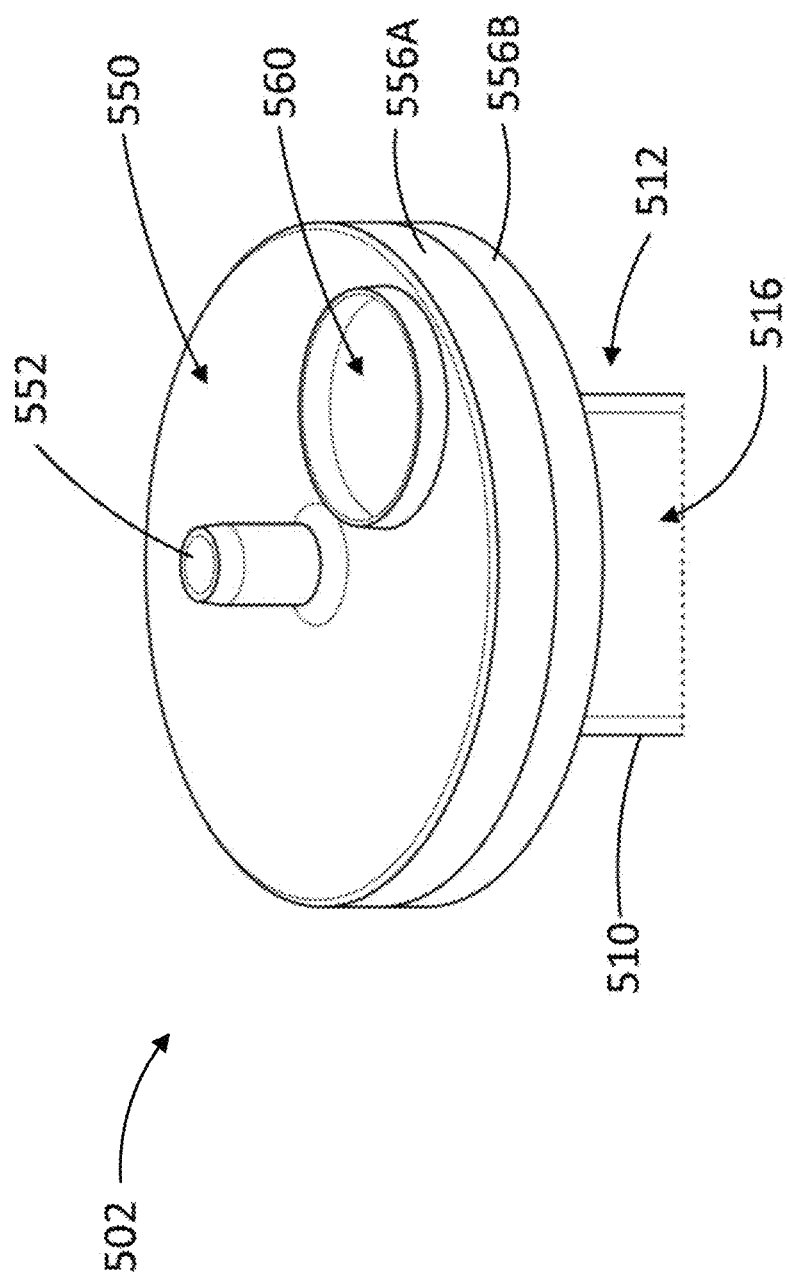

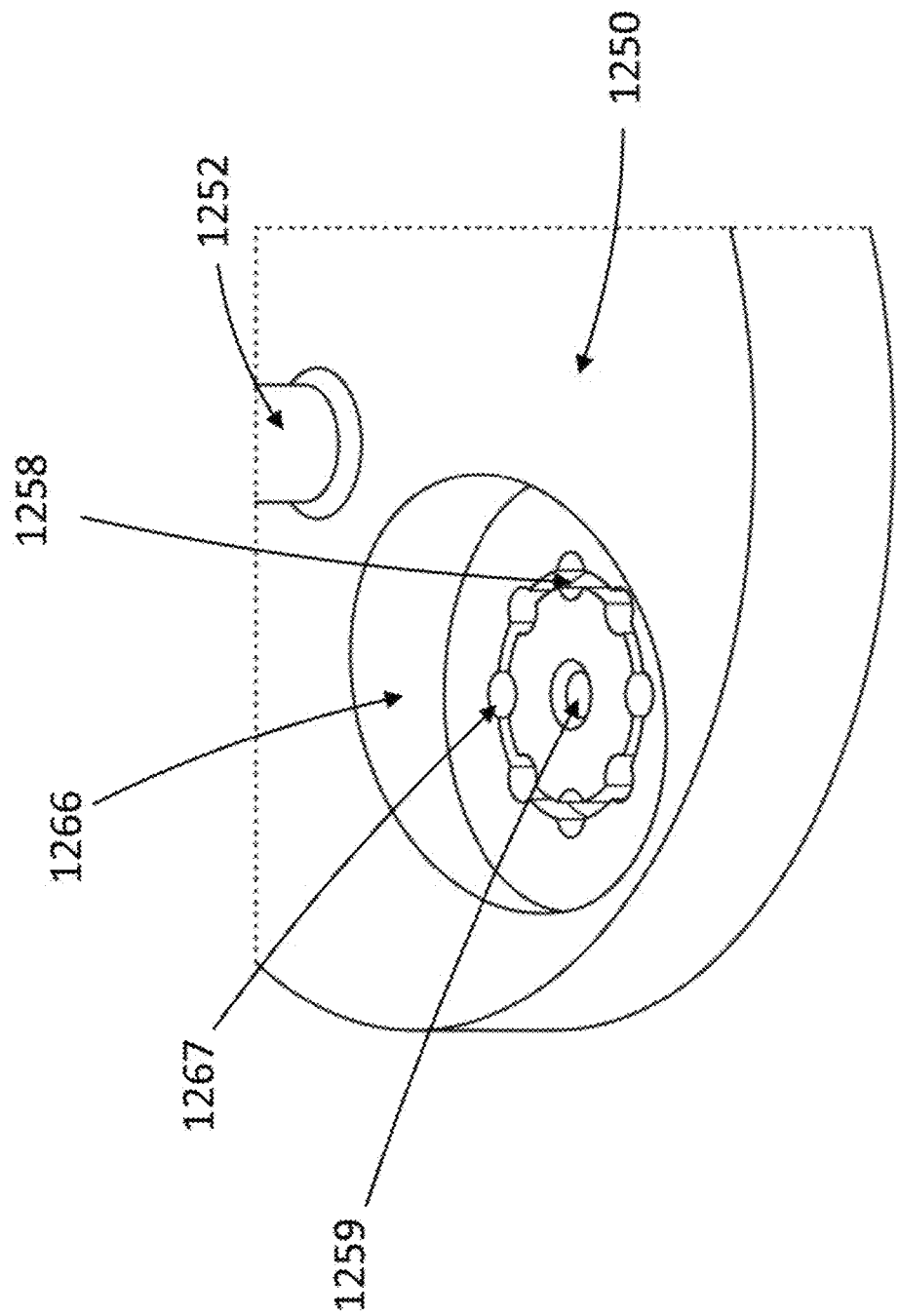

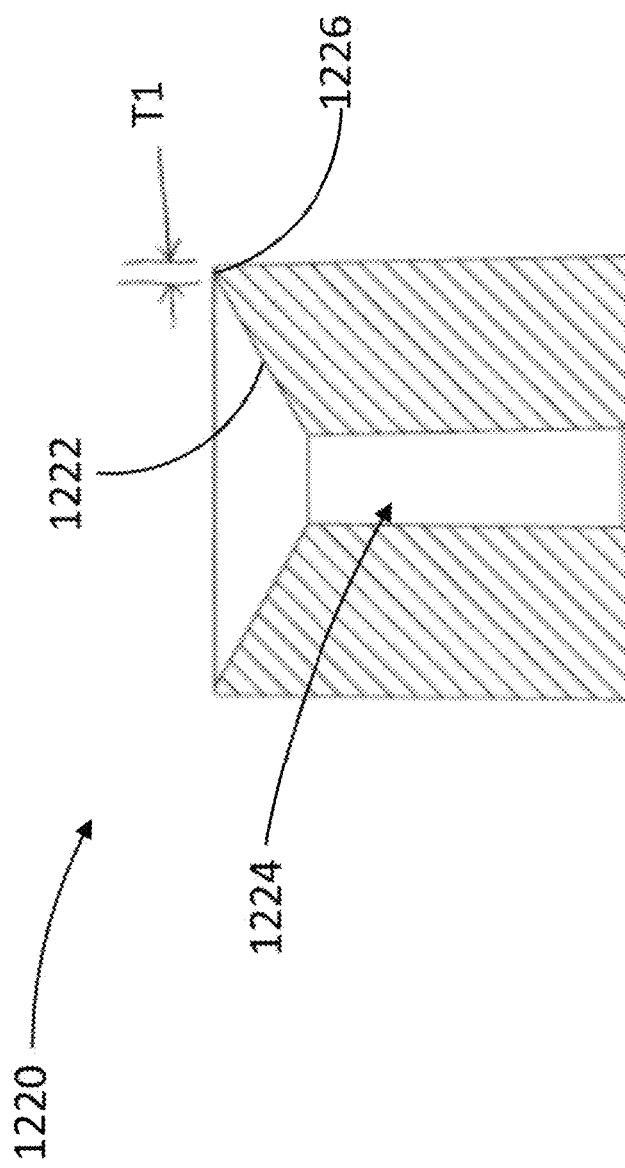

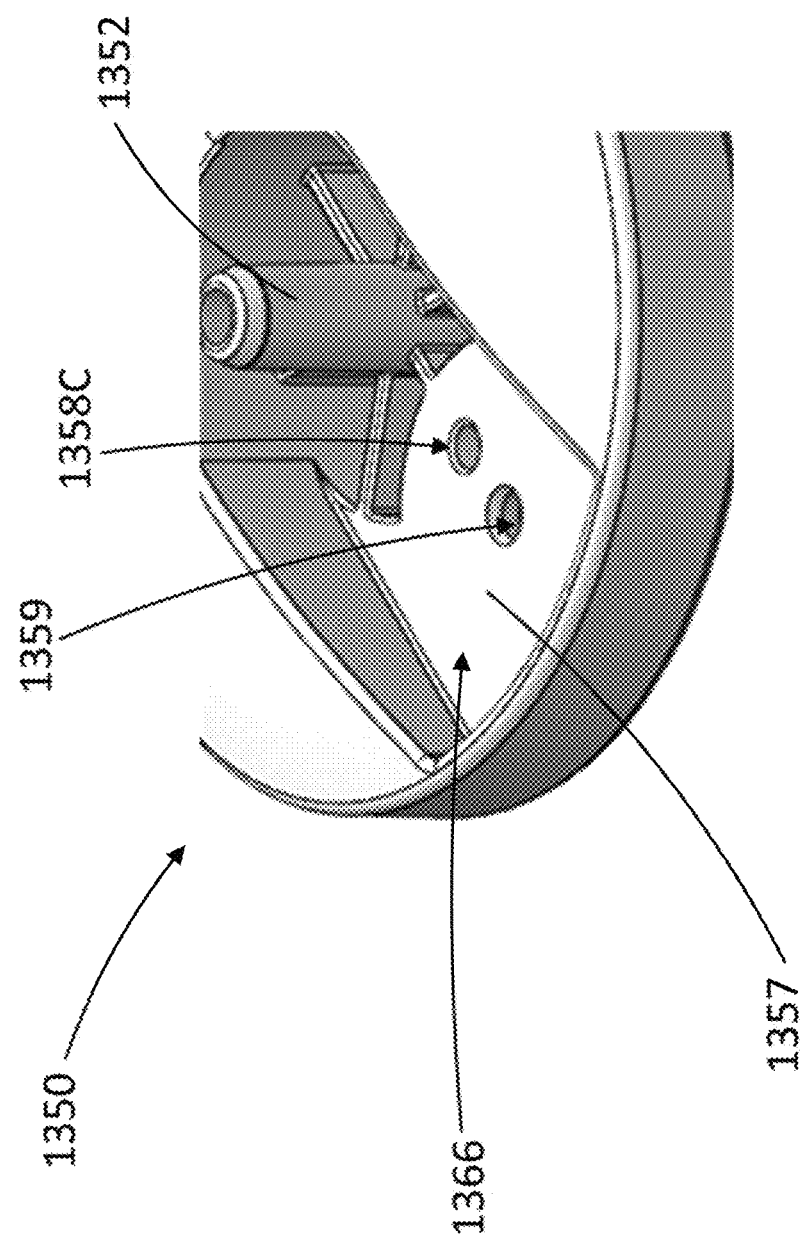

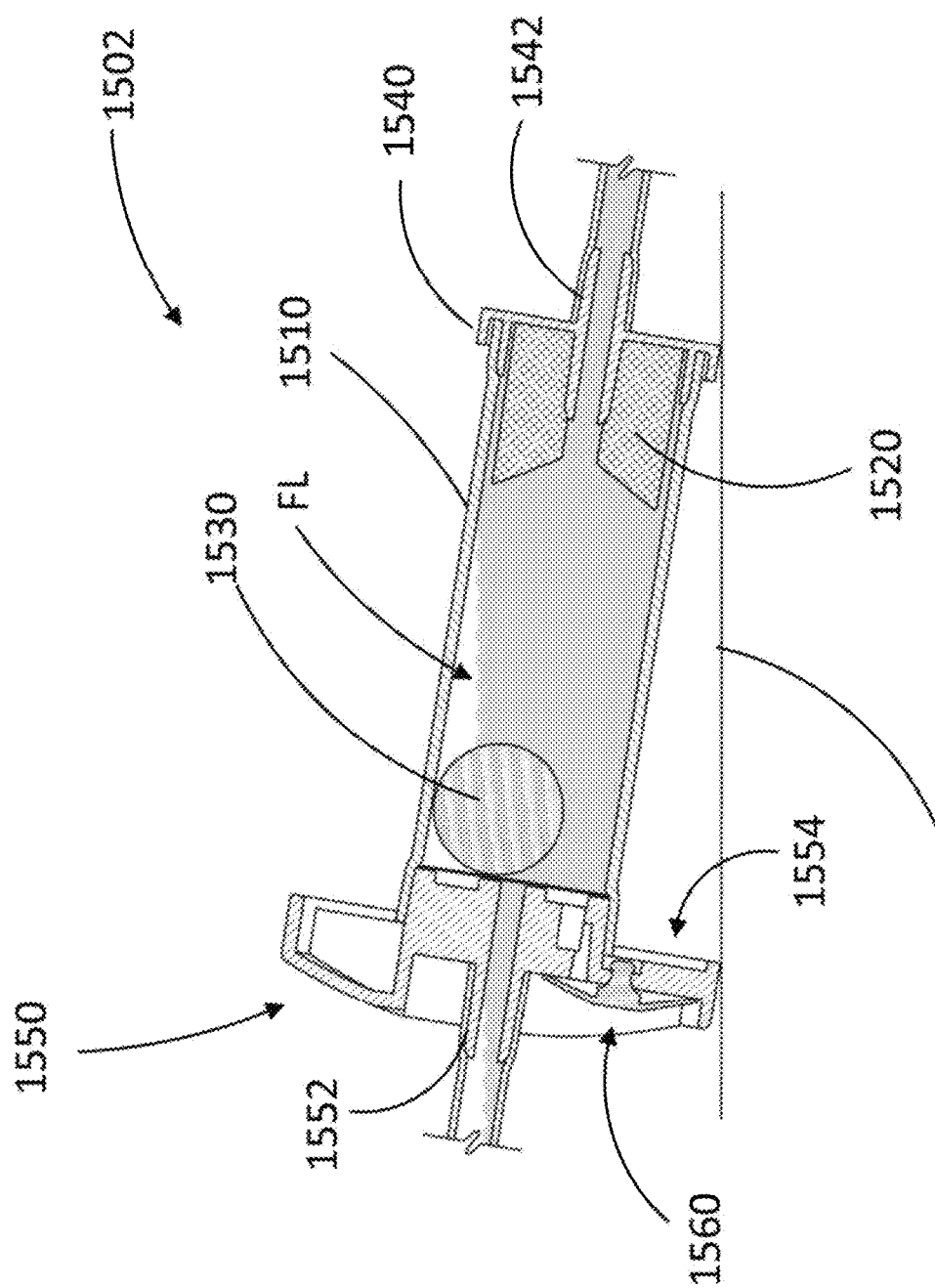

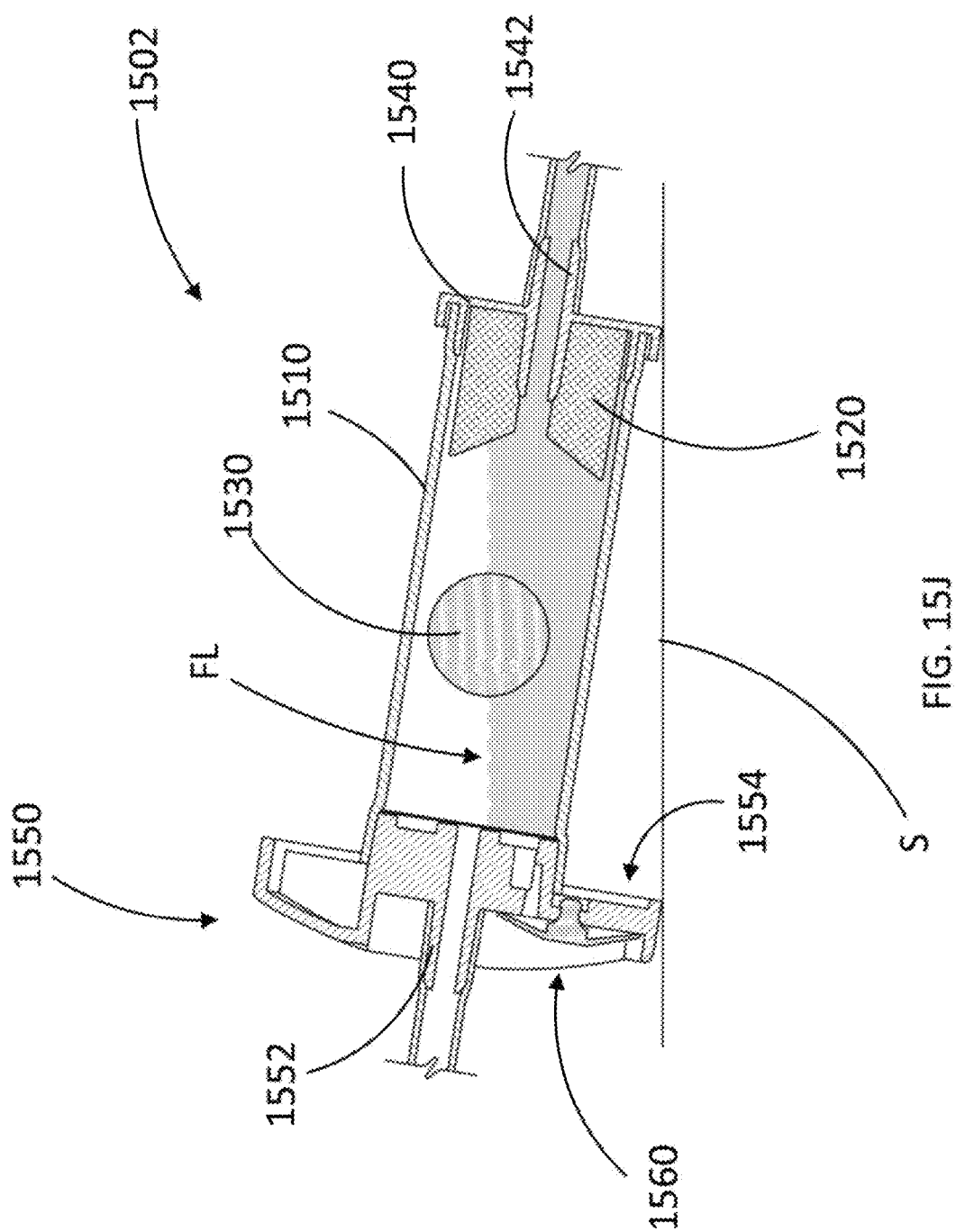

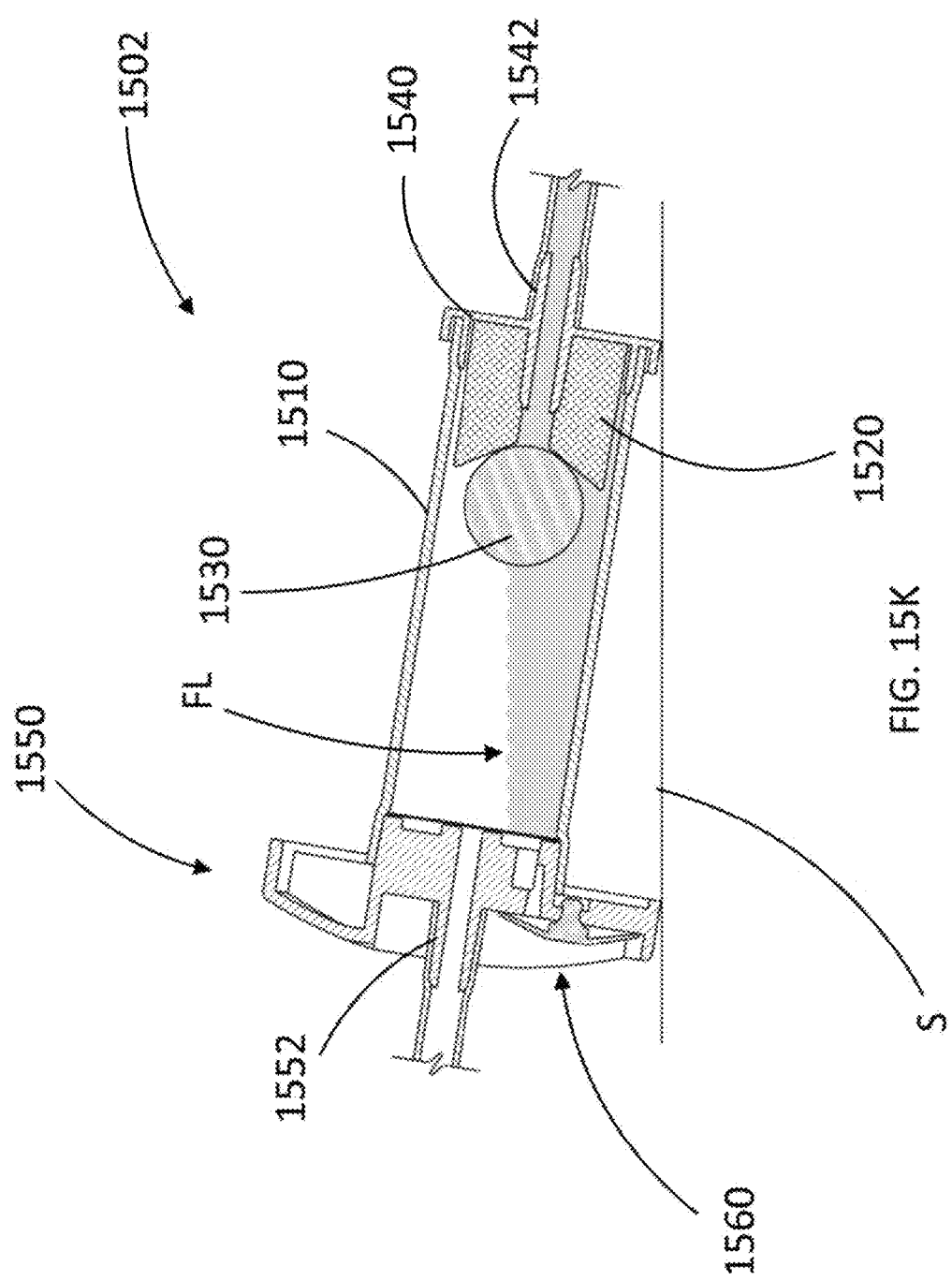

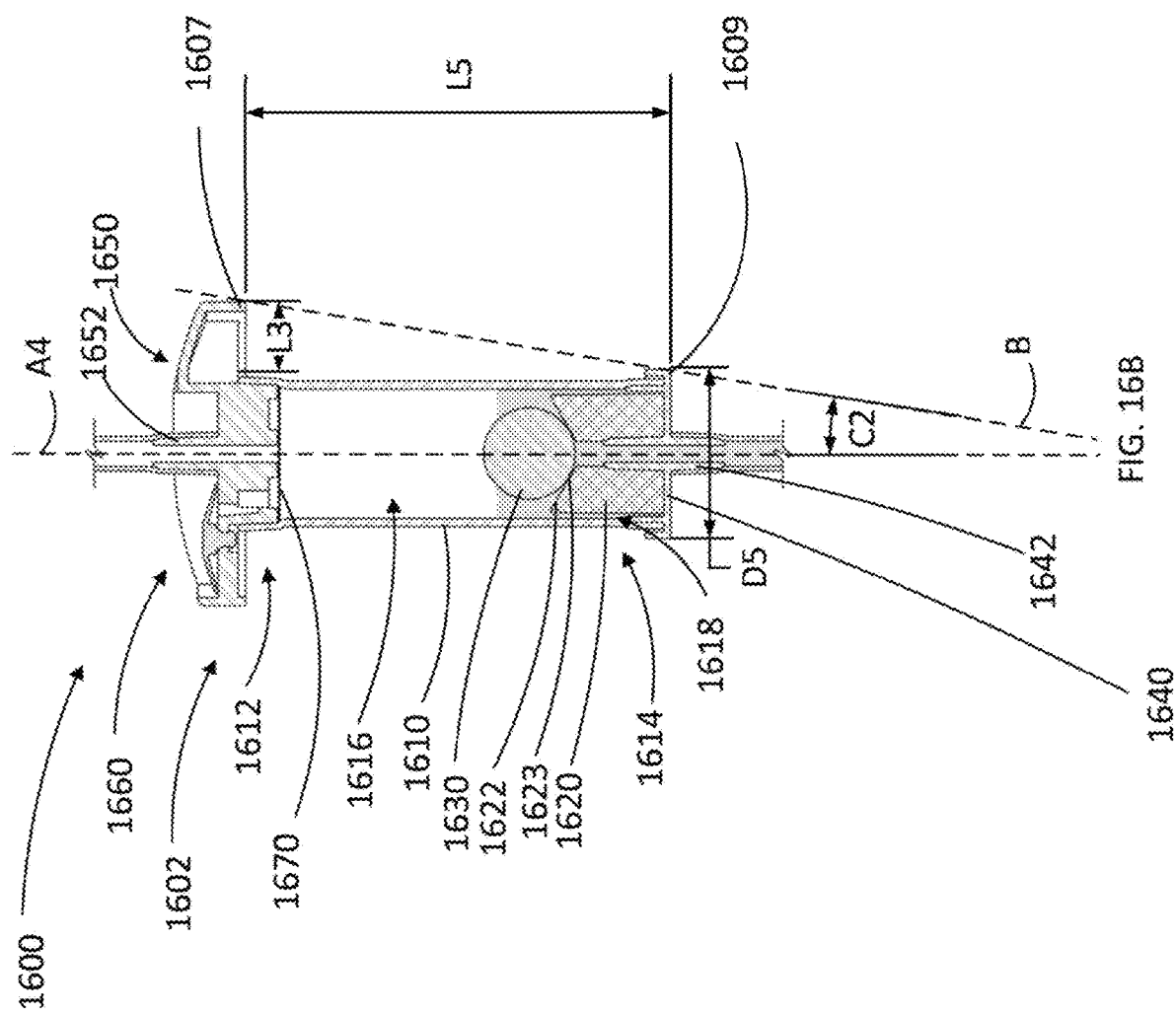

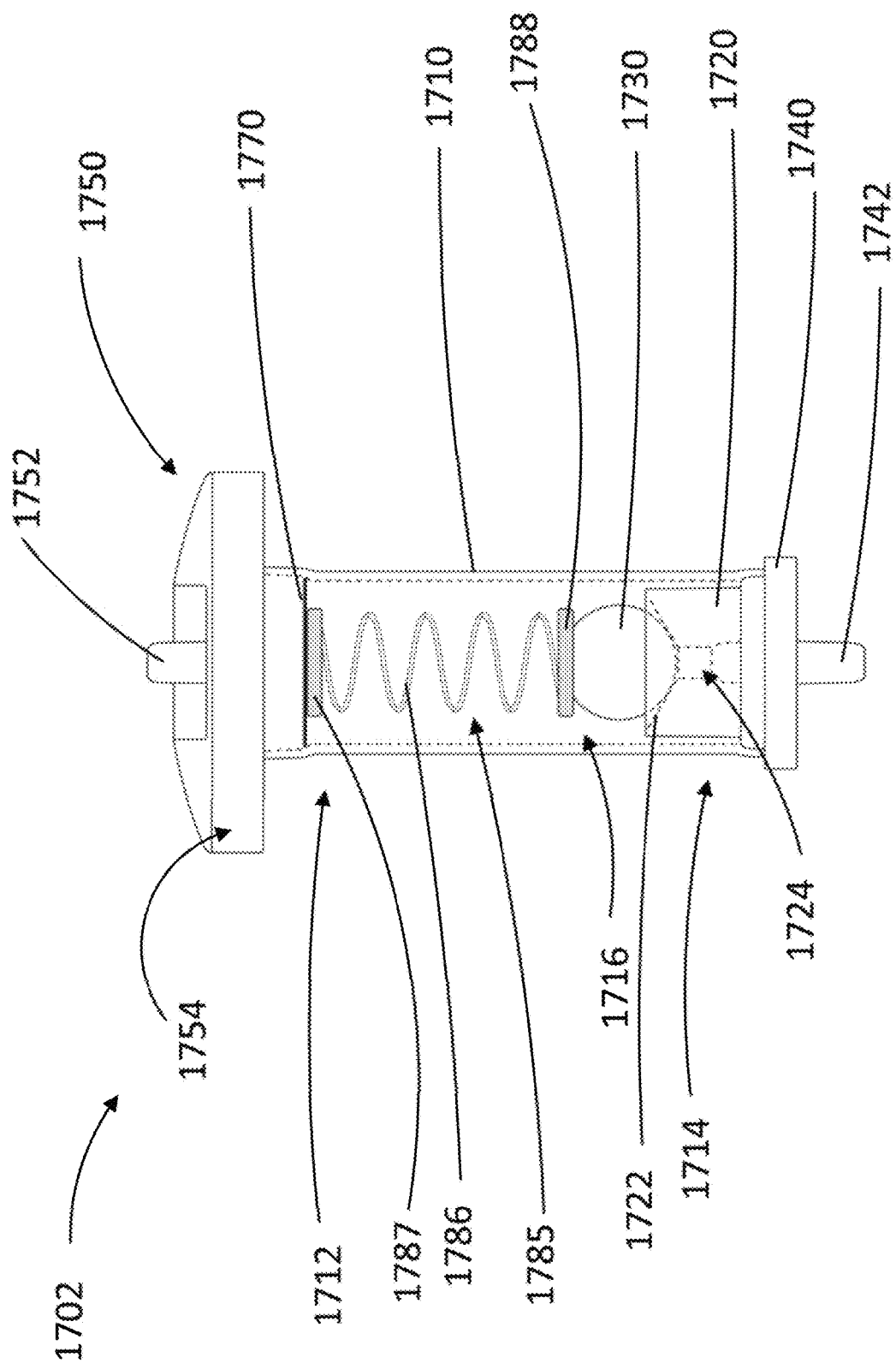

SYSTEMS, APPARATUS, AND METHODS FOR FILTERING AIR FROM A FLUID LINE

CROSS-REFERENCE TO RELATED APPLICATIONS

This application is a continuation of U.S. application Ser. No. 16/459,016, filed Jul. 1, 2019, now U.S. Pat. No. 10,661,029, entitled "Systems, Apparatus, and Methods for Filtering Air from a Fluid Line," which claims priority to and the benefit of U.S. Provisional Application No. 62/692,390, filed Jun. 29, 2018, entitled "Systems, Apparatus, and Methods for Filtering Air from a Fluid Line," the entire contents of each of which are incorporated by reference herein for all purposes.

BACKGROUND

Embodiments described herein relate to systems, apparatus, and methods for filtering air from a fluid line.

Rapid fluid administration can be essential to the survival of patients suffering from shock, which is a life-threatening condition that can result from a variety of causes including bacterial sepsis, hemorrhage, trauma, severe dehydration, and anaphylaxis. The American Heart Association's Pediatric Advanced Life Support (PALS) guidelines, the American College of Critical Care Medicine, and the Surviving Sepsis Campaign guidelines for adults recommend rapid fluid resuscitation as a key element of the initial therapeutic response to shock. For example, PALS recommends the infusion of 20 milliliters of fluid per kilogram of body weight during the first five minutes of the initial therapeutic response and up to 60 milliliters per kilogram of body weight during the first fifteen minutes of the initial therapeutic response. Additionally, blood and blood products may also need to be infused rapidly for trauma victims and other patients who are hemorrhaging.

Healthcare providers use various methods and systems to deliver fluid or medicine rapidly from a reservoir, including gravity-based systems, infusion pumps, pressure bags applied to the fluid reservoir, hand-operated syringes, and/or mechanical rapid-infusion systems. Often, fluid is delivered to a patient from pre-filled sterile fluid bags. The fluid bags are frequently pre-filled with sterile saline and approximately 80 mL of air to improve visualization of the fluid volume remaining in the bag. Providers can be trained to remove the air from the fluid bag prior to infusing rapidly (e.g., with a rapid infuser or pressure bag). If the air is not removed or the removal is performed improperly, however, air may be infused into the patient's circulatory system, resulting in an air embolism. While automatic shut off systems can be used to shut off the flow of air before a significant volume of air enters the patient and fluid bag changing systems can allow for fluid bags to be changed while preventing air from passing into the patient, known automatic shut off systems and fluid bag changing systems are complex, expensive, and can lack effectiveness with respect to the sealing mechanism in real-world conditions.

Furthermore, some patients require the infusion of multiple fluid bags of intravenous (IV) fluids. When a first fluid bag is empty, the empty fluid bag must be removed and replaced by a second fluid bag. The second fluid bag may include air (e.g., 80 mL of air) that requires removal. If IV tubing used to couple the fluid bags to the patient is already primed with fluid, the IV tubing must be drained out onto the floor or into another receptacle while the 80 mL of air is pushed out from the fluid bag. Clinicians sometimes skip this step due to the extra work involved, risking infusion of air into the patient. Alternately, some clinicians will spike the second fluid bag, remove the spike, manually squeeze the air from the fluid bag, and reconnect the spike time. This method, referred to as "burping the bag," can be effective in removing the air from the second fluid bag, but can create an infection risk for the patient.

Additionally, many infusion systems rely on gravity to pull fluid into the patient. For example, a fluid bag can be elevated above a patient and hung on an IV pole to create positive gauge pressure. These systems, however, typically require both the fluid bag and any drip chambers or air chambers fluidically coupled to the fluid bag to be disposed in a vertical orientation properly to prevent air from flowing to the patient. In some emergency situations, such as when a patient must be moved between locations (e.g., within a hospital or during transport by ambulance or helicopter), a fluid bag and/or drip or air chamber may tip over (e.g., if there is no IV pole available), allowing air to flow from the fluid bag to the patient and causing an air embolism.

Therefore, there is a need for systems, apparatus, and methods that can improve the ease by which air can be removed from a fluid bag and infusion line and can prevent air from traveling to the patient, even if the system or a portion of the system is inadvertently tipped over or placed on its side. Furthermore, there is a need for systems, apparatus, and methods that allow air to be purged from a fluid bag without having to disconnect or reconnect any tubing during the purging process.

BACKGROUND

In some embodiments, an apparatus includes a housing, a lower cap, a valve seat, a sealing member, and an upper cap. The housing can define a reservoir and have a first end, a second end, and a central axis. The lower cap can be coupled to the second end of the housing and can define an outlet. The valve seat can have a first end, a second end, and a sealing surface. The valve seat can define a through-hole from the sealing surface to the second end. The valve seat can be disposed within the housing with the second end of the valve seat coupled to the lower cap such that the outlet of the lower cap is in fluid communication with the reservoir via the through-hole of the valve seat. The sealing member can be configured to float at a liquid fluid level within the reservoir and to seal with the sealing surface of the valve seat prior to the liquid fluid level within the reservoir decreasing below a minimum threshold fluid level. The upper cap can define an inlet and can be coupled to the first end of the housing. The upper cap can include an extending portion extending laterally a distance beyond an outermost extending portion of the lower cap relative to the central axis of the housing such that, when the lower cap and the extending portion of the upper cap contact a horizontal surface, the central axis of the housing is transverse to the surface and the sealing member is configured to sealingly engage the sealing surface of the valve seat prior to the liquid fluid level within the reservoir decreasing below a minimum threshold fluid level.

BRIEF DESCRIPTION OF THE DRAWINGS

FIG. 3A is a side view of an assembly in a vertical orientation, according to an embodiment.

FIG. 5A is a perspective view of a portion of an assembly, according to an embodiment.

FIG. 12D is a perspective view of a portion of the assembly of FIG. 12A.

FIG. 12G is a cross-sectional view of a valve seat of the assembly of FIG. 12A.

FIG. 13E is a perspective view of portion of the assembly of FIG. 13A.

FIGS. 15A-15L are cross-sectional illustrations of a portion of a system, according to an embodiment, during various stages of use.

FIGS. 16A and 16B are cross-sectional illustrations of a portion of a system, according to an embodiment, in a sealed configuration.

FIG. 17 is a side view of an assembly including a spring assembly, according to an embodiment.

DETAILED DESCRIPTION

Figure 1:
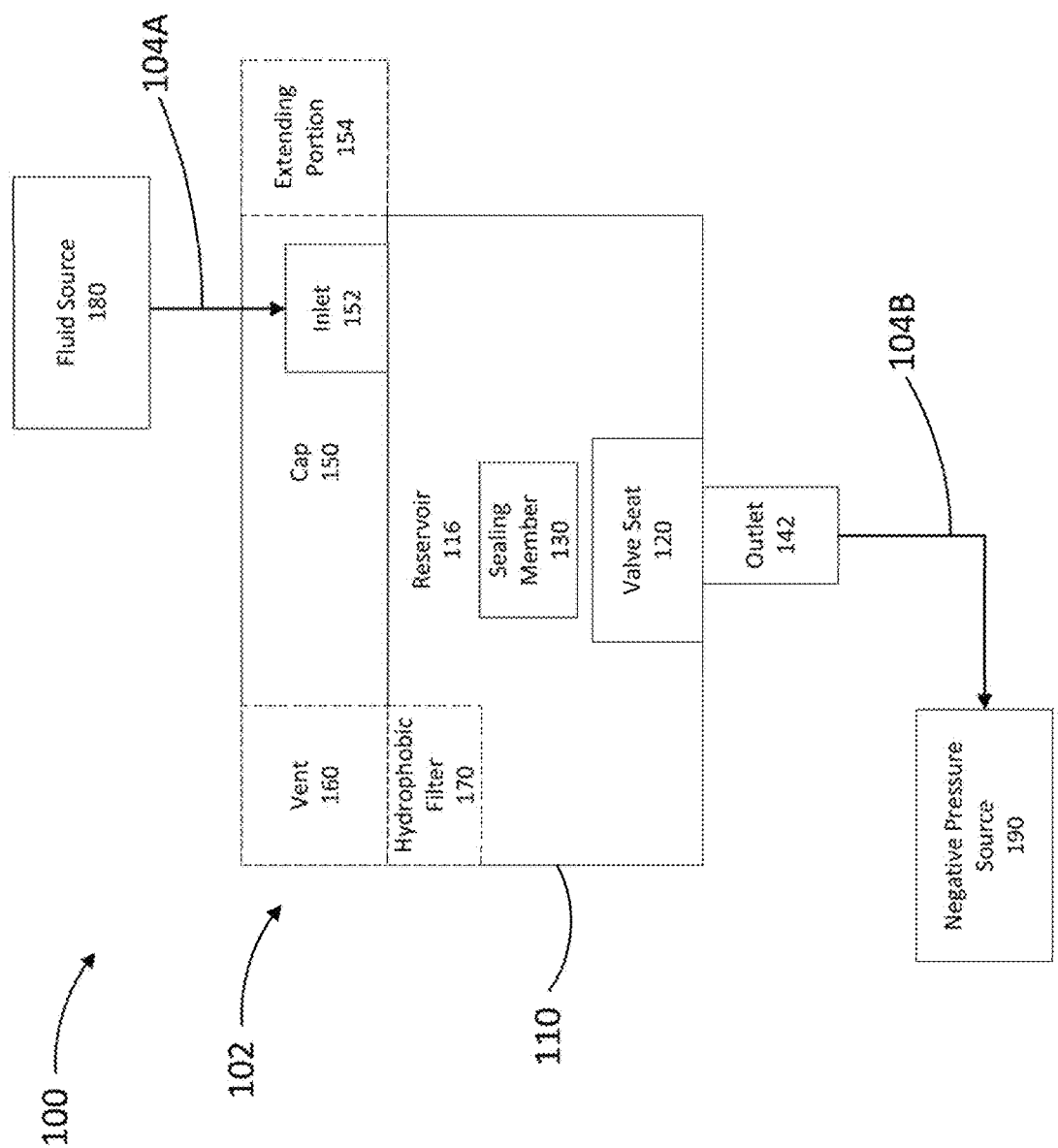
FIG. 1 is a schematic illustration of a system, according to an embodiment.

In some embodiments, an apparatus includes a housing, a lower cap, a valve seat, a sealing member, and an upper cap. The housing can define a reservoir and have a first end, a second end, and a central axis. The lower cap can be coupled to the second end of the housing and can define an outlet. The valve seat can have a first end, a second end, and a sealing surface. The valve seat can define a through-hole from the sealing surface to the second end. The valve seat can be disposed within the housing with the second end of the valve seat coupled to the lower cap such that the outlet of the lower cap is in fluid communication with the reservoir via the through-hole of the valve seat. The sealing member can be configured to float at a liquid fluid level within the reservoir and to seal with the sealing surface of the valve seat prior to the liquid fluid level within the reservoir decreasing below a minimum threshold fluid level. The upper cap can define an inlet and can be coupled to the first end of the housing. The upper cap can include an extending portion extending laterally a distance beyond an outermost extending portion of the lower cap relative to the central axis of the housing such that, when the lower cap and the extending portion of the upper cap contact a horizontal surface, the central axis of the housing is transverse to the surface and the sealing member is configured to sealingly engage the sealing surface of the valve seat prior to the liquid fluid level within the reservoir decreasing below a minimum threshold fluid level.

In some embodiments, an apparatus includes a housing, an upper cap, a lower cap, a deformable valve seat, and a sealing member. The housing can include a cylindrical sidewall, the cylindrical sidewall including an inner surface defining a reservoir and an outer surface. The housing can have a first end and a second end. The cylindrical sidewall can be configured to be deformed between an undeformed and a deformed configuration. The upper cap can define an inlet and the cap can be coupled to the first end of the housing. The lower cap can define an outlet and be coupled to the second end of the housing. The deformable valve seat can have a first end, a second end, and a sealing surface. The valve seat can define a through-hole from the first end to the second end, the through-hole having a central axis. The second end can be coupled to the lower cap such that the through-hole is in fluid communication with the outlet of the lower cap. The sealing member can be configured to float at a liquid fluid level within the reservoir and to seal with the sealing surface of the valve seat prior to the liquid fluid level within the reservoir decreasing below a minimum threshold fluid level. The sealing member can be configured to transition from a sealed configuration in which the seal is engaged with the sealing surface to an unsealed configuration in which the sealing member floats at the liquid fluid level when the liquid fluid level is above the minimum threshold fluid level and the cylindrical sidewall is flexed to the deformed configuration such that the valve seat is deformed and a seal between the sealing member and the sealing surface is disrupted.

In some embodiments, a method includes applying a negative pressure to a reservoir via a negative pressure source such that fluid is drawn from the reservoir through a through-hole of a valve seat until the fluid level decreases such that a sealing member seals with the valve seat such that the reservoir is fluidically isolated from the through-hole. The negative pressure source can be fluidically coupled to the through-hole and to a patient's vasculature. An inlet of the reservoir can be coupled to an inlet of the reservoir to a fluid source such that fluid flows from the fluid source into the reservoir. The sealing member can remain sealed with the valve seat as the fluid level increases due to the negative pressure. A wall of the housing defining the reservoir can be deformed such that the wall of the housing deforms the valve seat and the sealing member is released from the valve seat such that the sealing member can float to the fluid level.

In some embodiments, a method includes coupling an inlet of an assembly to a fluid source such that fluid can flow from the fluid source and into a reservoir defined by the assembly. The assembly can be disposed on a surface such that a portion of an upper cap of the assembly and a portion of a lower cap of the assembly contacts the surface and maintains a centerline of a through-hole of a valve seat of the assembly transverse relative to the horizontal. A negative pressure can be applied to an outlet of the reservoir such that fluid can be drawn through the through-hole of the valve seat and out of an outlet of the reservoir until a fluid level within the reservoir decreases such that a sealing member seals with the valve seat and the reservoir is fluidically isolated from the through-hole.

FIG. 1 is a schematic illustration of a system 100. The system 100 includes an assembly 102, a fluid source 180, and a negative pressure source 190. The assembly 102 includes a housing 110, a cap 150, and an outlet 142. The housing 110 can define a reservoir 116 and the cap 150 can define an inlet 152. The cap 150 can be sealingly coupled to the housing 110 and the inlet 152 can be fluidically coupled to the fluid source 180 (e.g., via tubing 104A) such that fluid can be introduced into the reservoir 116 via the inlet 152. The outlet 142 can be coupled to the housing 110 and fluidically coupled to the negative pressure source 190 (e.g., via tubing 104B) such that fluid can flow toward the negative pressure source 190 from the reservoir 116 via a lumen defined by the outlet 142. The assembly 102 can include a valve seat 120 and a sealing member 130. The valve seat 120 can define a through-hole and be disposed relative to the outlet 142 such that fluid can flow from the reservoir 116 to the outlet 142 via the through-hole of the valve seat 120. The valve seat 120 and the sealing member 130 can be configured to allow liquid fluid to flow from the reservoir 116 into the outlet 142 when the liquid fluid level or volume within the reservoir 116 is above a predetermined threshold level or volume, and to prevent the flow of fluid through the outlet 142 when the liquid fluid level or volume within the reservoir 116 is at or below a predetermined threshold level or volume, thus preventing air from flowing into the outlet 142. For example, the sealing member 130 can be configured to sealingly engage with a sealing surface of the valve seat 120 such that the sealing member 130 obstructs the through-hole. In some embodiments, the cap 150 can define a vent 160 such that fluid, such as air, can exit the reservoir 116 via the vent 160. In some embodiments, the system 100 can also include a hydrophobic filter 170 disposed between the reservoir 116 and the vent 160 such that liquid fluid that has been introduced into the reservoir 116 via the inlet 152 can be prevented from exiting the reservoir 116 via the vent 160, while gas (e.g., air) is permitted to exit the reservoir 116. In some embodiments, the cap 150 can also include an extending portion 154 such that at least a portion of the cap 150 extends laterally beyond a sidewall of the housing 110 relative to a centerline of the housing 110.

The housing 110 can have any suitable shape configured to define a fluid reservoir (e.g., reservoir 116). For example, the housing 110 can have a cylindrical shape. In some embodiments, the housing 110 can include a cylindrical sidewall formed such that the housing 110 defines a first open end and a second open end opposite the first open end (i.e., the housing 110 is shaped as a tube). In some embodiments, the system 100 can include a lower cap (not shown) coupled to the first end of the tube, the lower cap including the outlet 142. In some embodiments, the housing 110 and the outlet 142 can be monolithically formed. For example, rather than having an open end on the outlet side of the housing 110, the housing 110 can include a bottom surface and the outlet 142 can extend from the bottom surface.

In some embodiments, the housing 110 can have one or more sidewalls that are flexible such that a user can deform the housing 110 by squeezing the sidewalls. In some embodiments, the valve seat 120 can also be deformable, and the housing 110 can include deformable portions disposed adjacent to and/or surrounding the valve seat 120 such that the valve seat 120 can be deformed via squeezing the deformable portions. In some embodiments, the portion of the housing 110 that is deformable can be at least the portion of the housing 110 below a center of the sealing member 130 when the sealing member 130 is in a sealed configuration relative to the valve seat 120. For example, the deformable portion of the housing 110 can be at least as long as the width of a typical user finger (e.g., at least 0.5 inches). In some embodiments, the housing 110 can be made of any suitable material, such as polyvinyl chloride (PVC). In some embodiments, the housing 110 can have a durometer of, for example, between about 60A and about 80A.

As described above, the valve seat 120 can define a through-hole and be disposed relative to the outlet 142 such that fluid can flow from the reservoir 116 to the outlet 142 via the through-hole of the valve seat 120. In some embodiments, the valve seat 120 can be coupled to a lower cap or a bottom surface of the housing 110 such that the through-hole of the valve seat 120 is aligned with the outlet 142 (e.g., the through-hole of the valve seat 120 and the lumen of the outlet 142 are coaxial). In some embodiments, the central axis of the through-hole of the valve seat 120 and the central axis of the housing 110 can be collinear. The valve seat 120 can define a sealing surface configured to seal with the sealing member 130. The sealing surface can be, for example, conically-shaped. The sealing surface can be formed as a chamfer between an upper surface of the valve seat 120 and the surface of the valve seat 120 defining the through-hole. In some embodiments, the sealing surface can extend from an outer surface of the valve seat 120 to the inner surface of the through-hole such that the entire upper surface of the valve seat 120 is continuous and smooth. In some embodiments, the sealing surface can be disposed at an angle of, for example, 30° degrees relative to a central axis of the through-hole of the valve seat 120. In some embodiments, the valve seat 120 can include an upper surface surrounding the sealing surface (e.g., a conically-shaped sealing surface). The upper surface can be disposed, for example, in a plane lying perpendicular to the central axis of the through-hole of the valve seat 120. The upper surface can have a thickness sufficiently small such that the sealing member 130 does not contact and/or catch on the upper surface as the sealing member 130 approaches the sealing surface, regardless of whether the assembly 102 is disposed in an upright orientation (e.g., vertically oriented) or is disposed on a surface (e.g., a horizontal surface) such that the assembly 102 is resting on the surface. In some embodiments, the height of the valve seat 120 and/or distance from the bottom of the housing 110 to the top of the valve seat 120 can be sufficient such that, when the sealing member 130 is sealingly engaged with the sealing surface of the valve seat 120 and the liquid fluid level within the reservoir 116 is above a minimum threshold fluid level, the valve seat 120 can be deformed such that the sealing member 130 separates from the valve seat 120 via a squeezing force applied to the housing 110 below, for example, the top of the valve seat 120 or the center of the sealing member 130. For example, in some embodiments, the valve seat 120 can have a height of between about 1.5 cm and about 3 cm. In some embodiments, the valve seat 120 can have a height of more than 3 cm. In some embodiments, the valve seat 120 can have an outer diameter that is substantially similar to the inner diameter of the housing 110 such that the outer surface of the valve seat 120 can contact the inner surface of the housing 110. In some embodiments, the valve seat 120 can have an outer diameter that is smaller than an inner diameter of the housing 110 such that a circumferential gap is defined between the outer surface of the valve seat 120 and the inner surface of the housing 110.

The sealing member 130 can be any suitable shape and size configured to seal with the valve seat 120 when the liquid fluid level or volume in the reservoir 116 drops below a threshold level or volume. For example, the sealing member 130 can be spherically-shaped. In some embodiments, the sealing member 130 can define a hollow interior. The dimensions and characteristics of the sealing member 130 (e.g., the outer diameter, diameter of the hollow interior, material, density) can be selected such that the sealing member 130 is sufficiently buoyant to float within the reservoir 116 when the liquid fluid level (also referred to herein as the "fluid level") within the reservoir 116 is above a minimum threshold and to seal against the sealing surface of the valve seat 120 such that the reservoir 116 is fluidically isolated from the outlet 142 when the fluid level within the reservoir 116 reaches the minimum threshold. In some embodiments, the sealing member 130 can seal with the valve seat 120 regardless of whether the assembly 102 is vertically-oriented (e.g., hanging from an IV pole with its axis approximately parallel to the direction of gravity) or at a range of angles between vertical and an angle relative to horizontal, e.g., when the assembly 102 is disposed on a surface such that the housing 110 is oriented at an angle relative to the surface such that the upper end of the housing 110 (e.g., the inlet end) is vertically higher than the lower end of the housing 110 (e.g., the outlet end). In some embodiments, the sealing member 130 can be configured to remain sealed with the valve seat 120 after liquid fluid has been added to the reservoir 116 until the sealing member 130 has been manually dislodged from the valve seat 120 (e.g., via squeezing the housing 110 and the valve seat 120). In some embodiments, the sealing member 130 can remain sealed with the valve seat 120 prior to manual dislodgement due to the strength of the seal between the sealing member 130 and the valve seat 120 and/or negative pressure applied to the sealing member 130 by the negative pressure source 190 via the tubing 104B, the outlet 142, and the through-hole of the valve seat 120. The sealing member 130 can be made of any suitable material, such as, for example, polypropylene. In some embodiments, the density of the sealing member 130 can be about 0.55 g/cm$^3$.

The minimum threshold fluid level can depend, in part, on the size of the sealing member 130 (e.g., the outer diameter of a spherical sealing member 130), the buoyancy of the sealing member 130 (including the mass and density of the sealing member 130 and the density of the liquid fluid), the angle of the sealing surface of the valve seat 120 relative to a centerline of the through-hole of the valve seat 120, the location of the sealing surface of the valve seat 120 within the housing 110, and the size and shape of the reservoir 116 (e.g., an inner diameter of a cylindrical reservoir 116). In some embodiments, the minimum threshold fluid level can depend, in part, on the orientation of the assembly 102 during use of the assembly 102. For example, the assembly 102 can have a first minimum threshold fluid level when disposed in an upright or vertical orientation (e.g., hanging from an IV pole) and a second minimum threshold fluid level when the assembly 102 is disposed on a surface in an orientation nearer to horizontal than vertical. The remaining fluid volume in the reservoir 116 may be greater, for example, when the fluid level in the reservoir 116 is at the second minimum threshold fluid level than when the fluid level in the reservoir 116 is at the first minimum threshold fluid level. In some embodiments, the sealing member 130 can be sufficiently buoyant such that a portion of the sealing member 130 remains above the fluid level when the sealing member 130 is disposed in liquid fluid within the reservoir 116.

In some embodiments, the sealing member 130 can have any suitable density, mass, and outer diameter such that the sealing member 130 is prevented from contacting the inner surface of the housing 110 (e.g., a portion of the inner surface of the housing 110 above the fluid level and/or a portion of the inner surface of the housing 110 under the fluid level) when the assembly 102 is oriented such that a central axis of the housing 110 is transverse relative to the horizontal such that the upper end of the housing 110 (e.g., the inlet end) is vertically higher than the lower end of the housing 110 (e.g., the outlet end). In some embodiments, the sealing member 130 can have an outer diameter that is sufficiently small relative to the inner diameter of the housing 110 (e.g., equal to or less than 90% of the inner diameter of the housing 110) such that the sealing member 130 does not contact the inner surface of the housing 110, particularly when the assembly 102 is disposed on a surface such that a centerline of the housing 110 is angled relative to the horizontal, such that the travel of the sealing member 130 is not slowed and air is not allowed to pass into the through-hole of the valve seat 120 prior to the sealing member 130 sealing with the valve seat 120.

The sealing member 130 can have any suitable outer diameter such that the sealing member 130 can seal with the valve seat 120 and fluidically isolate the reservoir 116 from the outlet 142. In some embodiments, the ratio of the outer diameter of the sealing member 130 and the inner diameter of the housing 110 can be about 67%. In some embodiments, the outer diameter of the sealing member 130 can be sufficiently large relative to the inner diameter of the housing 110 such that the sealing member 130 can be easily and/or reliably dislodged from the valve seat 120 when the reservoir 116 has been refilled such that the fluid level is above the minimum threshold fluid level. For example, the outer diameter of the sealing member 130 can be greater than 44% of the inner diameter of the housing 110. In some embodiments, the outer diameter of the sealing member 130 can be sufficiently large relative to the inner diameter of the housing 110 such that the sealing member 130 does not have to line up concentrically with the through-hole of the valve seat 120 until reaching a portion of the sealing surface of the valve seat 120 corresponding to a minimum threshold fluid level to seal effectively with the valve seat 120, and such that the sealing member 130 does not seal unintentionally with the valve seat 120 when the fluid line is above the minimum threshold fluid level. For example, the outer diameter of the sealing member 130 can be sufficiently large relative to the inner diameter of the housing 110 (and relative to a narrow jet of water entering the reservoir 116 through the inlet 152) such that the narrow jet of water entering the reservoir 116 through the inlet 152 cannot entrain the sealing member 130 and push the sealing member 130 to seal with the valve seat 120 when the fluid level in the reservoir 116 is above the minimum threshold fluid level. In some embodiments, the sealing member 130 can be spherical and have an outer diameter ranging from between about 50% and about 75% of the inner diameter of the housing 110.

The cap 150 (also referred to as an upper cap) can be coupled to the upper end (e.g., the inlet end) of the housing 110. The extending portion 154 can extend laterally beyond the outer surface of the housing 110 and/or a lower cap including the outlet 142 coupled to the lower end of the housing 110 relative to the central axis of the housing 110. In some embodiments, the extending portion 154 can be formed as a circular brim extending laterally relative to the outer surface of the housing. In some embodiments, the brim can be symmetrical and/or formed such that the brim extends an equal distance beyond the outer surface of the housing in all directions within a plane lying perpendicular to the central axis of the housing 110. The brim can have a circular outer perimeter and an outer diameter larger than an outer diameter of the housing 110. In some embodiments, the extending portion 154 can be formed as a brim extending laterally from the housing such that the brim has an asymmetric shape. In some embodiments, the extending portion 154 can including a number of laterally extending segments (e.g., three or four laterally extending arms). The extending portion 154 can be configured to prevent the housing 110 from becoming inverted (i.e., the outlet end being raised horizontally even with and/or above the inlet end) such that liquid flow is prevented through the outlet 142 and/or the sealing member 130 is prevented from sealing with the valve seat 120. In some embodiments, the extending portion 154 can extend beyond the outer surface of the housing 110 a distance such that the inlet end of the housing 110 is maintained at a sufficient angle such that flow is not prevented and the sealing member 130 can seal with the valve seat 120. The extending portion 154 can also be shaped and sized such that the assembly 102 can be easily packaged for transport and not cumbersome to use.

The extending portion 154 can be configured to maintain the assembly 102 such that the central axis of the housing 110 is maintained at an angle relative to a surface on which the assembly 102 is disposed if the assembly 102 is placed on the surface with the extending portion 154 and the housing 110 or a lower cap including the outlet 142 coupled to the housing 110 in contact with the surface. By extension, depending on the orientation of the surface on which the assembly 102 is disposed, the assembly 102 is maintained at an angle relative to the horizontal. For example, the extending portion 154 can be configured such that, if the assembly 102 is disposed on a horizontal surface (e.g., a surface disposed in a plane substantially parallel to a plane including the surface of liquid fluid in the reservoir 116 of the housing 110) such that the extending portion 154 and the housing 110 or a lower cap coupled to the housing 110 is in contact with the surface, the extending portion 154 can maintain the central axis of the through-hole of the valve seat 120 and/or the central axis of the housing 110 in a transverse orientation relative to the horizontal surface such that the sealing member 130 is configured to seal with the valve seat 120 prior to the fluid level dropping below the threshold minimum fluid level for the particular orientation of the assembly 102 relative to vertical or horizontal. In some embodiments, the extending portion 154 can be configured to maintain the central axis of the through-hole of the valve seat 120 and/or the housing 110 at a minimum angle relative to the surface such that the sealing member 130 is configured to seal with the valve seat 120 prior to the fluid level dropping below the threshold minimum fluid level for the particular orientation of the assembly 102 relative to vertical or horizontal. For example, the minimum angle can be about 8°.

In some embodiments, the threshold minimum fluid level can correspond to the location of the sealing interface between the sealing member 130 and the sealing surface of the valve seat 120. Thus, the threshold minimum fluid level can be a horizontal plane that includes the highest point of the sealing interface on the sealing surface. In some embodiments, when the housing 110 is vertically oriented, the threshold minimum fluid level can correspond to the plane including the entire sealing interface. In some embodiments, when the assembly 102 is disposed on a horizontal surface and a plane including the sealing interface on the sealing surface is transverse to the horizontal surface, the threshold minimum fluid level can correspond to a plane lying parallel to the horizontal surface and including only the uppermost portion of the sealing interface. In some embodiments, the threshold minimum fluid level can correspond to any suitable location on the valve seat 120 (e.g., along the sealing surface or within the through-hole) or the inner surface of the housing 110 that will allow the sealing member 130 to seal with the sealing surface and fluidically isolate the reservoir 116 from the outlet 142.

In some embodiments, a portion of the extending portion 154 can include a first contact point at a maximum lateral extent of the extending portion 154 (e.g., an edge of a brim of the cover 150) and a portion of the housing 110 or a lower cap coupled to the housing can include a second contact point at a maximum lateral extent of the portion of the housing 110 or the lower cap at or near the lower end of the assembly 102 such that a line extending through the first contact point and the second contact point is transverse to the central axis of the through-hole of the valve seat 120 and/or the housing 110 and the angle between the line extending through the first contact point and the second contact point and the central axis of the through-hole of the valve seat 120 and/or the housing 110 is at least a minimum angle. Thus, when the assembly 102 is disposed on a surface, the first contact point and the second contact point both contact the surface and the central axis of the through-hole of the valve seat 120 and/or the housing 110 is disposed at at least the minimum angle relative to the surface. If the surface is horizontal, then the central axis is disposed at at least the minimum angle relative to the horizontal. If the surface is not horizontal, and the housing 110 is disposed on the surface with the upper end of the housing 110 (e.g., the inlet end) vertically higher than the lower end of the housing 110 (e.g., the outlet end), then the central axis is disposed at an angle relative to the horizontal that is greater than the minimum angle.

For example, the first contact point on the extending portion 154 can be located on a lower edge of the cap 150 and the second contact point can be on a lower edge of the housing 110 or a lower cap coupled to the housing 110. The first contact point, the second contact point, and the central axis of the housing 110 can lie in the same plane. The lateral extent of the first contact point relative to the second contact point can determine the angle of the central axis of the through-hole of the valve seat 120 and/or the housing 110 relative to a surface upon which the assembly 102 is disposed when the first contact point and the second contact point simultaneously contact the surface.

The hydrophobic filter 170 can permit air to exit the housing 110 via the vent 160 but prevent liquid fluid from flowing from the reservoir 116 through the vent 160. The hydrophobic filter 170 can have any suitable size openings. For example, the hydrophobic filter 170 can be a 0.2 micron filter. In some embodiments, the hydrophobic filter 170 can define a through-hole in fluid communication with the inlet 152 such that fluid can flow into the reservoir 116 from the inlet 152 via the through-hole. The hydrophobic filter 170 can be shaped and sized such that the hydrophobic filter 170 extends across the entire reservoir 116 with the exception of the through-hole. In some embodiments, the hydrophobic filter 170 can have a circular shape. In some embodiments, the hydrophobic filter 170 can have an outer diameter substantially similar to an inner or outer diameter of the housing 110. In some embodiments, the hydrophobic filter 170 can be disposed within an interior portion of the cap 150 and can have an outer diameter larger than the outer diameter of the housing 110.

The vent 160 included in the cap 150 can be any suitable vent configured to allow air to escape from the reservoir 116. In some embodiments, the vent 160 can also prevent air from traveling into the reservoir 116 via the vent 160. In some embodiments, the vent 160 can include an umbrella valve.

In some embodiments, the fluid source 180 can include a fluid bag containing saline. In some embodiments, the fluid source 180 can include a fluid bag including blood. In some embodiments, the negative pressure source 190 can be configured to apply cyclical and/or periodic negative gauge pressure to the assembly 102 such that each cycle or period of negative pressure can draw a volume of fluid from the reservoir 116. In some embodiments, the negative pressure source 190 can include, for example, a one-way check valve such that fluid drawn through the one-way check valve can be prevented from returning to the outlet 142. In some embodiments, the negative pressure source 190 can include a syringe and a one-way check valve such that the syringe can draw fluid from the reservoir 116, through the valve seat 120, through the outlet 142, through the tubing 104B, through the one-way check valve and into the syringe. In some embodiments, the negative pressure source 190 can include a dual check valve and a manually-operated syringe. For example, the dual check valve can be coupled to the tubing 104B, the manually-operated syringe, and patient infusion tubing. A healthcare provider can draw fluid from the reservoir 116 (e.g., pull on a plunger of the syringe), through the valve seat 120, the outlet 142, the tubing 104B, the dual check valve, and into a barrel of the syringe. The healthcare provider can then transfer the fluid from the barrel of the syringe (e.g., push on the plunger of the syringe), through the dual check valve, through the patient infusion tubing, and into the patient. The healthcare provider can continue cyclically drawing fluid into the syringe barrel and expelling fluid from the syringe barrel until the fluid level drops to a threshold level such that the sealing member 130 seals with the valve seat 120, preventing the healthcare provider from drawing any additional fluid into the syringe barrel until additional liquid fluid has been added to the reservoir 116 and the sealing member 130 released from the valve seat 120. In some embodiments, the negative pressure source 190 can include any suitable infusion device configured to draw fluid from the reservoir 116 via the tubing 104B, such as any of the infusion devices described in International Publication No. WO/2016/138018 and/or U.S. Patent Publication No. 2016/0166761, the contents of each of which are hereby incorporated by reference in their entireties.

In use, the system 100 can be assembled by a user (e.g., a healthcare provider). For example, in some embodiments, the inlet 152 of the assembly 102 can be coupled to a first end of the tubing 104A and the outlet 142 of the assembly 102 can be coupled to a first end of the tubing 104B (via, e.g., an interference or press fit or a coupling mechanism). With the sealing member 130 sealingly engaged with the valve seat 120, a second end of the tubing 104A can be coupled to the fluid source 180. For example, the second end of the tubing 104A can include a spike and the fluid source 180 can be a saline fluid bag having an outlet, and the spike can be coupled to the outlet of the saline fluid bag such that the saline fluid bag is fluidically coupled to the reservoir 116 via the tubing 104A and the inlet 152. The saline fluid bag can then be squeeze purged to remove excess air. For example, the air can be removed from the system 100 by inverting the saline fluid bag such that the outlet is disposed at the top of the saline fluid bag and such that, when the user squeezes the bag, air within the saline fluid bag can flow through the tubing 104A, into the reservoir 116, through the hydrophobic filter 170, and out of the vent 160. When most or all of the air has been removed from the saline fluid bag, the fluid bag can be reoriented such that the outlet is disposed at the bottom of the saline fluid bag. The saline fluid bag can be raised to a height higher than the assembly 102 such that liquid fluid flows through the tubing 104A and the inlet 152 into the reservoir 116. The sealing member 130 can remain sealed with the valve seat 120 as the fluid level rises above the minimum threshold fluid level. When the fluid level in the reservoir 116 is at least higher than a minimum threshold fluid level (e.g., when the reservoir 116 is full of liquid), the user can apply a force to the outer surface of the housing 110 between the bottom of the housing 110 and the center of the sealing member 130 such that the valve seat 120 is deformed and the seal is broken between the sealing member 130 and the valve seat 120. The sealing member 130 can then float to the fluid level.

Fluid can then be drawn from the reservoir 116, through the valve seat 120, through the outlet 142, and into the tube 104B by the negative pressure source 190. As fluid is drawn through the outlet 142, additional fluid can flow from the fluid source 180 into the reservoir 116 such that the fluid level is maintained near the top of the reservoir 116. When substantially all of the fluid contained in the fluid source 180 has been transferred into the reservoir 116 such that the fluid source 180 is substantially empty (or the fluid source 180 has been moved to a vertical position below the inlet 152 of the assembly 102 such that fluid flow into the reservoir 116 ceases), however, the fluid level will begin to drop in the reservoir 116 as fluid continues to be drawn through the outlet 142 by the negative pressure source. If the fluid source 180 includes any air that was not removed during the initial purging process, the air can travel through the tubing 104A, through the inlet 152, into the reservoir 116, through the hydrophobic filter 170, and out of the vent 160. As the fluid level decreases, the sealing member 130 can move toward the valve seat 120. If the negative pressure source 190 applies cyclic or periodic negative pressure to the fluid in the reservoir 116, the fluid in the reservoir 116 can be drawn out cyclically or periodically, with alternating fluid transfer and static periods.

When the fluid level reaches the minimum fluid threshold, the sealing member 130 can sealingly engage with the valve seat 120, fluidically isolating the reservoir 116 from the through-hole of the valve seat 120 and the outlet 142. If the negative pressure source 190 is mid-way though a drawing cycle or period, the sealing of the sealing member 130 with the valve seat 120 can cause a drawing mechanism (e.g., a plunger within a syringe) to cease moving (e.g., due to the isolation of fluid flow causing a negative pressure to build in the tubing 104B downstream of the sealing member 130). When the sealing member 130 is sealingly engaged with the valve seat 120, a static column of fluid can be maintained within the through-hole of the valve seat 120, the outlet 142, and the tubing 104B. With the sealing member 130 sealingly coupled to the valve seat 120, the fluid source 180 can then be separated from the tubing 104A. A second fluid source (e.g., a second saline bag) can then be coupled to the tubing 104A similarly as described above with respect to the fluid source 180 such that the liquid fluid can flow into the reservoir 116. When sufficient liquid fluid is within the reservoir 116, the sealing member 130 can be released from the valve seat 120 as described above (e.g., via squeezing the housing 110 and deforming the valve seat 120) and infusion can continue via the tubing 104B.

In some embodiments, during the portion of operation in which the sealing member 130 is floating at or near the fluid line and not sealed with the valve seat 120 and in which fluid is being drawn from the reservoir 116 into the tubing 104B by the negative pressure source 190, the assembly 102 may be disposed on a surface such that the assembly 102 is not vertically-oriented (e.g., the central axis of the housing and/or the through-hole is not vertically-oriented). For example, the assembly 102 may be placed or inadvertently fall onto a surface (e.g., a patient's bed) such that the assembly 102 is disposed with the cap 150 and a lower portion of the housing 110 or a lower cap coupled to the housing in contact with the surface supporting the assembly 102. In such embodiments, the extending portion 154 of the cap 150 can maintain the assembly 102 in an orientation relative to the surface such that the sealing member 130 will still sealingly engage with the valve seat 120 when the fluid level drops below a minimum threshold level. As described above, the minimum threshold level when the assembly 102 is disposed on a surface with the cap 150 in contact with the surface may be different from the minimum threshold level when the assembly 102 is vertically-oriented. For example, the sealing member 130 may sealingly engaged with the valve seat 120 when more fluid is remaining in the reservoir 116 when the assembly 102 is disposed on the surface than when the assembly 102 is vertically-oriented (e.g., hanging). With the sealing member 130 sealingly engaged with the valve seat 120 and the reservoir 116 fluidically isolated from the outlet 142, the empty fluid source 180 can be replaced with a second fluid source as described above. When the reservoir 116 has been filled with liquid fluid from the second fluid source above the minimum threshold level, the valve seat can be deformed to release the sealing member 130 via squeezing the housing 110 below the sealing member 130 and infusion can continue.

Figure 2:
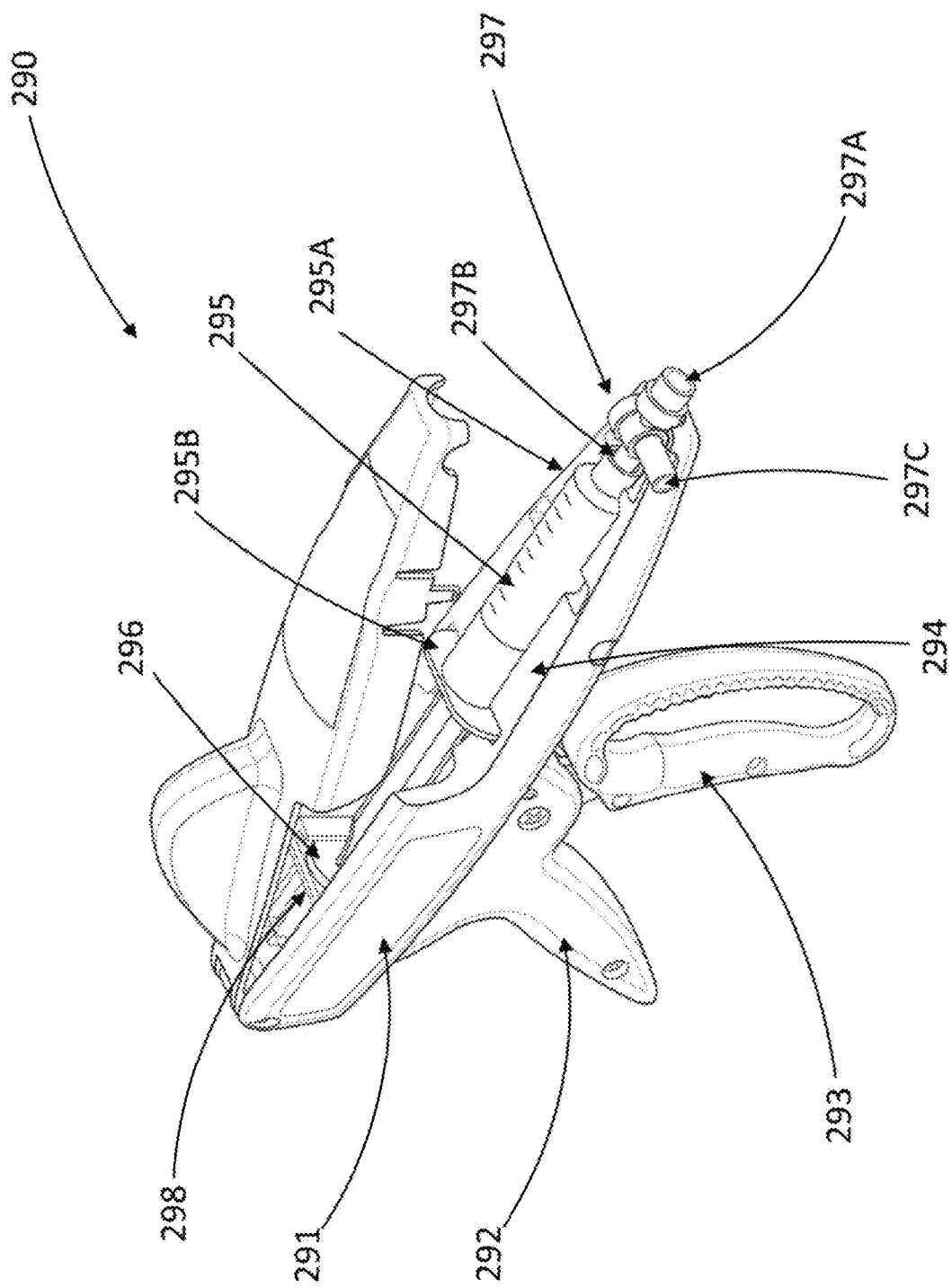
FIG. 2 is a perspective view of an exemplary negative pressure source, according to an embodiment.

In some embodiments, any of the systems described herein, such as the system 100, can include a negative pressure source including an infusion device configured to cyclically draw fluid from an assembly (e.g., the assembly 102) and transfer fluid to a patient. For example, as shown in FIG. 2, a negative pressure source 290 (e.g., an infusion device) can include a housing 291 including a grip 292 and a trigger 293 coupled to the housing 291. The negative pressure source 290 can be the same or similar in structure and/or function to any of the devices described and/or illustrated in International Publication No. WO/2016/138018, such as FIG. 22 of International Publication No. WO/2016/138018. For example, the negative pressure source 290 can include a shuttle mechanism 298 disposed within the housing 291 and mechanically coupled directly or indirectly to the trigger 293 such that the trigger 293 can be actuated to linearly translate the shuttle mechanism 298. As shown in FIG. 2, the housing 291 and the shuttle mechanism 298 can be configured to receive a syringe 294 and a dual check valve assembly 297. The syringe 294 can include a syringe barrel 295 and a plunger 296. The syringe barrel 295 can have a first end 295A and a second end 295B. The dual check valve assembly 297 can include a first end 297A, a second end 297B, and an inlet 297C. The second end 297B of the dual check valve assembly 297 can be coupled to the first end 295A of the syringe barrel 295 such that the interior of the dual check valve assembly 297 is in fluidic communication with a reservoir defined by the syringe barrel 295. The dual check valve assembly 297 can include a first check valve (not shown) disposed within the dual check valve assembly 297 such that fluid can flow through the inlet 297C, through the second end 297B, and into the syringe barrel 295 (e.g., when the plunger 296 is drawn relative to the syringe barrel 295), but fluid is prevented from flowing from the second end 297B and out of the inlet 297C. The dual check valve assembly 297 can include a second check valve (not shown) disposed within the dual check valve assembly 297 such that fluid can be transferred from the syringe barrel 295, through the second end 297B, and through the first end 297A (e.g., toward the patient), but fluid is prevented from being drawn through the first end (e.g., from the patient) and through the second end 297B.

In some embodiments, inlet 297C can be coupled to any of the assemblies described herein, such as the assembly 102, via tubing, such as tubing 104B. The first end 297A of the dual check valve assembly 297 can be coupled to a patient via patient access tubing such that the fluid expelled from the syringe barrel 295 can be transferred into the patient.

In some embodiments, the negative pressure source 290 can include a lever (not shown) extending from the trigger 293 and engaged with the shuttle mechanism 298. The lever can extend from the trigger and include a cam path. The shuttle mechanism 298 can be configured to linearly translate the plunger 296 relative to the syringe barrel 295 in a first direction to draw fluid through the inlet 27C and into the syringe barrel 295 and in a second direction to expel fluid from the syringe barrel 295 through the second end 297B and the first end 297A. Thus, the trigger 293 can be actuated (e.g., pulled toward the grip 292) to rotate the lever, causing the shuttle to translate the plunger 296 in the second direction. The trigger 293 can then be released, causing the shuttle to translate the plunger 296 in the first direction.

In some embodiments, a valve seat can be disposed within a housing (e.g., within a reservoir) of an assembly at a distance from both a first end and a second end of the reservoir. For example, FIG. 3A is a side view of an assembly 302 including a valve seat 320 and a sealing member 330, with the sealing member 330 sealingly engaged with a sealing surface 322 of the valve seat 320. The assembly 302 can be similar in structure and/or function to any of the assemblies described herein. For example, the assembly 302 includes a housing 310, a cap 350, and an outlet 342. The housing 310 has a first end 312 and a second end 314. The housing 310 defines a reservoir 316 and the cap 350 defines an inlet 352. The cap 350 is sealingly coupled to the housing 310 and the inlet 352 can be fluidically coupled to a fluid source (e.g., the fluid source 180 via tubing 104A) such that fluid can be introduced into the reservoir 316 via the inlet 352. The outlet 342 can be coupled to the housing 310 and fluidically coupled to a negative pressure source (e.g., the negative pressure source 190 via tubing 104B) such that fluid can flow toward the negative pressure source from the reservoir 316 via a lumen defined by the outlet 342. The assembly 302 can include a sealing member 330 configured to seal with a sealing surface 322 of the valve seat 320. The valve seat 320 can define a through-hole and be disposed relative to the outlet 342 such that fluid can flow from the reservoir 316 to the outlet 342 via the through-hole of the valve seat 320. The valve seat 320 can be disposed within the reservoir 316 such that the valve seat 320 separates the reservoir 316 into a first reservoir portion 316A between the valve seat 320 and the cover 350 and a second reservoir portion 316B between the valve seat 320 and the outlet 342.

The valve seat 320 and the sealing member 330 can be configured to allow liquid fluid to flow from the first reservoir portion 316A to the second reservoir portion 316B and into the outlet 342 when the liquid fluid level or volume within the reservoir 316 is above a minimum threshold or volume, and to prevent the flow of fluid from the first reservoir portion 316A to the second reservoir portion 316B (and thus, through the outlet 342) when the liquid fluid level or volume within the reservoir 316 is at or below a minimum threshold level or volume, thus preventing air from flowing into the outlet 342. The sealing member 330 can be configured to sealingly engage with the valve seat 320 such that the sealing member 330 obstructs the through-hole. The cap 350 can include a vent 360 such that fluid, such as air, can exit the reservoir 316 via the vent 360. The system 300 can also include a hydrophobic filter 370 disposed between the reservoir 316 and the vent 360 such that liquid fluid that has been introduced into the reservoir 316 via the inlet 352 can be prevented from exiting the reservoir 316 via the vent 360. The cap 350 can also include an extending portion 354 such that at least a portion of the cap 350 extends laterally beyond a sidewall of the housing 310 relative to a central axis of the housing 310.

The valve seat 320 can be formed as or include a diaphragm defining a central through-hole. In some embodiments, the valve seat 320 and the housing 310 can be formed as a one-piece structure. In some embodiments, the valve seat 320 and the housing 310 can be separately formed, and the valve seat 320 can be coupled to the housing via any suitable method such as, e.g., adhesive or via engagement between a flange projecting form the inner surface of the housing 310 and the valve seat 320. As shown in FIG. 3A, the valve seat 320 can be disposed a distance from the bottom of the housing 310 such that, for example, a user's fingers can be used to squeeze a portion of the housing 310 to deform the valve seat 320 (and thus, the sealing surface 322) and release the sealing member 330. For example, the valve seat 320 can be disposed a distance H1 from the second end 314 of the housing 310, so that the distance H2, which is the distance from the center of the sealing member 330 to the second end 314 of the housing 310 when the sealing member 330 is sealingly engaged with the sealing surface 322 of the valve seat 320, is sufficiently large such that a user can squeeze the housing 310 between the center of the sealing member 330 and the second end 314 of the housing 310 such that the valve seat 320 is deformed and the sealing member 330 is released. For example, the distance H2 can be range from between about 1.5 cm to about 3 cm.

Figure 3B:
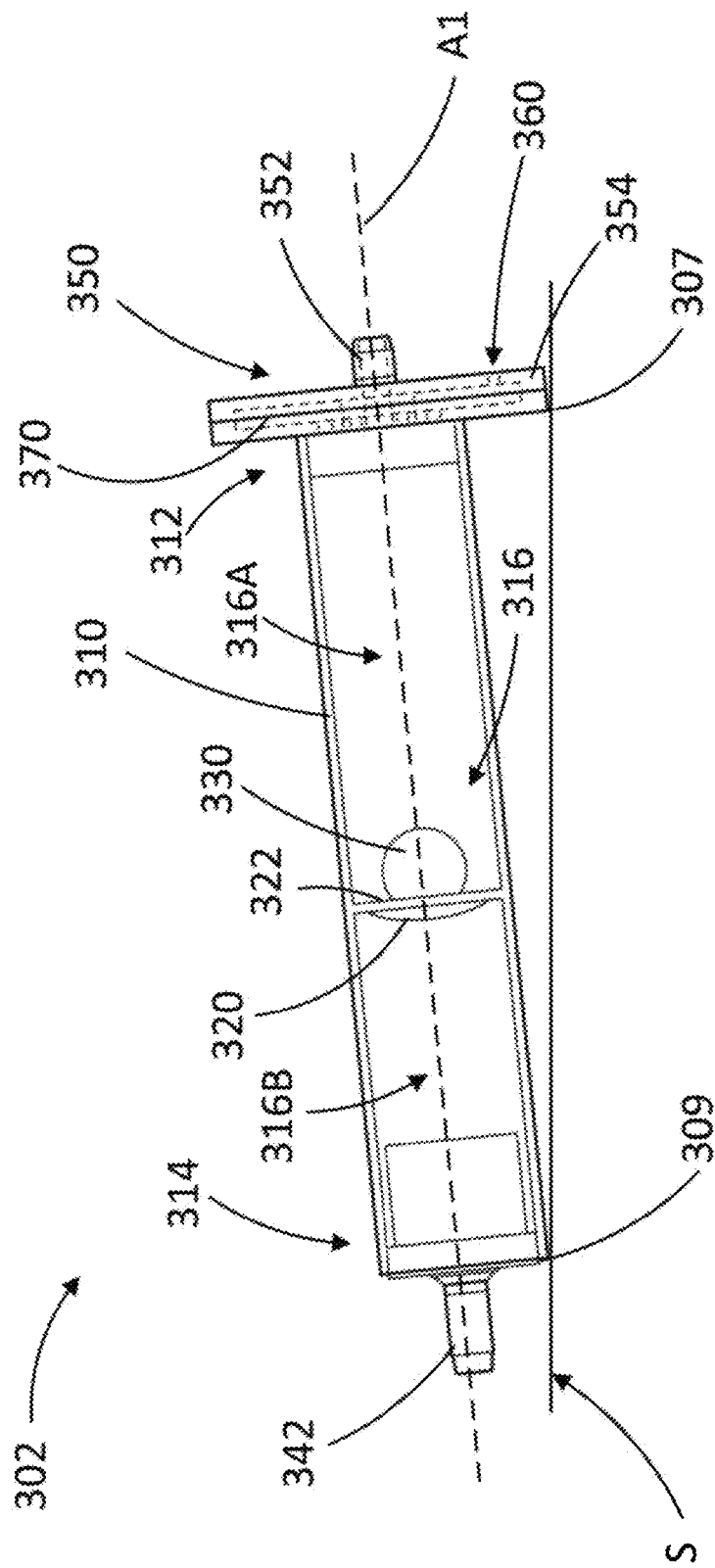
FIG. 3B is a side view of the assembly of FIG. 3A in an orientation in which the assembly is disposed on a surface.

FIG. 3B is a side view of the assembly 302 disposed on a surface S (which in this illustration is a horizontal surface) with the sealing member 330 sealingly engaged with the valve seat 320. The cap 350 and the second end 314 are each in contact with the surface S. For example, the extending portion 354 can include a first contact point 307 and the housing 310 can include a second contact point 309. As a result of the extending member 354 extending laterally beyond the outer surface of the housing 310 relative to a central axis A1 of the housing 310, when the first contact point 307 and the second contact point 309 contact the surface S, the central axis A1 of the housing 310 is maintained at a minimum angle relative to horizontal such that the first end 312 is vertically higher than the second end 314 of the housing 310. The extending portion 354 can maintain the central axis A1 of the housing 310 at a sufficient angle such that the sealing member 330 can seal with the sealing surface 322 of the valve seat 320 prior to air flowing into the outlet 342.

Figure 4:
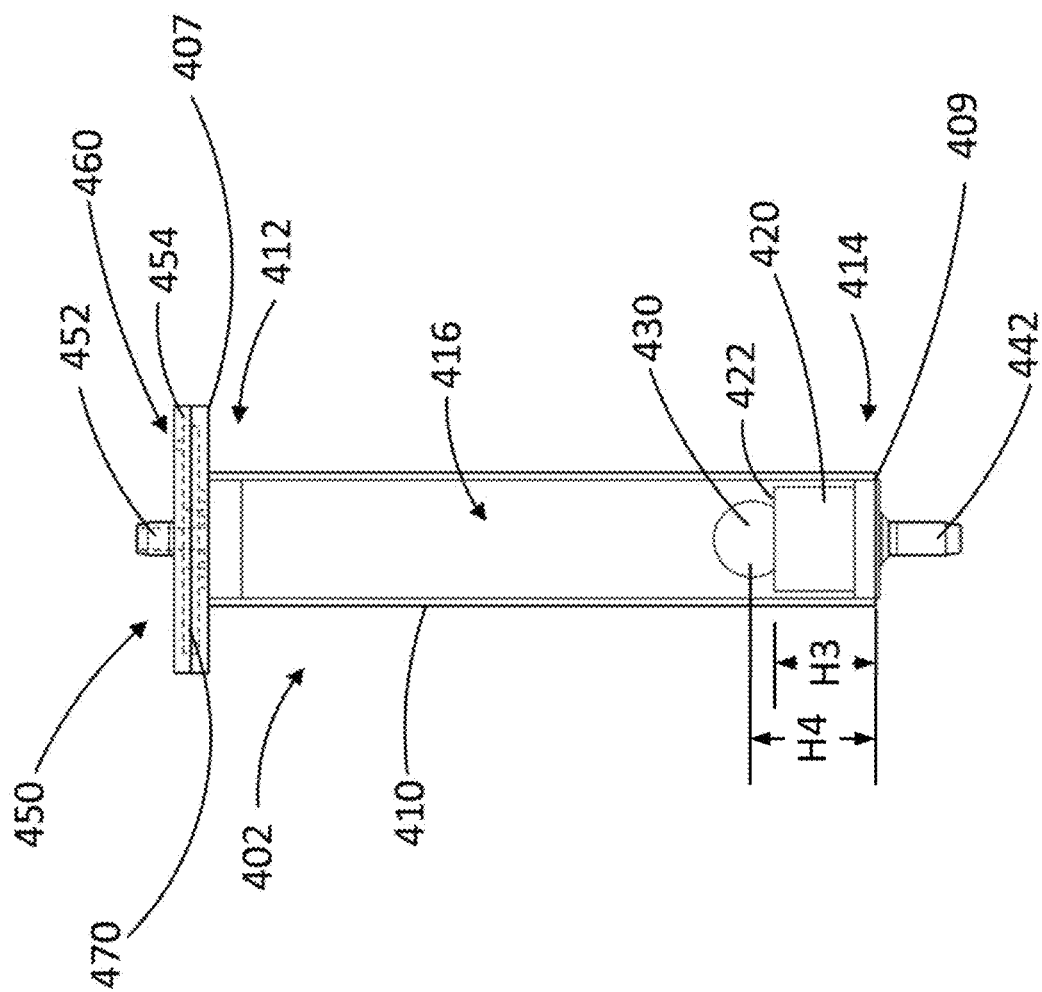
FIG. 4 is a side view of an assembly in a vertical orientation, according to an embodiment.

In some embodiments, a valve seat can be a separate component disposed within a housing of an assembly adjacent or proximate to the lower end of the housing. As shown in FIG. 4, which is a side view of an assembly 402 with a sealing member 430 engaged with a sealing surface 422 of a valve seat 420, the valve seat 420 is disposed adjacent a second end 414 of the housing 410. The assembly 402 can be similar in structure and/or function to any of the assemblies described herein, such as, for example, the assembly 102. For example, in addition to the housing 410, the sealing member 430 and the valve seat 420, the assembly 402 can include a cap 450 and an outlet 442. The housing 410 has a first end 412 opposite the second end 414 and defines a reservoir 416. The cap 450 defines an inlet 452. The cap 450 is sealingly coupled to the housing 410 and the inlet 452 can be fluidically coupled to a fluid source (e.g., a fluid source such as the fluid source 180 via tubing such as tubing 104A) such that fluid can be introduced into the reservoir 416 via the inlet 452. The outlet 442 can be coupled to the housing 410 and fluidically coupled to a negative pressure source (e.g., a negative pressure source such as the negative pressure source 190 via a tubing such as the tubing 104B) such that fluid can flow toward the negative pressure source from the reservoir 416 via a lumen defined by the outlet 442. The assembly 402 can include a sealing member 430 configured to seal with a sealing surface 422 of the valve seat 420. The valve seat 420 can define a through-hole and be disposed relative to the outlet 442 such that fluid can flow from the reservoir 416 to the outlet 442 via the through-hole of the valve seat 420.

The valve seat 420 and the sealing member 430 can be configured to allow liquid fluid to flow from the reservoir 416 into the outlet 442 when the liquid fluid level or volume within the reservoir 416 is above a minimum threshold fluid level or volume, and to prevent the flow of fluid from the reservoir 416 through the outlet 442 when the liquid fluid level or volume within the reservoir 416 is at or below a minimum threshold fluid level or volume, thus preventing air from flowing into the outlet 442. For example, the sealing member 430 can be configured to sealingly engage with the valve seat 420 such that the sealing member 430 obstructs the through-hole.

The sealing surface 422 can be of a sufficient height relative to the second end 414 of the housing 410 such that, when the sealing member 430 is in a sealing configuration with the sealing surface 422 and the fluid level is above the minimum threshold fluid level, a user can squeeze the housing (e.g., between a finger and a thumb of the user) below the center of the sealing member 430 to deform the valve seat 420 and the sealing surface 422 such that a seal between the sealing member 430 and the valve seat 420 is broken and the sealing member 430 is released from the sealing surface 422. For example, the valve seat 420 can have a height of H3 such that, for example, the maximum distance between the sealing surface 422 and the second end 414 of the housing 410 is the height H3. A distance H2, which is a distance from the center of the sealing member 430 to the second end 414 of the housing 410 when the sealing member 430 is sealingly engaged with the sealing surface 422 of the valve seat 420, can be sufficiently large such that a user can squeeze the housing 410 between the center of the sealing member 430 and the second end 414 of the housing 410 such that the valve seat 420 is deformed and the sealing member 430 is released. For example, the distance H4 can be between about 1.5 cm to about 3 cm or greater than about 3 cm.

In some embodiments, the valve seat 420 can be monolithically formed with the housing 410. In some embodiments, the valve seat 420 can be a separate component from the housing 410. For example, the valve seat 420 can be molded or cast in silicone. The second end 414 of the housing 410 can include a barb (not shown) such that the valve seat 420 can be coupled to the housing 410 via the barb. In some embodiments, the valve seat 420 can be retained by the barb via, for example, an interference fit and/or adhesive. In some embodiments, the valve seat 420 can be retained by an interference fit between the valve seat 420 and the inner surface of the housing 410. In some embodiments, the valve seat 420 can be retained by an interference fit between the valve seat 420 and a lower cap (not shown) including the outlet 442, the lower cap sealingly coupled to the second end 414 of the housing 410.

The cap 450 can include a vent 460 such that fluid, such as air, can exit the reservoir 416 via the vent 460. The system 400 can also include a hydrophobic filter 470 disposed between the reservoir 416 and the vent 460 such that liquid that has been introduced into the reservoir 416 via the inlet 452 can be prevented from exiting the reservoir 416 via the vent 460, while permitting gas (e.g., air) to exit the reservoir 416. The cap 450 can also include an extending portion 454 such that at least a portion of the cap 450 extends laterally beyond a sidewall of the housing 410 relative to a central axis of the housing 410. The extending portion 454 can be shaped similarly and function in use similarly to the extending portion 354 described above such that the central axis of the housing 410 can be maintained at a minimum angle relative to horizontal when the extending portion 454 and the second end 414 (e.g., a first contact point 407 of the extending portion 454 and a second contact point 409 of the second end 414) are disposed on a surface such that, when the fluid level within the reservoir decreases to a threshold minimum level, the sealing member 430 seals with the sealing surface 422 prior to air flowing into the through-hole of the sealing member 420.

Figure 5C:
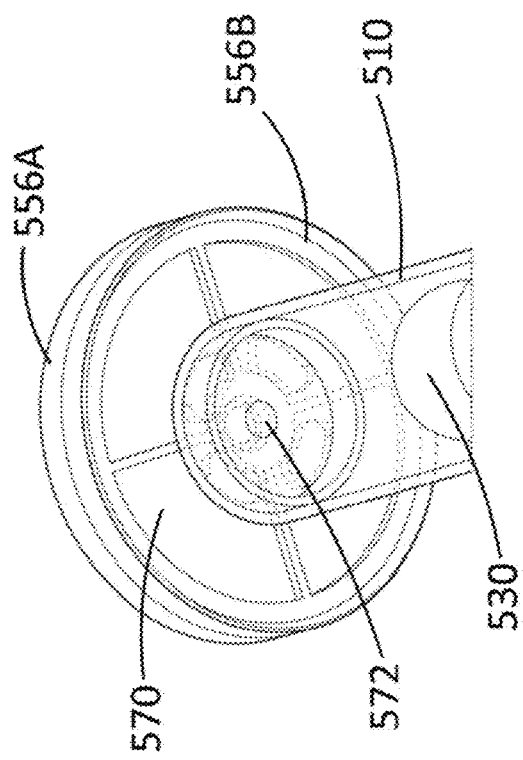
FIG. 5C is a bottom perspective view of a portion of the assembly of FIG. 5A with a second portion of the cap of the assembly shown in phantom.

In some embodiments, an air vent of an assembly can include an umbrella valve. For example, as shown in FIG. 5A, which is a perspective view of a portion of an assembly 502, the assembly 502 includes a cap 550 that can include an umbrella valve 560 configured such that air can escape from a reservoir 516 of the assembly 502. The umbrella valve 560 can be configured to prevent air from entering the reservoir 516. The assembly 502 can be the same or similar in structure and/or function to any of the assemblies described herein. For example, the assembly 502 can include a housing 510 having a first end 512 and defining the reservoir 516. The housing 510 can be sealingly coupled to the cap 550. The cap 550 can include an inlet 552 such that fluid can flow into the reservoir 516 via the inlet 552. The assembly 502 can also include a sealing member 530 (shown in FIGS. 5B and 5C).

Figure 5B:
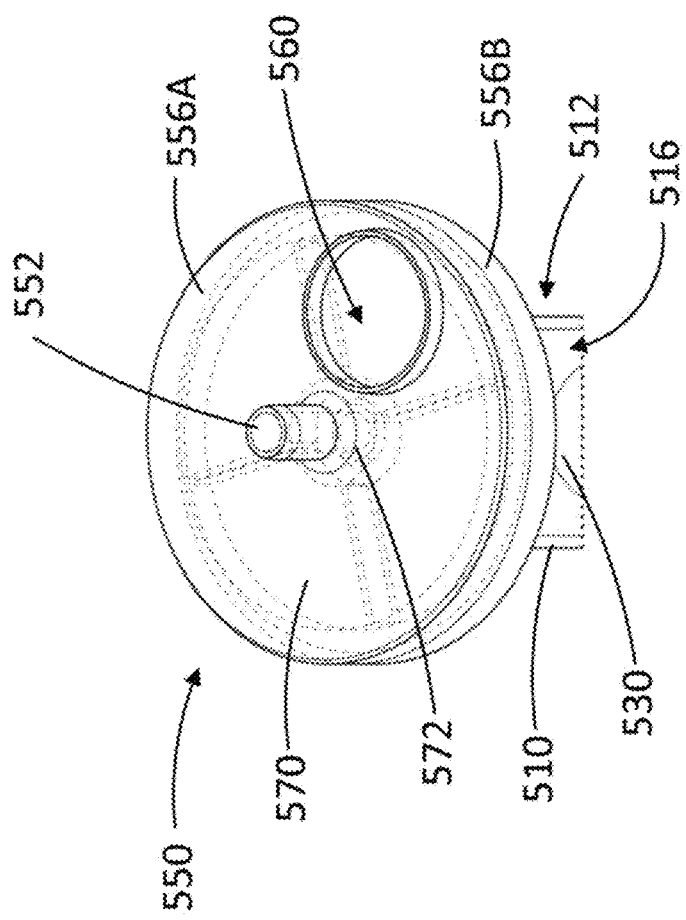
FIG. 5B is a top perspective view of a portion of the assembly of FIG. 5A with a first portion of a cap of the assembly shown in phantom.

The cap 550 can be formed of a first portion 556A and a second portion 556B. As shown in FIGS. 5B and 5C, which are a top perspective view and a bottom perspective view, respectively, with the first portion 556A shown in phantom in FIG. 5B and the second portion 556B and the housing 510 shown in phantom in FIG. 5C, a hydrophobic filter 570 can be disposed between the first portion 556A and the second portion 556B. The hydrophobic filter 570 can define a through-hole 572 such that fluid can pass from the inlet 552, through the through-hole 572, and into the reservoir 516 of the housing 510. The through-hole 572 can be aligned with the inlet 552 such that the through-hole 572 and the inlet 552 are coaxial. The hydrophobic filter 570 can have a larger outer diameter than the inner diameter of the housing 510, allowing for fluid to flow faster into the reservoir 516 of the housing 510 compared to if the hydrophobic filter 570 has a smaller outer diameter, and therefore reduced surface area for fluid to flow through.

The first portion 556A can be sealed to the second portion 556B such that the hydrophobic filter 570 is encapsulated by the first portion 556A and the second portion 556B. The first portion 556A and the second portion 556B can be coupled together via any suitable mechanism or method, such as via ultrasonic welding or adhesive. As shown in FIG. 5B, the umbrella valve 560 is disposed on the opposite side of the hydrophobic filter 570 than reservoir 516. The umbrella valve 560 can be coupled to the first portion 556A and disposed within an opening of the first portion 556A.

Figure 6A:
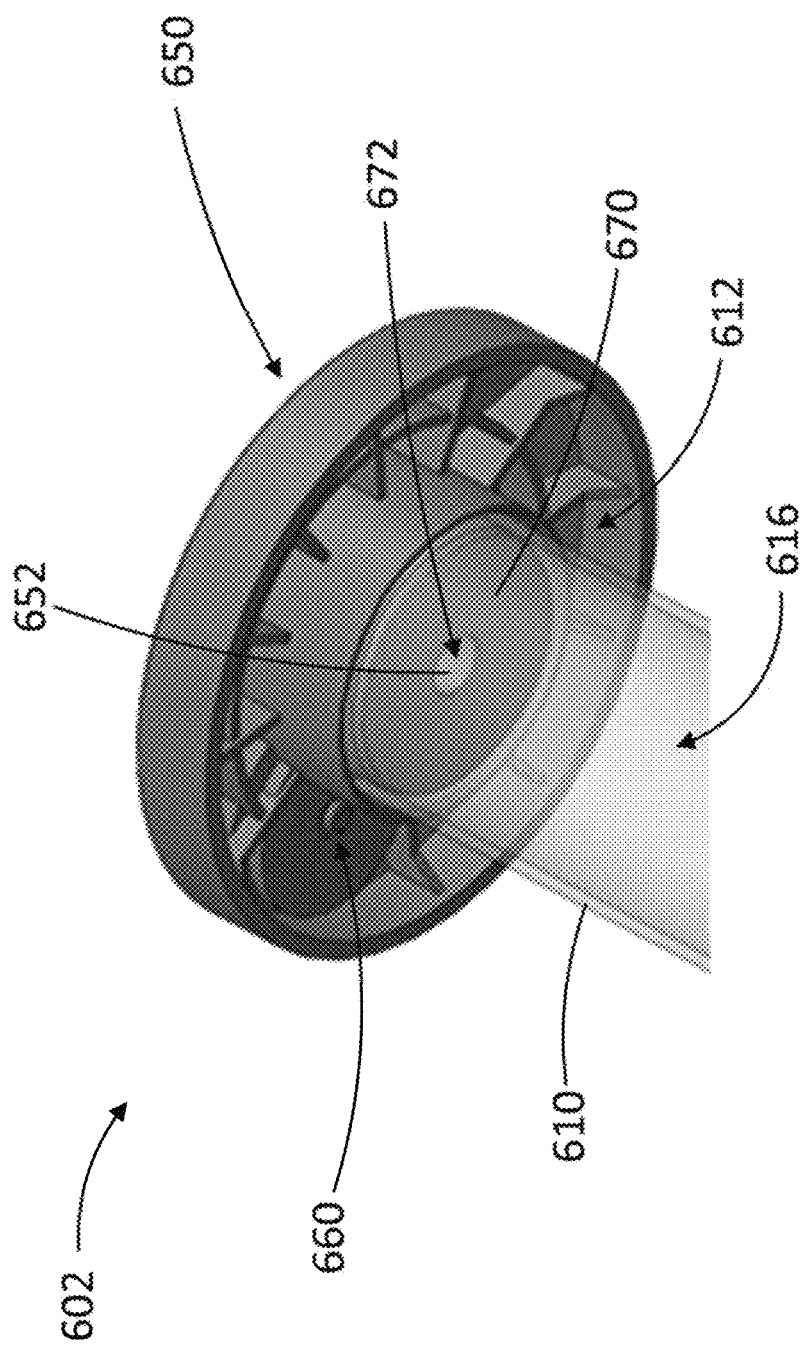
FIG. 6A is a bottom perspective view of a portion of an assembly, according to an embodiment.

In some embodiments, rather than the cap including a first portion and a second portion, the cap can be formed as a monolithic, one-piece structure. For example, as shown in FIG. 6A, which is a perspective view of a portion of an assembly 602, the assembly 602 includes a cap 650. The assembly 602 can be the same or similar in structure and/or function to any of the assemblies described herein. For example, the assembly 602 can include a housing 610 defining a reservoir 616 and having a first end 612, a hydrophobic filter 670 defining a through-hole 672, and a valve 660.

Figure 6B:
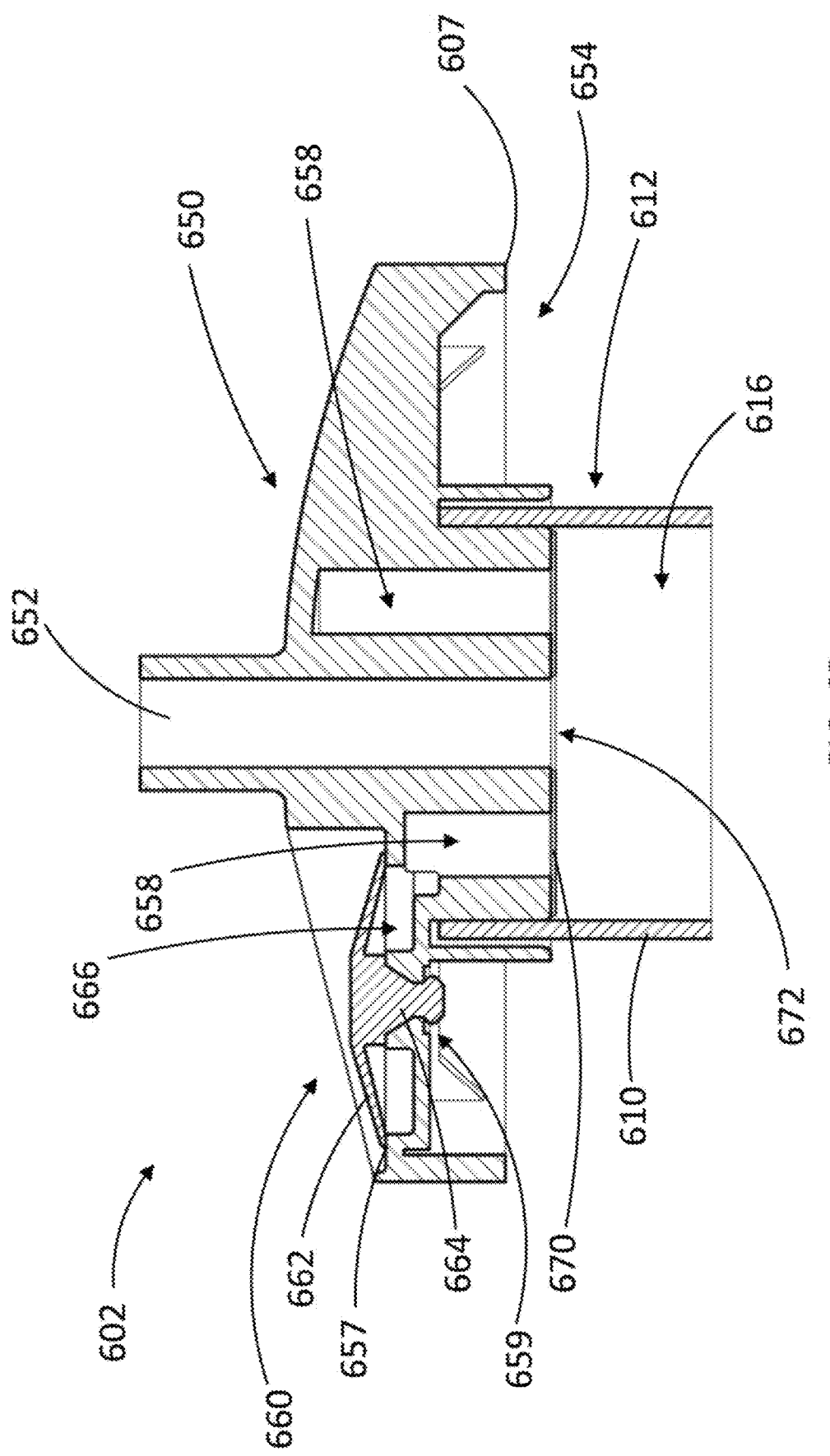
FIG. 6B is a cross-sectional view of a portion of the assembly of FIG. 6A.

The hydrophobic filter 670 can be coupled to the cap 650 via any suitable method such as, for example, via a eutectic die attach process. The hydrophobic filter 670 can be shaped such that the outer diameter of the hydrophobic filter 670 is similar to the inner diameter of the housing 610. As shown in FIG. 6B, which is a cross-sectional view of a portion of the assembly 602, the cap 650 can include a portion that, when the cap 650 and the housing 610 are engaged, extends into the interior of the housing 610.

The cap 650 can be formed as a monolithic structure and coupled to the valve 660. As shown in FIG. 6B, the cap 650 can define a valve recess 659. The umbrella valve 660 can include an umbrella portion 662 and a stem portion 664. The stem portion 664 can be retained within the valve recess 659 and the umbrella portion 662 can be movable relative to a cap sealing surface 657 of the cap 650 between a sealed and an unsealed configuration. The cap 650 can define a first interior space 658. The interior space 658 can, for example, surround the inlet 652 (which extends to the through-hole 672 of the hydrophobic filter 670). The umbrella portion 660 and the cap 650 can collectively define a second interior space 666 in fluid communication with the first interior space 658. The umbrella valve 660 can be configured such that air can pass through the hydrophobic filter 670, into the first interior space 658, and into the second interior space 666. The air in the second interior space 666 can build up and apply pressure to the umbrella valve 660 until the seal between the umbrella portion 662 and the cap sealing surface 657 is disrupted such that air can flow out of the second interior space 666.

Figure 6C:
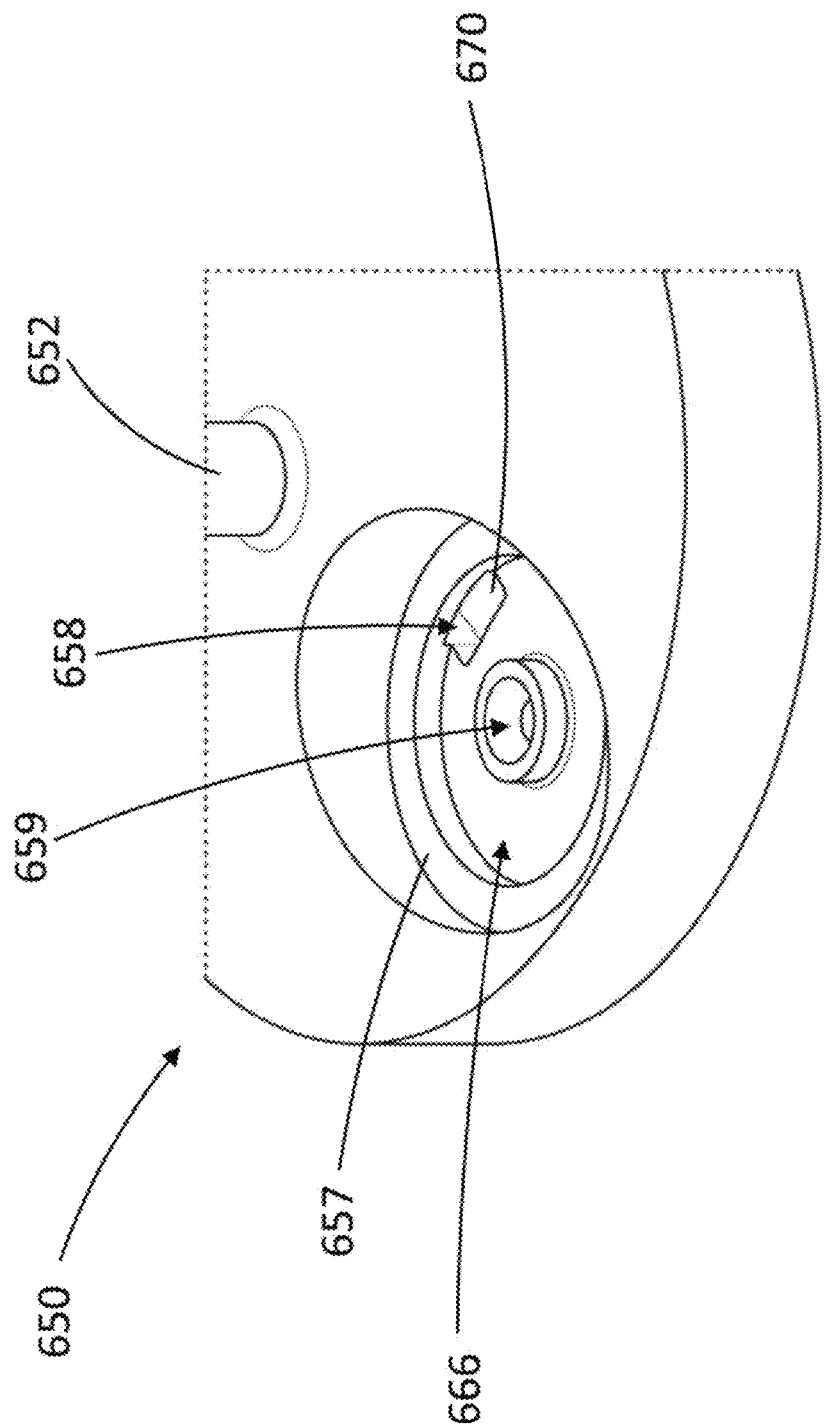
FIG. 6C is a top perspective view of a portion of the assembly of FIG. 6A.

FIG. 6C is a perspective view of a portion of the cap 650 with umbrella valve 660 removed. As shown in FIG. 6C, the cap sealing surface 657 can be shaped as a continuous circular or ring-shaped surface such that the umbrella portion 662 can seal with the cap sealing surface 657 in the absence of sufficient air pressure in the second interior space and/or the first interior space 658 to open the umbrella portion 662.

Figure 7B:
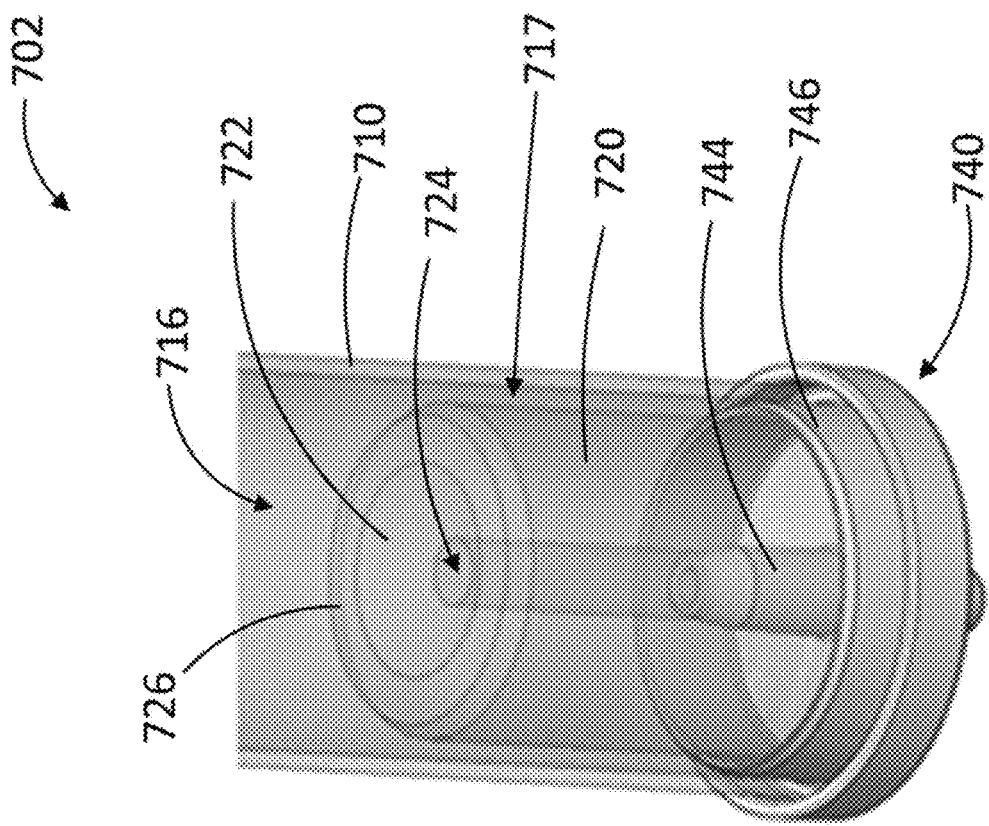
FIG. 7B is a perspective view of a portion of the assembly of FIG. 7A, with the valve seat shown in phantom.
Figure 7A:
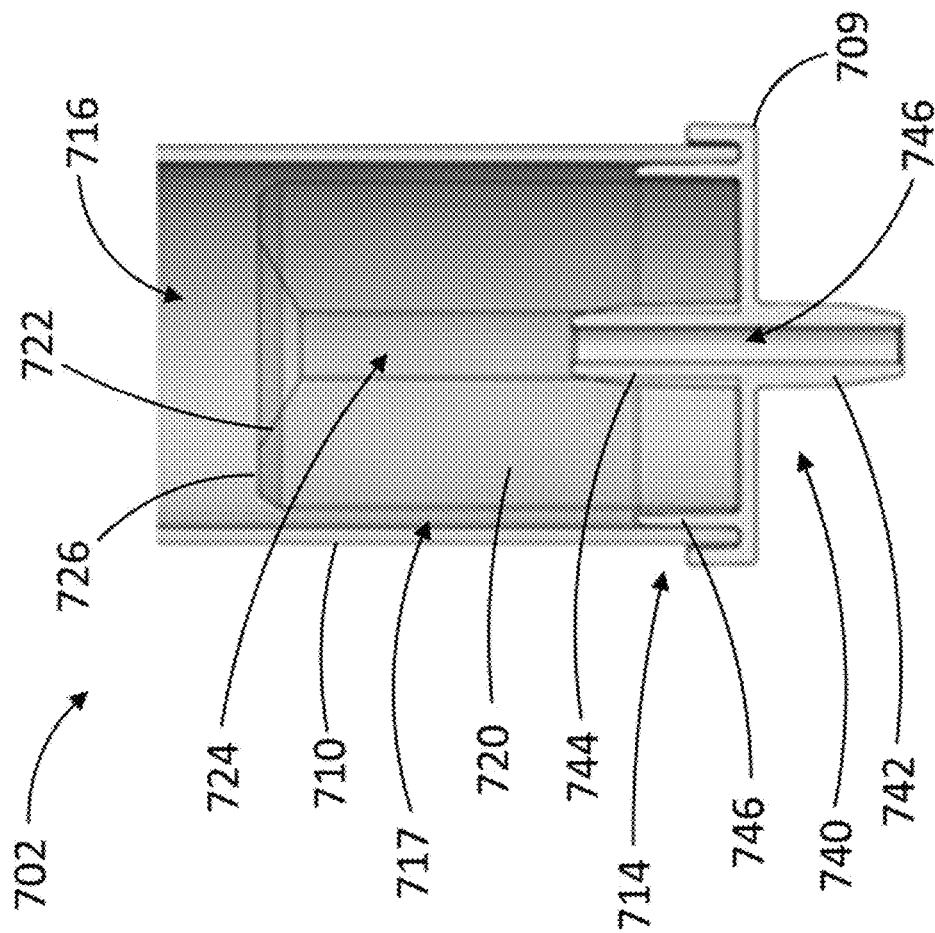
FIG. 7A is a cross-sectional view of a portion of an assembly, with a valve seat of the assembly shown in phantom, according to an embodiment.

FIGS. 7A and 7B are a cross-sectional view and a perspective view of a portion of an assembly 702, respectively. The assembly 702 can be the same or similar in structure and/or function to any of the assemblies described herein. For example, the assembly 702 can include a housing 710, a valve seat 720, and an outlet 742. The assembly 702 can include a lower cap 740 including the outlet 742. The lower cap 740 can be sealingly coupled to a second end 714 of the housing 710. The valve seat 720 defines a through-hole 724. In both FIGS. 7A and 7B, the valve seat 720 is shown in phantom.

The lower cap 740 can include a barb 744. The barb 744 and the outlet 742 can collectively define a lumen 746 such that fluid can flow through the barb 744 and the lumen 742. The lower cap 740 can include a sidewall 746, the sidewall 746 having an outer diameter substantially similar to an inner diameter of the housing 710 such that the sidewall 746 is engaged with the housing 710. The valve seat 720 can be formed of any suitable material, such as silicone. The valve seat 720 can be mated to the barb 744 on the lower cap 740 such that the through-hole 724 of the valve seat 720 is coaxial with the lumen 742 collectively defined by the barb 744 and the outlet 742, and such that the barb 744 retains the valve seat 720 in contact with the lower cap 740. In some embodiments, the outer diameter of the valve seat 720 can be smaller than the inner diameter of the housing 110 such that a circumferential gap 717 is defined between the inner surface of the housing 110 and the outer surface of the valve seat 720. The circumferential gap 717 can be in fluid communication with or included in the reservoir 716.

The valve seat 720 can include a sealing surface 722 and an upper surface 726. The upper surface 726 can be disposed in a plane lying perpendicular to a central axis of the housing 710 and/or through-hole 724. The sealing surface 722 can have a conical or chamfered shape.

Figure 8:
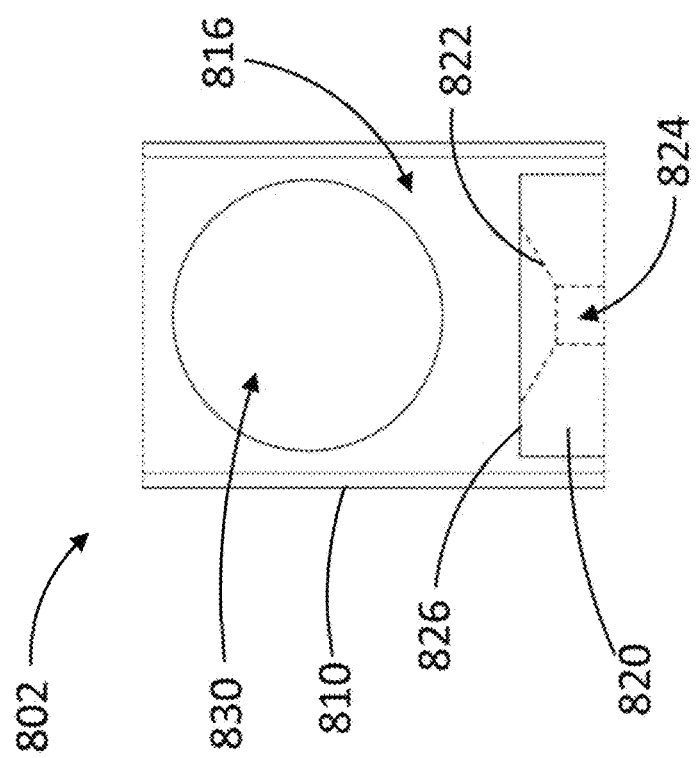
FIG. 8 is a side view of a portion of an assembly, according to an embodiment.

FIG. 8 is a side view of a portion of an assembly 802. The assembly 802 can be the same or similar in structure and/or function to any of the assemblies described herein. For example, the assembly 802 includes a housing 810, a valve seat 820, and a sealing member 830. The housing 810 defines a reservoir 816. The valve seat 820 can include a through-hole 824, a sealing surface 822, and an upper surface 826. The upper surface 826 can be disposed in a plane lying perpendicular to a central axis of the through-hole 824. The sealing surface 822 can be disposed at any suitable angle relative to the upper surface 826 such that the sealing member 830 can seal with the sealing surface 822 when the fluid level reaches a threshold minimum fluid level, regardless of whether the housing 810 is disposed upright (e.g., perpendicular relative to a surface) or transverse, but non-perpendicular, relative to the horizontal. As shown in FIG. 8, the sealing member 830 can have a diameter sufficiently large relative to the distance from the transition between the upper surface 826 and the sealing surface 822 to the inner surface of the housing 810 (e.g., the thickness of the upper surface 826 plus the thickness of any circumferential gap between the valve seat 820 and the inner surface of the housing 810) such that the sealing member 830 does not catch on the upper surface 826 as the fluid level decreased in the reservoir 816, regardless of the orientation of the housing 810.

Figure 9:
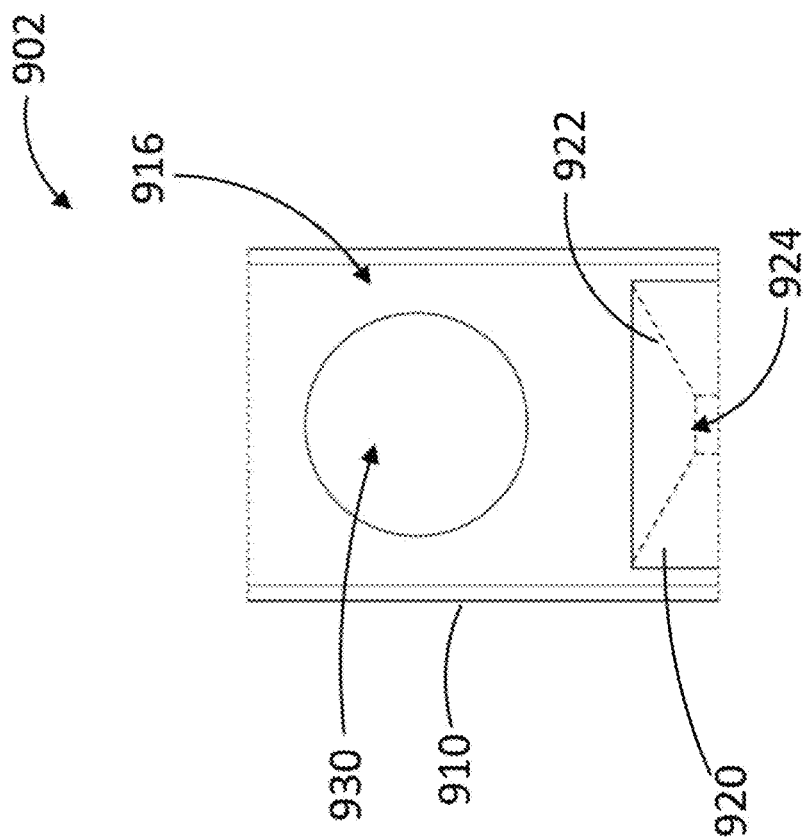
FIG. 9 is a side view of a portion of an assembly, according to an embodiment.

In some embodiments, a sealing surface of a valve seat can extend from a through-hole to an outer surface of a valve seat. For example, FIG. 9 is a side view of a portion of an assembly 902. The assembly 902 can be the same or similar in structure and/or function to any of the assemblies described herein. For example, the assembly 902 includes a housing 910, a valve seat 920, and a sealing member 930. The housing 910 defines a reservoir 916. The valve seat 920 can include a through-hole 924 and a sealing surface 922. The sealing surface 922 can be disposed at any suitable angle relative to a central axis of the through-hole 924 and/or an outer surface of the valve seat 920 such that the sealing member 930 can seal with the sealing surface 922 when the fluid level reaches a threshold minimum fluid level, regardless of whether the housing 910 is disposed upright (e.g., perpendicular to a surface) or transverse relative to a surface. Furthermore, due to the valve seat 920 not including an upper surface lying in a plane perpendicular to the through-hole 924 of the valve seat 920 and the sealing member 930 having a sufficiently larger diameter relative to the distance from the outer surface of the valve seat 920 to the inner surface of the housing 910, the sealing member 930 is prevented from catching on any portion of the valve seat 920 as the sealing member 930 approaches the through-hole 924 as a result of the fluid level decreasing.

Figure 10:
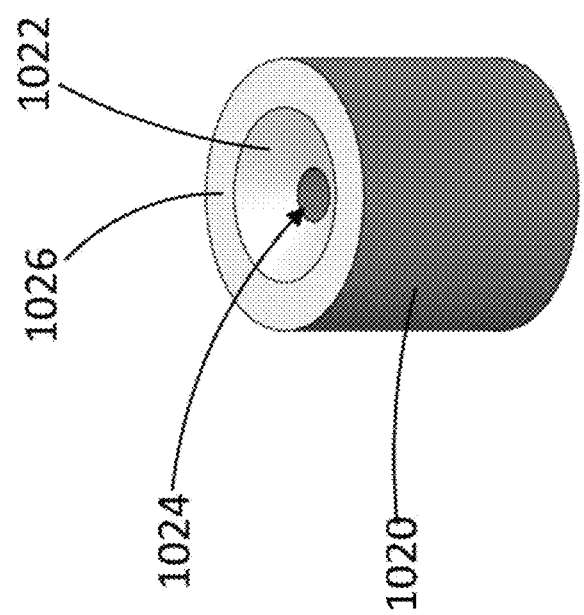
FIG. 10 is a perspective view of a valve seat, according to an embodiment.

FIG. 10 shows a perspective view of a valve seat 1020 that can be the same or similar in structure and/or function to any of the valve seats described herein, such as the valve seat 820. As shown in FIG. 10, the valve seat 1020 can include a through-hole 1024, a sealing surface 1022, and an upper surface 1026. The upper surface 1026 can be disposed in a plane lying perpendicular to a central axis of the through-hole 1024. The sealing surface 1022 can be disposed at any suitable angle relative to the upper surface 1026 such that a sealing member (e.g., a sealing member such as any of the sealing members described herein) can seal with the sealing surface 1022 when a fluid level reaches a threshold minimum fluid level relative to the sealing surface 1022, regardless of whether a housing of an assembly including the valve seat 1020 is disposed upright (e.g., perpendicular to surface) or transverse relative to a surface. The suitable angle of the sealing surface 1022 relative to the central axis of the through-hole 1024 can depend, at least in part, based on the shape and size of the sealing member, the buoyancy of the sealing member, and/or the thickness or inner diameter of the upper surface 1026. The suitable thickness of the sealing surface 1022 can depend, at least in part, on the shape and size of the sealing member and/or the angle of the through-hole 1024 relative to a surface when the valve seat 1020 is included in an assembly including an extending portion and a housing and is disposed such that the extending portion and the housing are both contacting a surface.

Figure 11:
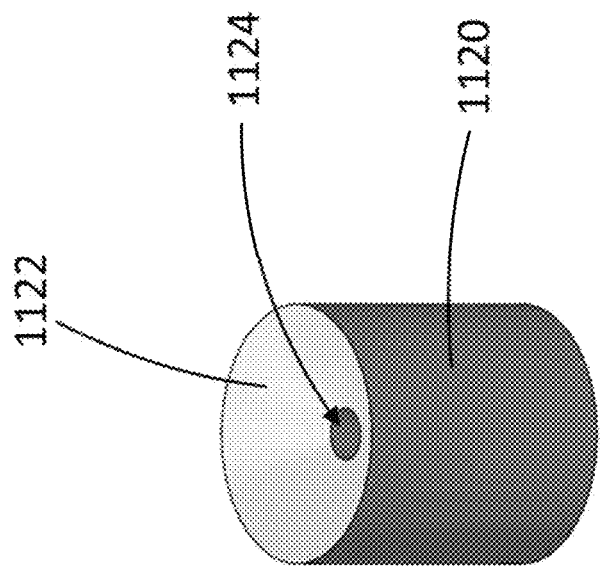
FIG. 11 is a perspective view of a valve seat, according to an embodiment.

FIG. 11 shows a perspective view of a valve seat 1120 that can be the same or similar in structure and/or function to any of the valve seats described herein, such as the valve seat 920. The valve seat 1120 can include a through-hole 1124 and a sealing surface 1122. The sealing surface 1122 can be disposed at any suitable angle relative to a central axis of the through-hole 1124 and/or an outer surface of the valve seat 1120 such that a sealing member (e.g., a sealing member such as any of the sealing members described herein) can seal with the sealing surface 1122 when the fluid level reaches a threshold minimum fluid level, regardless of whether the assembly 1102 is disposed upright (e.g., perpendicular to a surface) or transverse relative to a surface. Furthermore, due to the valve seat 1120 not including an upper surface lying in a plane perpendicular to the through-hole 1124 of the valve seat 1120 and the sealing member having a sufficiently larger diameter, the sealing member is prevented from catching on any portion of the valve seat 1120 as the sealing member 1130 approaches the through-hole as a result of the fluid level decreasing.

Figure 12A:
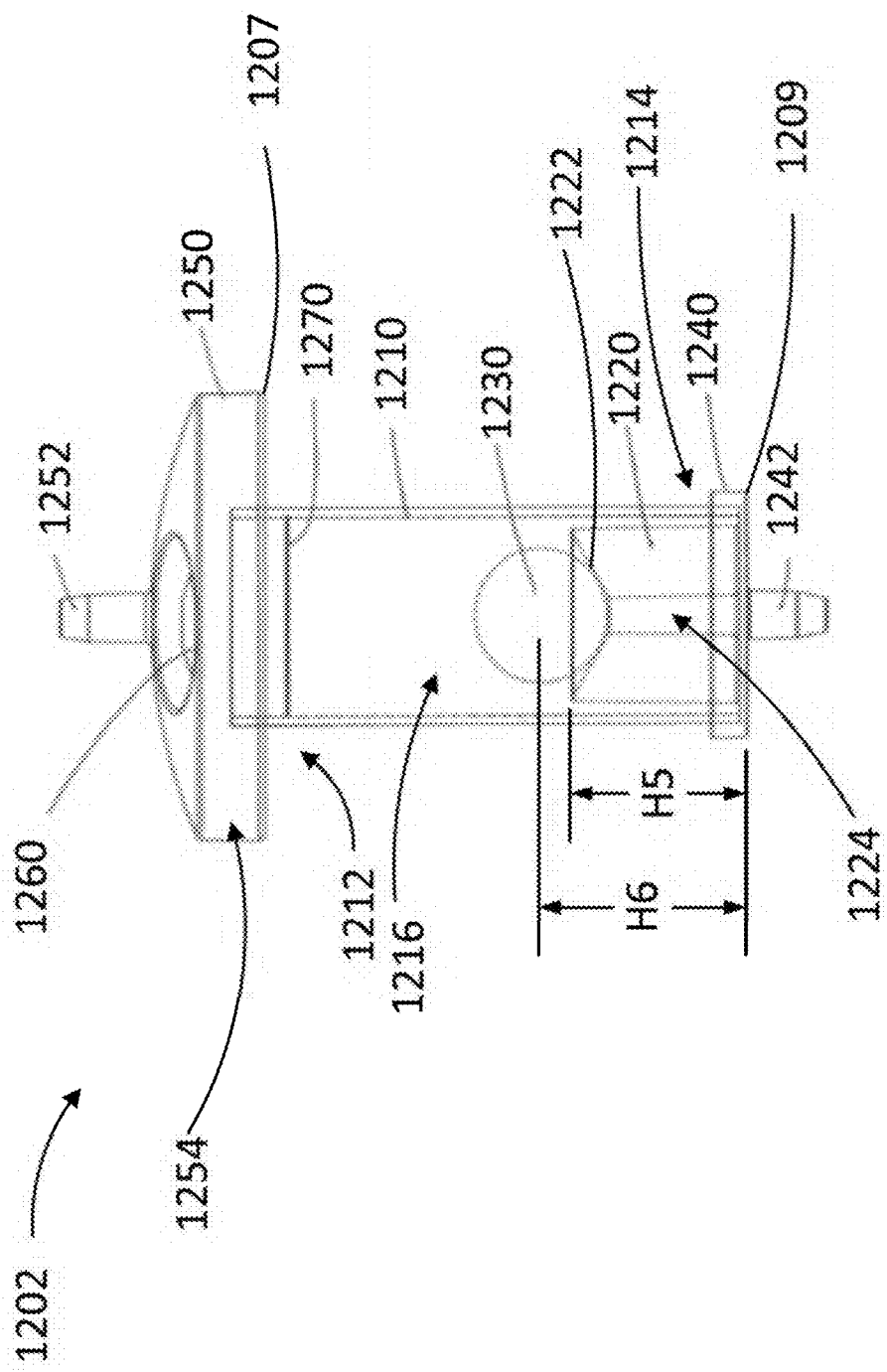
FIG. 12A is a schematic illustration of a side view of an assembly, according to an embodiment.

FIG. 12A is a side view of an assembly 1202. The assembly 1202 can be the same or similar in structure and/or function to any of the assemblies described herein. For example, the assembly 1202 can include a housing 1210, an upper cap 1250, and a lower cap 1240. The assembly 1202 can also include a sealing member 1230 and a valve seat 1220 disposed within the housing 1210. The housing 1210 has a first end 1212 opposite the second end 1214 and defines a reservoir 1216. The upper cap 1250 defines an inlet 1252. The upper cap 1250 is sealingly coupled to the housing 1210 and the inlet 1252 can be fluidically coupled to a fluid source (e.g., a fluid source such as the fluid source 180 via tubing such as tubing 104A) such that fluid can be introduced into the reservoir 1216 via the inlet 1252. The lower cap 1240 can include an outlet 1242 and can be coupled to the second end 1214 of the housing 1210. The valve seat 1220 can be coupled to the lower cap 1240 via any suitable method. The outlet 1242 can be fluidically coupled to a negative pressure source (e.g., a negative pressure source such as the negative pressure source 190 via a tubing such as the tubing 104B) such that fluid can flow toward the negative pressure source from the reservoir 1216 via a lumen defined by the outlet 1242. The sealing member 1230 can be configured to seal with a sealing surface 1222 of the valve seat 1220. The valve seat 1220 can define a through-hole 1224 and be disposed relative to the outlet 1242 such that fluid can flow from the reservoir 1216 to the outlet 1242 via the through-hole 1224 of the valve seat 1220.

The valve seat 1220 and the sealing member 1230 can be configured to allow liquid fluid to flow from the reservoir 1216 into the outlet 1242 when the liquid fluid level or volume within the reservoir 1216 is above a minimum threshold fluid level or volume, and to prevent the flow of fluid from the reservoir 1216 through the outlet 1242 when the liquid fluid level or volume within the reservoir 1216 is at or below a minimum threshold fluid level or volume, thus preventing air from flowing into the outlet 1242. For example, the sealing member 1230 can be configured to sealingly engage with the valve seat 1220 such that the sealing member 1230 obstructs the through-hole 1224. The valve seat 1220 and the sealing member 1230 can be configured to remain sealingly engaged such that the reservoir 1216 is fluidically isolated from the outlet 1242 after fluid has been added to the reservoir 1216 such that the fluid level is above the minimum threshold fluid level until the seal between the sealing member 1230 and the valve seat 1220 is manually disrupted via squeezing and deforming the housing 1210 and the valve seat 1220.

The sealing surface 1222 can be of a sufficient height relative to the second end 1214 of the housing 1210 such that, when the sealing member 1230 is in a sealing configuration with the sealing surface 1222, a user can squeeze the housing (e.g., between a finger and a thumb of the user) below the center of the sealing member 1230 to deform the valve seat 1220 and the sealing surface 1222 such that a seal between the sealing member 1230 and the valve seat 1220 is broken and the sealing member 1230 is released from the sealing surface 1222. For example, the valve seat 1220 can have a height of H5 such that, for example, the maximum distance between the sealing surface 1222 and the second end 1214 of the housing 1210 is a distance H5. A distance H6, which is a distance from the center of the sealing member 1230 to the second end 1214 of the housing 1210 when the sealing member 1230 is sealingly engaged with the sealing surface 1222 of the valve seat 1220, can be sufficiently large such that a user can squeeze the housing 1210 between the center of the sealing member 1230 and the second end 1214 of the housing 1210 such that the valve seat 1220 is deformed and the sealing member 1230 is released.

The cap 1250 can include a vent 1260 such that fluid, such as air, can exit the reservoir 1216 via the vent 1260. The apparatus 1202 can also include a hydrophobic filter 1270 disposed between the reservoir 1216 and the vent 1260 such that liquid fluid that has been introduced into the reservoir 1216 via the inlet 1252 can be prevented from exiting the reservoir 1216 via the vent 1260. The cap 1250 can also include an extending portion 1254 such that at least a portion of the cap 1250 extends laterally beyond a sidewall of the housing 1210 relative to a centerline of the housing 1210. The extending portion 1254 can be shaped similarly and function in use similarly to the extending portion 354 described above such that the central axis of the housing 1210 can be maintained at a minimum angle relative to horizontal when the extending portion 1254 and the second end 1214 are disposed in contact with a surface such that, when the fluid level within the reservoir decreases to a minimum threshold fluid level, the sealing member 1230 seals with the sealing surface 1222 prior to air flowing into the through-hole 1224 of the sealing member 1220. For example, in some embodiments, a portion of the extending portion 1254 can include a first contact point 1207 and a portion of the lower cap 1209 can include a second contact point 1209 such that, when the assembly 1202 is disposed on a surface (e.g., a horizontal surface), the first contact point 1207 and the second contact point 1209 both contact the surface and the central axis of the through-hole 1224 of the valve seat 1220 and the central axis of the housing 1210 is disposed at at least a minimum angle relative to the horizontal. For example, the first contact point 1207 on the extending portion 1254 can be located on a lower edge of the cap 1250 and the second contact point 1209 can be on a lower edge of the lower cap 1240 coupled to the housing 1210. The first contact point 1207, the second contact point 1209, and the central axis of the housing 1210 can lie in the same plane, and a line running through the first contact point 1207 and the second contact point 1209 can intersect the central axis of the housing 1210 at an angle corresponding to the angle of the central axis of the housing 1210 relative to a surface upon which the assembly 1202 can be disposed when the assembly 1202 is disposed on the surface. Although the minimum angle relative to horizontal described above corresponds to the minimum angle of the central axis of the housing 1210 such that when the reservoir decreases to a minimum threshold fluid level, the sealing member 1230 seals with the sealing surface 1222 prior to air flowing into the through-hole 1224 of the sealing member 1220, in some embodiments the minimum angle corresponds to the minimum angle of the central axis of the housing 1210 relative to horizontal such that when the reservoir decreases to a minimum threshold fluid level, the sealing member 1230 seals with the sealing surface 1222 prior to air flowing from the outlet 1224 and/or exiting the reservoir 1216.

Figure 12B:
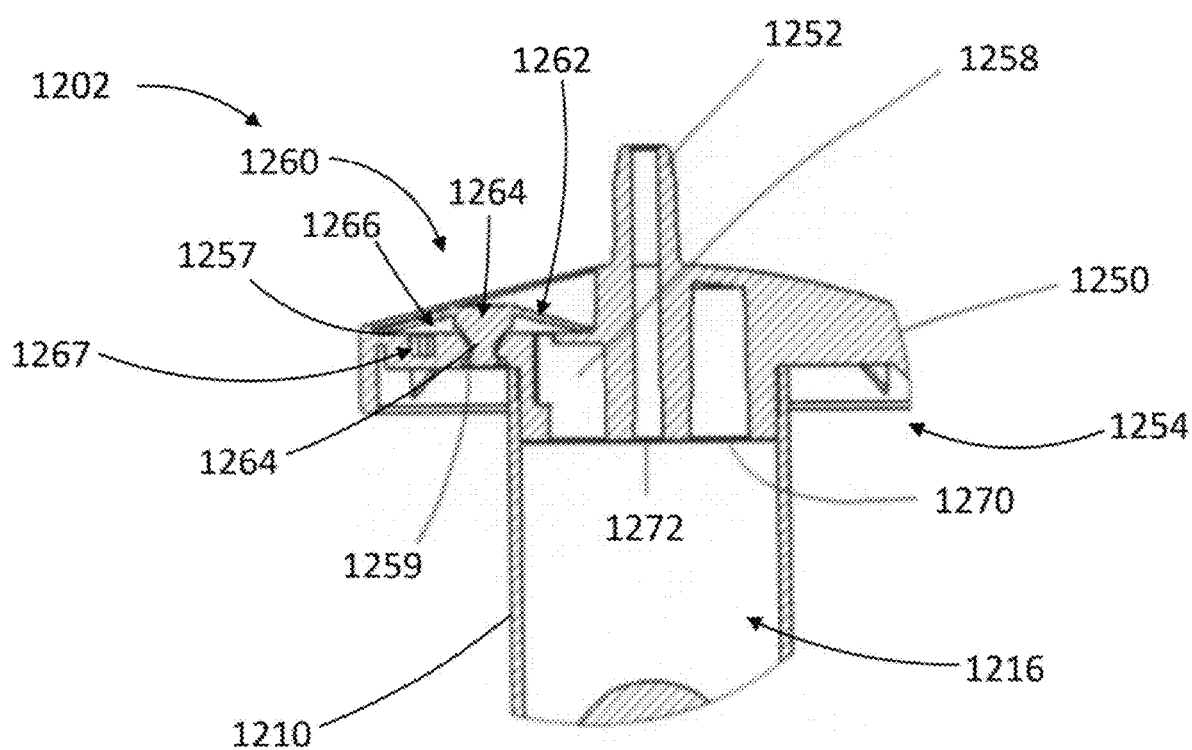
FIG. 12B is cross-sectional view of a portion of the assembly of FIG. 12A.

FIG. 12B is a cross-sectional illustration of a portion of the assembly 1202. As shown in FIG. 12B, the cap 1250 can be formed as a monolithic structure and can define a valve recess 1259. The valve 1260 can include an umbrella portion 1262 and a stem portion 1264. The stem portion 1264 can be retained within the valve recess 1259 and the umbrella portion 1262 can be movable relative to a cap sealing surface 1257 of the cap 1250 between a sealed and an unsealed configuration. The cap 1250 can define a first interior space 1258. The interior space 1258 can, for example, surround the inlet 1252 (which extends to the through-hole 1272 of the hydrophobic filter 1270). The umbrella portion 1260 and the cap 1250 (e.g., the cap sealing surface 1257 and the annular space 1267) can collectively define a second interior space 1266 in fluid communication with the first interior space 1258. The umbrella valve 1260 can be configured such that air can pass through the hydrophobic filter 1270, into the first interior space 1258, and into the second interior space 1266. The air in the second interior space 1266 can build up and apply pressure to the umbrella valve 1260 until the seal between the umbrella portion 1262 and the cap sealing surface 1257 is disrupted such that air can flow out of the second interior space 1266.

Figure 12C:
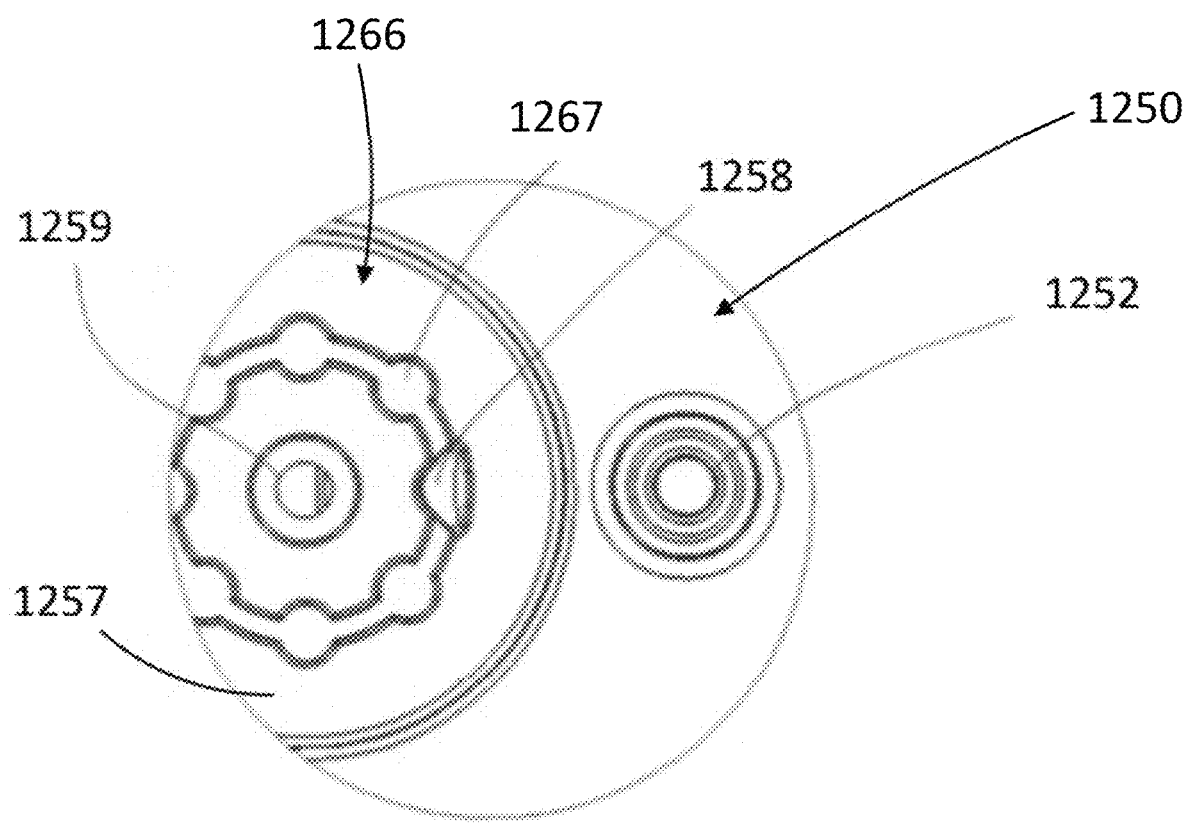
FIG. 12C is a top view of a portion of the assembly of FIG. 12A.
Figure 12E:
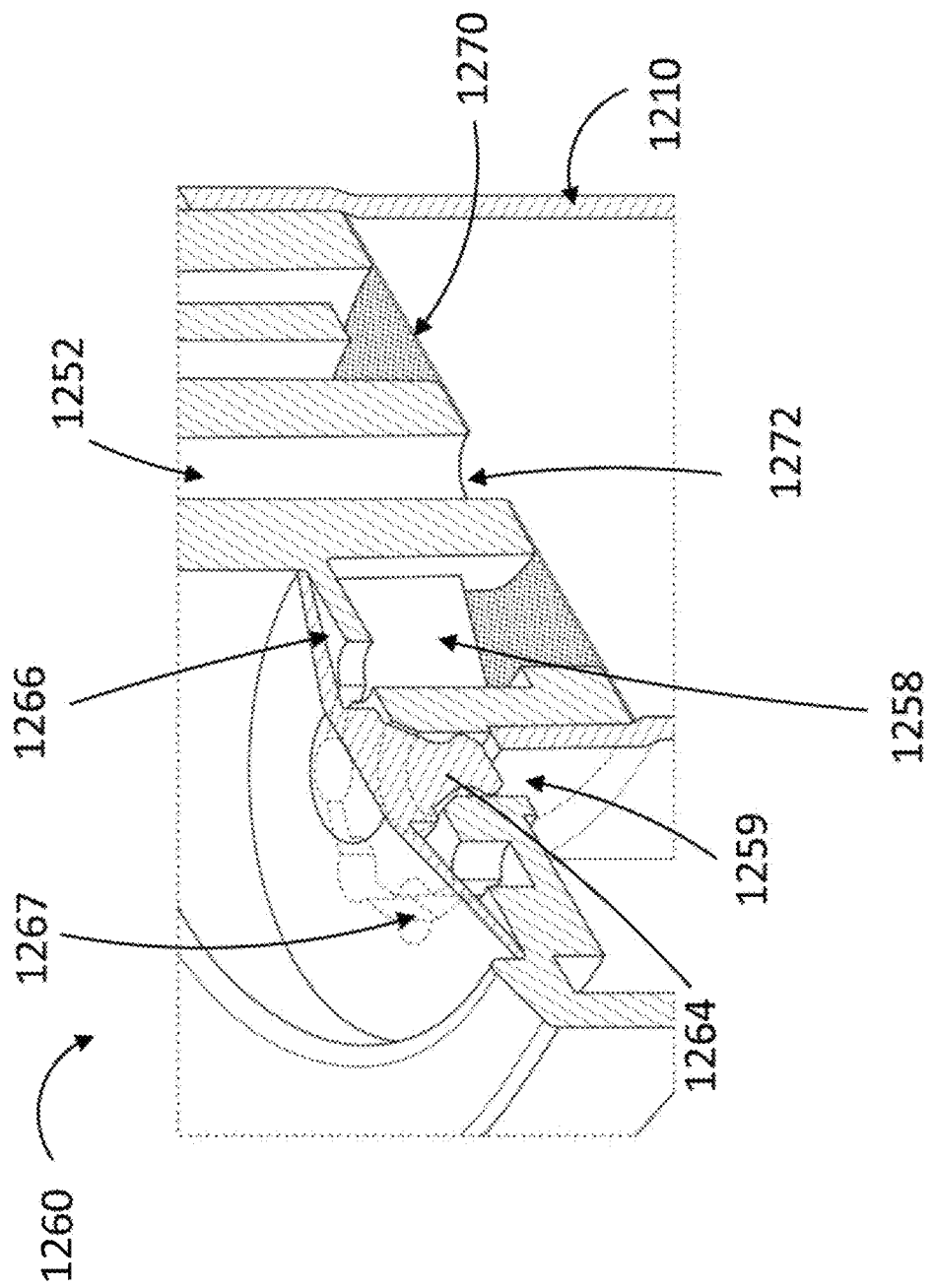
FIG. 12E is a perspective view of a cross-section of the assembly of FIG. 12A.
Figure 12F:
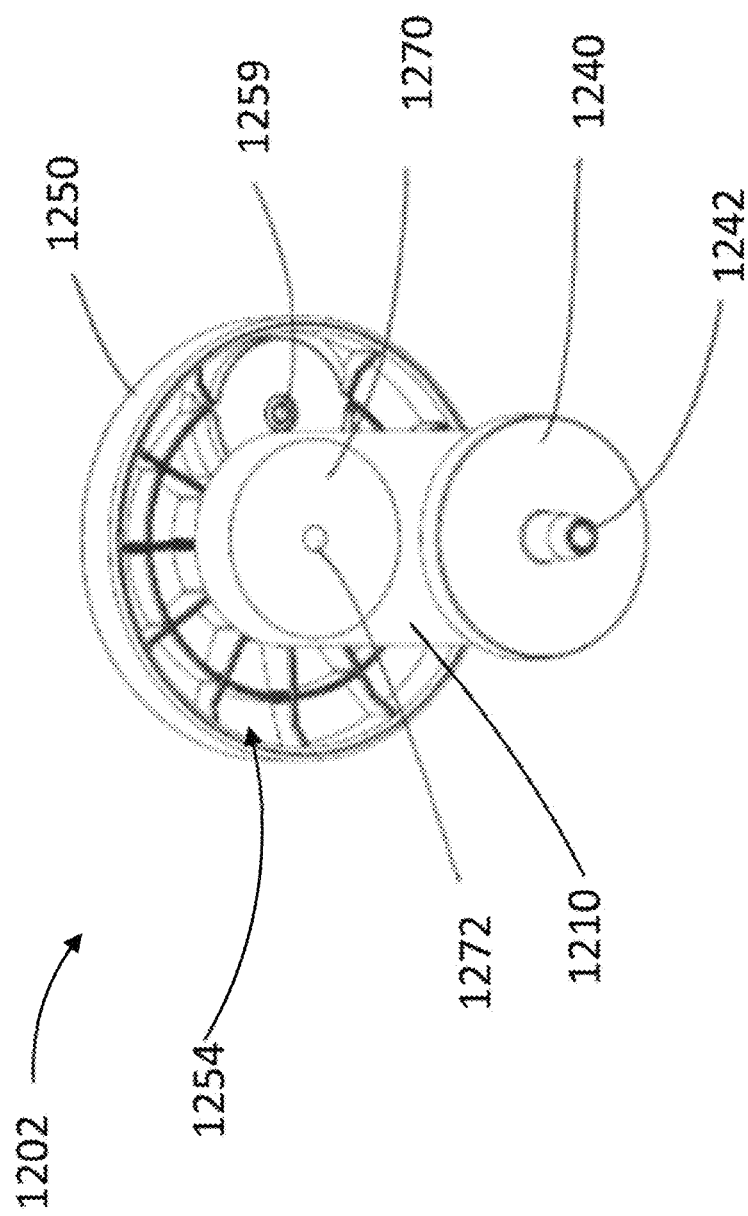
FIG. 12F is a bottom perspective view of the assembly of FIG. 12A.

As shown in FIGS. 12C and 12D, which are a top view and a perspective view, respectively, of a portion of the cap 1250 with the valve 1260 removed, the annular space 1267 can be fluidically coupled to the first interior space 1259 and can include circular portions disposed at intervals along a ring-shaped portion. As shown in FIG. 12E, which is a perspective view of a portion of a cross-section of the assembly 1202, the umbrella valve 1260 can be configured to be disposed within a recessed portion of the cap 1250. As shown in FIG. 12F, which is a bottom perspective view of the assembly 1202, the extending portion 1254 of the cap 1250 can extend laterally from the housing 1210 in all directions, forming a brim-shape. Thus, the assembly 1202 can be placed on a surface such that any edge of the lower cap 1240 and any edge of the outer extent of the cap 1250 contact the surface and maintain the central axis of the housing 1210 such that the central axis is transverse relative to the surface. Therefore, any portion of the lower cap 1240 and any portion of the cap 1250 lying in the same plane as each other and as the central axis of the housing 1210 can be identified as the first contact point 1207 and the second contact point 1209, respectively.

FIG. 12G is a cross-sectional illustration of the valve seat 1220. As shown in FIG. 12G, the valve seat 1220 can include an upper surface 1226. The upper surface 1226 can be disposed in a plane lying perpendicular to a central axis of the through-hole 1224. The sealing surface 1222 can be disposed at any suitable angle relative to the upper surface 1226 such that the sealing member 1230 can seal with the sealing surface 1222 when a fluid level reaches a threshold minimum fluid level relative to the sealing surface 1222, regardless of whether the housing 1210 is disposed upright (e.g., perpendicular to surface) or transverse relative to a surface. The thickness T1 of the upper surface 1226 of the valve seat 1220 can be sufficiently small such that the sealing member 1230 will not catch on the upper surface 1226 of the valve seat 1220 as the fluid level decreases and the sealing member 1230 approaches the sealing surface 1222.

Figure 12H:
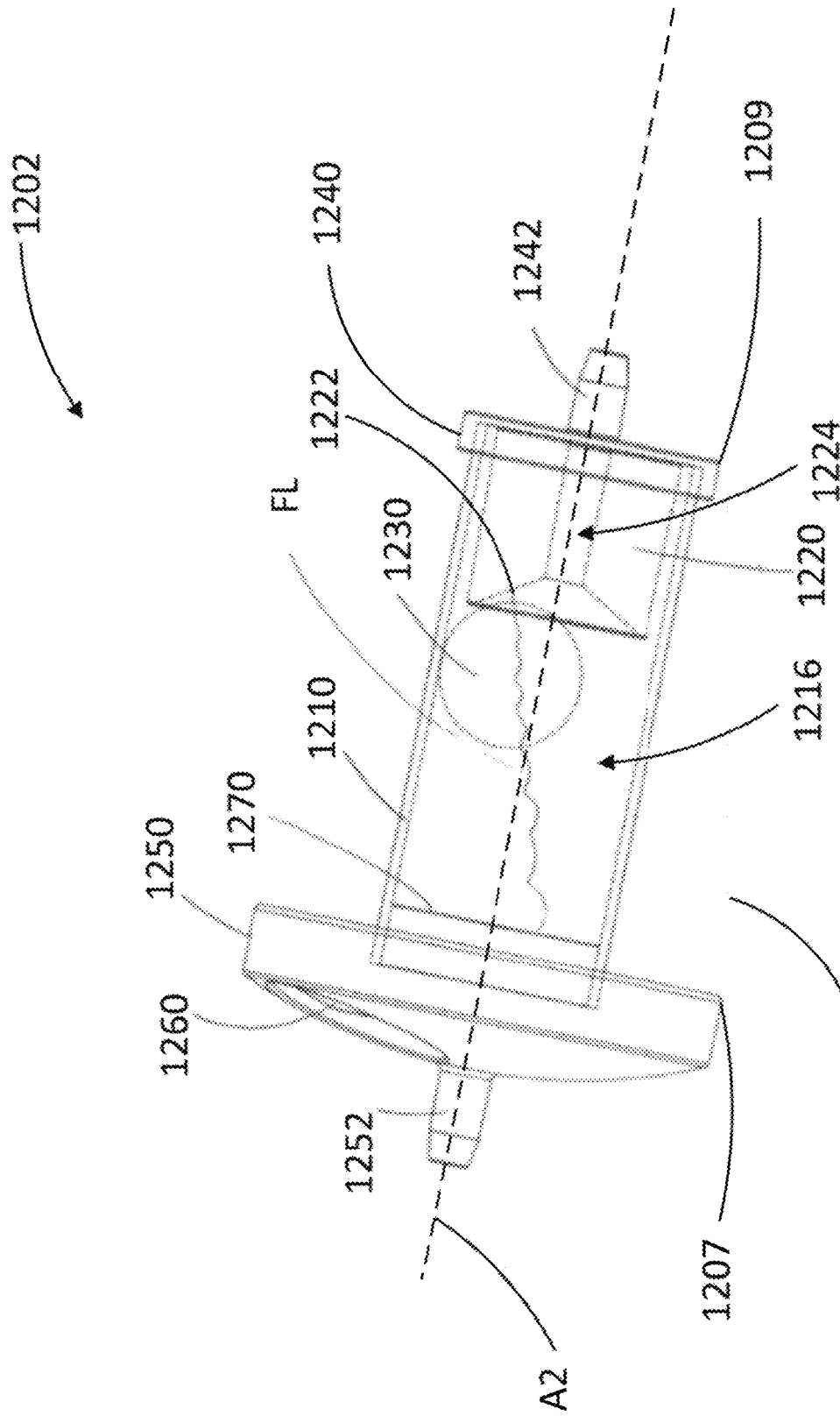
FIG. 12H is a side view of the assembly of FIG. 12A disposed on a surface.

FIG. 12H is a side view of the assembly 1202 disposed such that the first contact point 1207 and the second contact point 1209 are in contact with a surface S and the fluid level FL within the reservoir 1216 is above a minimum threshold fluid level. As shown, the sealing member 1230 is near the sealing surface 1222 but has not yet sealed with the sealing surface 1222. Also as shown, although the surface S is disposed in a plane substantially parallel to a plane containing the surface of the liquid fluid within the reservoir (i.e. horizontal), the central axis A2 of the housing 1210 and through-hole 1224 of the valve seat 1220 are transverse to the surface S such that the sealing member 1230 will seal with the sealing surface 1222 when the fluid level FL reaches the minimum threshold fluid level.

Figure 13A:
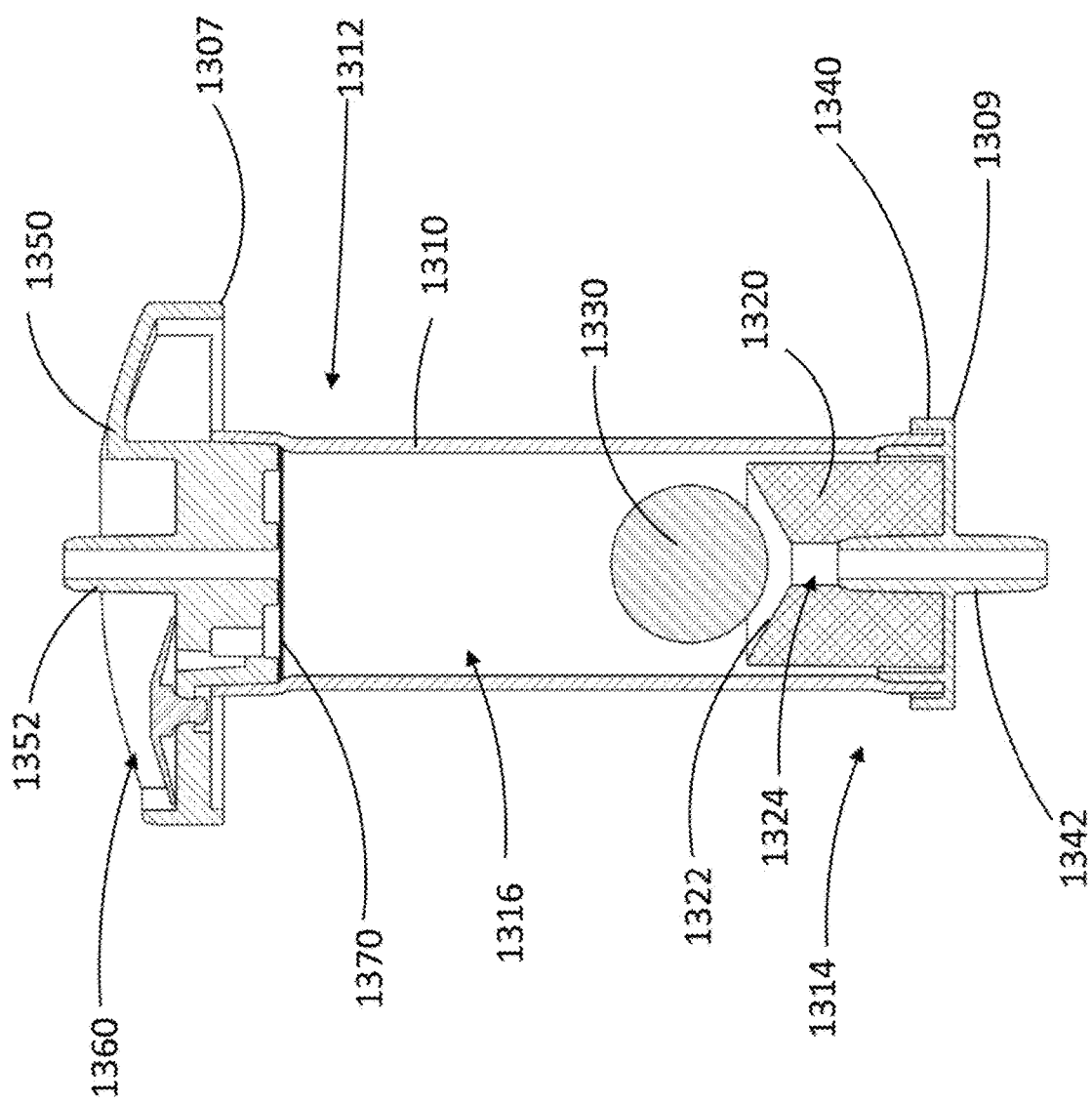
FIG. 13A is a cross-sectional view of an assembly, according to an embodiment.

In some embodiments, the cap can include no annular space and interior spaces with reduced volume compared to the cap 1250. For example, FIG. 13A is a cross-sectional illustration of an assembly 1302. The assembly 1302 can be the same or similar in structure and/or function to any of the assemblies described herein. For example, the assembly 1302 can include a housing 1310, an upper cap 1350, and a lower cap 1340. The assembly 1302 can also include a sealing member 1330 and a valve seat 1320 disposed within the housing 1310. The housing 1310 has a first end 1312 opposite the second end 1314 and defines a reservoir 1316. The upper cap 1350 defines an inlet 1352. The upper cap 1350 is sealingly coupled to the housing 1310 and the inlet 1352 can be fluidically coupled to a fluid source (e.g., a fluid source such as the fluid source 180 via tubing such as tubing 104A) such that fluid can be introduced into the reservoir 1316 via the inlet 1352. The lower cap 1340 can include an outlet 1342 and can be coupled to the second end 1314 of the housing 1310. The valve seat 1320 can be coupled to a barb of the lower cap 1340. The outlet 1342 can be fluidically coupled to a negative pressure source (e.g., a negative pressure source such as the negative pressure source 190 via a tubing such as the tubing 104B) such that fluid can flow toward the negative pressure source from the reservoir 1316 via a lumen defined by the outlet 1342. The sealing member 1330 can be configured to seal with a sealing surface 1322 of the valve seat 1320. The valve seat 1320 can define a through-hole 1324 and be disposed relative to the outlet 1342 such that fluid can flow from the reservoir 1316 to the outlet 1342 via the through-hole 1324 of the valve seat 1320.

The valve seat 1320 and the sealing member 1330 can be configured to allow liquid fluid to flow from the reservoir 1316 into the outlet 1342 when the liquid fluid level or volume within the reservoir 1316 is above a minimum threshold fluid level or volume, and to prevent the flow of fluid from the reservoir 1316 through the outlet 1342 when the liquid fluid level or volume within the reservoir 1316 is at or below a minimum threshold fluid level or volume, thus preventing air from flowing into the outlet 1342. For example, the sealing member 1330 can be configured to sealingly engage with the valve seat 1320 such that the sealing member 1330 obstructs the through-hole 1324. The valve seat 1320 and the sealing member 1330 can be configured to remain sealingly engaged such that the reservoir 1316 is fluidically isolated from the outlet 1342 after fluid has been added to the reservoir 1316 such that the fluid level is above the minimum threshold fluid level until the seal between the sealing member 1330 and the valve seat 1320 is manually disrupted via squeezing and deforming the housing 1310 and the valve seat 1320.

The cap 1350 can include a vent 1360 such that fluid, such as air, can exit the reservoir 1316 via the vent 1360. The assembly 1302 can also include a hydrophobic filter 1370 disposed between the reservoir 1316 and the vent 1360 such that liquid fluid that has been introduced into the reservoir 1316 via the inlet 1352 can be prevented from exiting the reservoir 1316 via the vent 1360. The cap 1350 can also include an extending portion 1354 such that at least a portion of the cap 1350 extends laterally beyond a sidewall of the housing 1310 relative to a central axis of the housing 1310. The extending portion 1354 can be shaped similarly and function in use similarly to the extending portion 354 and the extending portion 1254 described above such that the central axis of the housing 1310 can be maintained at a minimum angle relative to horizontal such that when the extending portion 1354 and the second end 1314 are disposed on a surface and the fluid level within the reservoir decreases to a minimum threshold fluid level, the sealing member 1330 seals with the sealing surface 1322 prior to air flowing into the through-hole 1324 of the sealing member 1320. For example, in some embodiments, a portion of the extending portion 1354 can include a first contact point 1307 and a portion of the lower cap 1309 can include a second contact point 1309 such that, when the assembly 1302 is disposed on a surface (e.g., a horizontal surface), the first contact point 1307 and the second contact point 1309 both contact the surface and the central axis of the through-hole 1324 of the valve seat 1320 and the central axis of the housing 1310 is disposed at at least a minimum angle relative to the horizontal. For example, the first contact point 1307 on the extending portion 1354 can be located on a lower edge of the cap 1350 and the second contact point 1309 can be on a lower edge of the lower cap 1340 coupled to the housing 1310. The first contact point 1307, the second contact point 1309, and the central axis of the housing 1310 can lie in the same plane, and a line running through the first contact point 1307 and the second contact point 1309 can intersect the central axis of the housing 1310 at an angle corresponding to the angle of the central axis of the housing 1310 relative to a surface upon which the assembly 1302 can be disposed when the assembly 1302 is disposed on the surface.

Figure 13B:
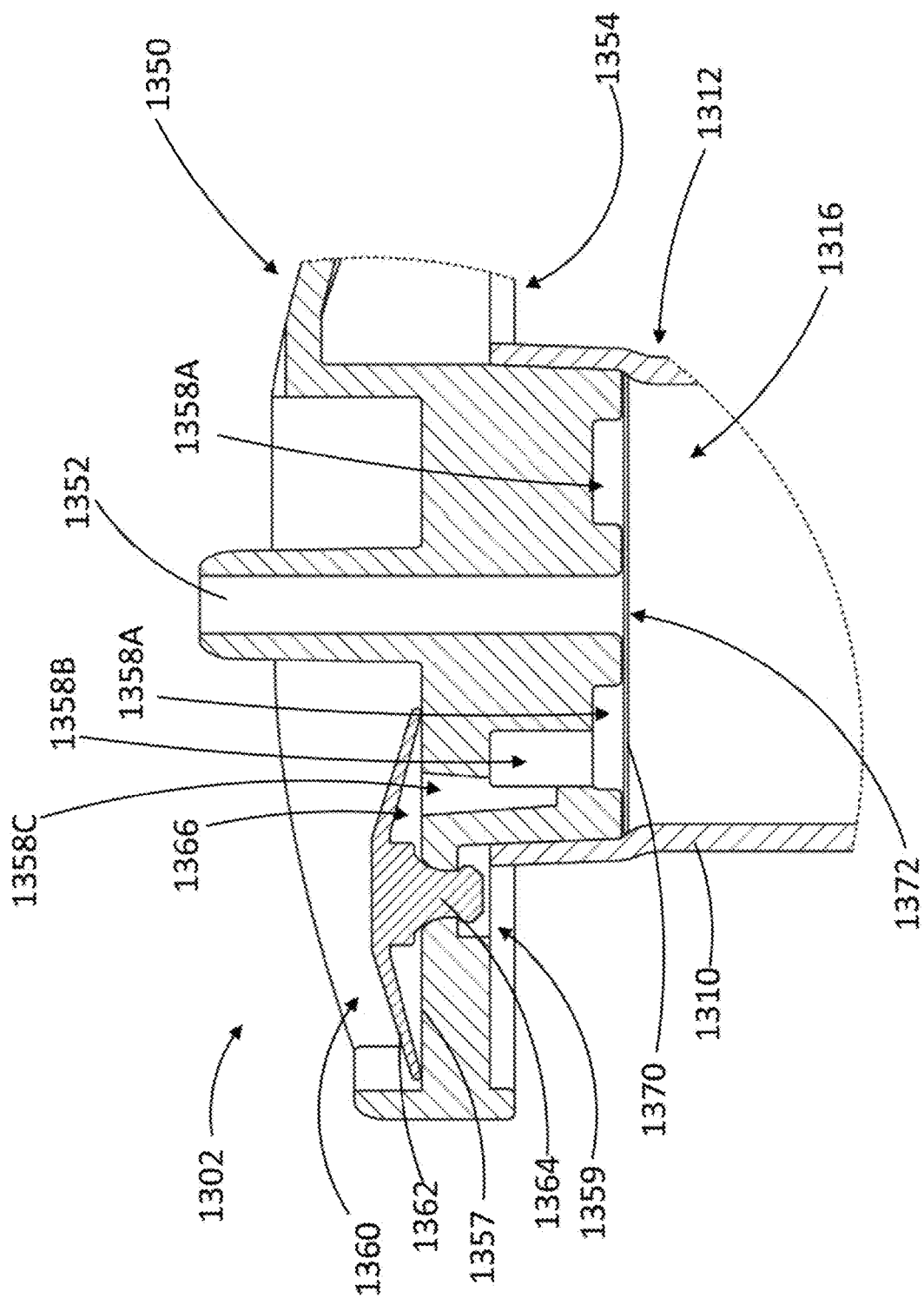
FIG. 13B is a cross-sectional view of a portion of the assembly of FIG. 13A.
Figure 13C:
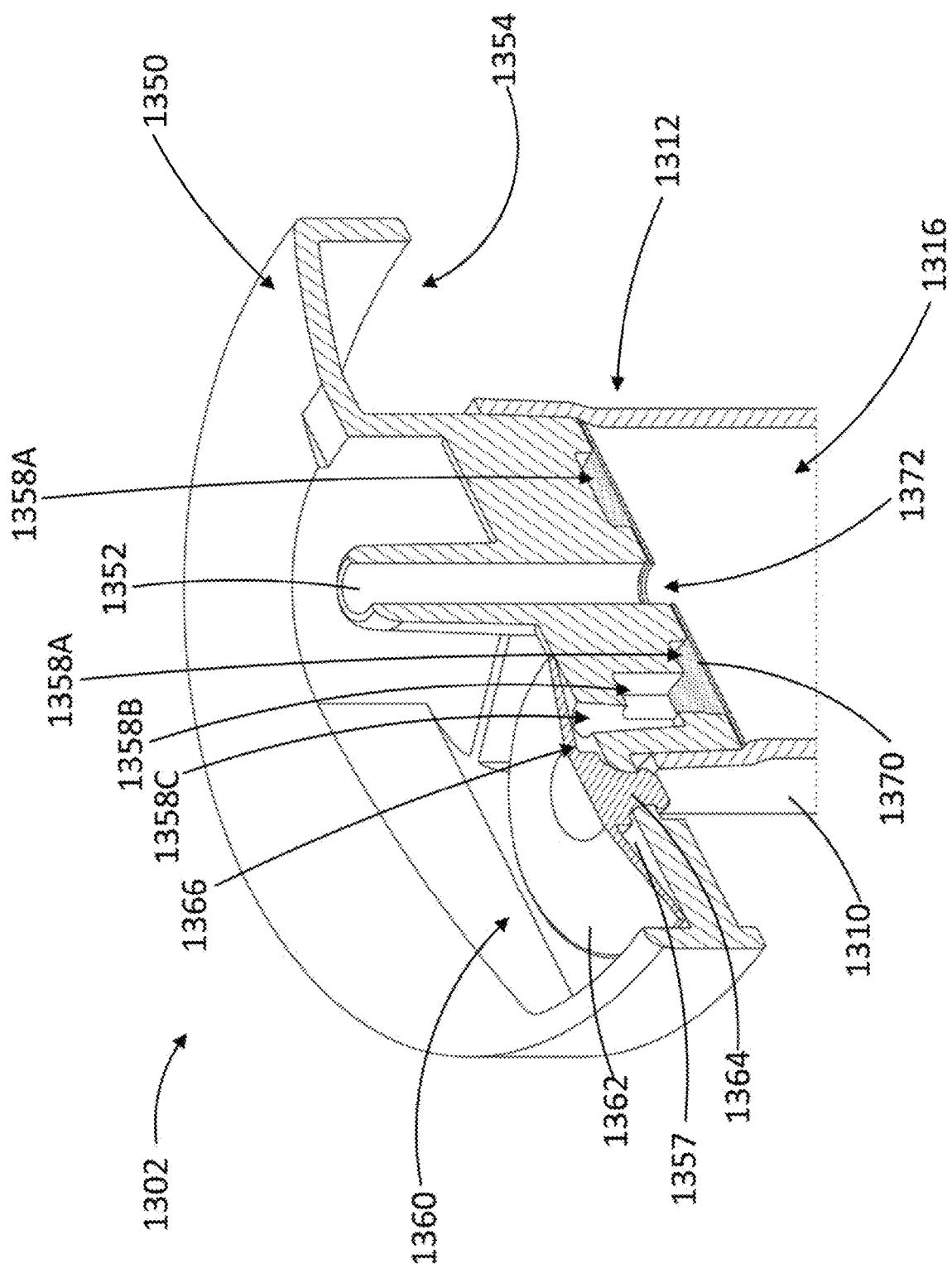
FIG. 13C is a perspective view of a cross-section of the assembly of FIG. 13A.

FIGS. 13B and 13C are a cross-sectional illustration and a perspective view of a cross-section, respectively, of a portion of the assembly 1302. As shown, the cap 1350 can be formed as a monolithic structure and can define a valve recess 1359. The valve 1360 can include an umbrella portion 1362 and a stem portion 1364. The stem portion 1364 can be retained within the valve recess 1359 and the umbrella portion 1362 can be movable relative to a cap sealing surface 1357 of the cap 1350 between a sealed and an unsealed configuration. The cap 1350 can define a first interior space 1358A, a second interior space 1358B, and third interior space 1358C. The first interior space 1358 can, for example, surround the inlet 1352 (which extends to the through-hole 1372 of the hydrophobic filter 1370). The second interior space 1358 can be, for example, cylindrically-shaped and can extend from the first interior space 1358A to the second interior space 1358B. The third interior space can be, for example, conically-shaped, and can extend from the second interior space 1358B to an interior valve space 1366. The interior valve space 1366 can be collectively defined by the umbrella portion 1360 and the cap sealing surface 1357. The umbrella valve 1360 can be configured such that air can pass through the hydrophobic filter 1370, into the first interior space 1358A, into the second interior space 1358B, into the third interior space 1358C, and into the interior valve space 1366. The air in the interior valve space 1366 can build up and apply pressure to the umbrella valve 1360 until the seal between the umbrella portion 1362 and the cap sealing surface 1357 is disrupted such that air can flow out of the interior valve space 1366.

Figure 13D:
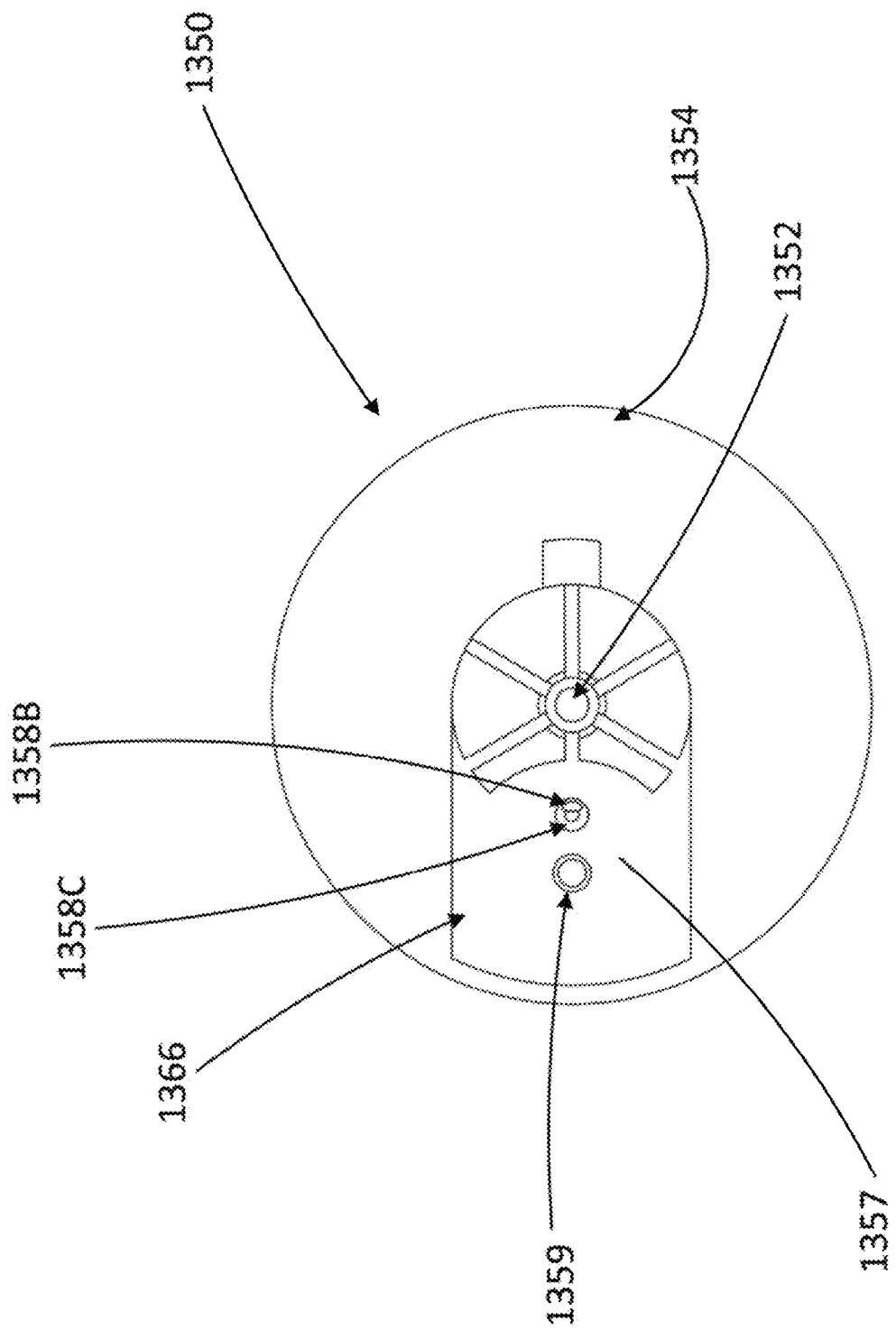
FIG. 13D is a top view of the assembly of FIG. 13A.

As shown in FIGS. 13D and 13E, which are a top view and a perspective view, respectively, of a portion of the cap 1350 with the valve 1360 removed, the cap sealing surface 1357 can be a flat surface without an annular space. Thus, air can flow into the interior valve space 1366 defined in part by the cap sealing surface 1357 via the third interior space 1358C.

Figure 13F:
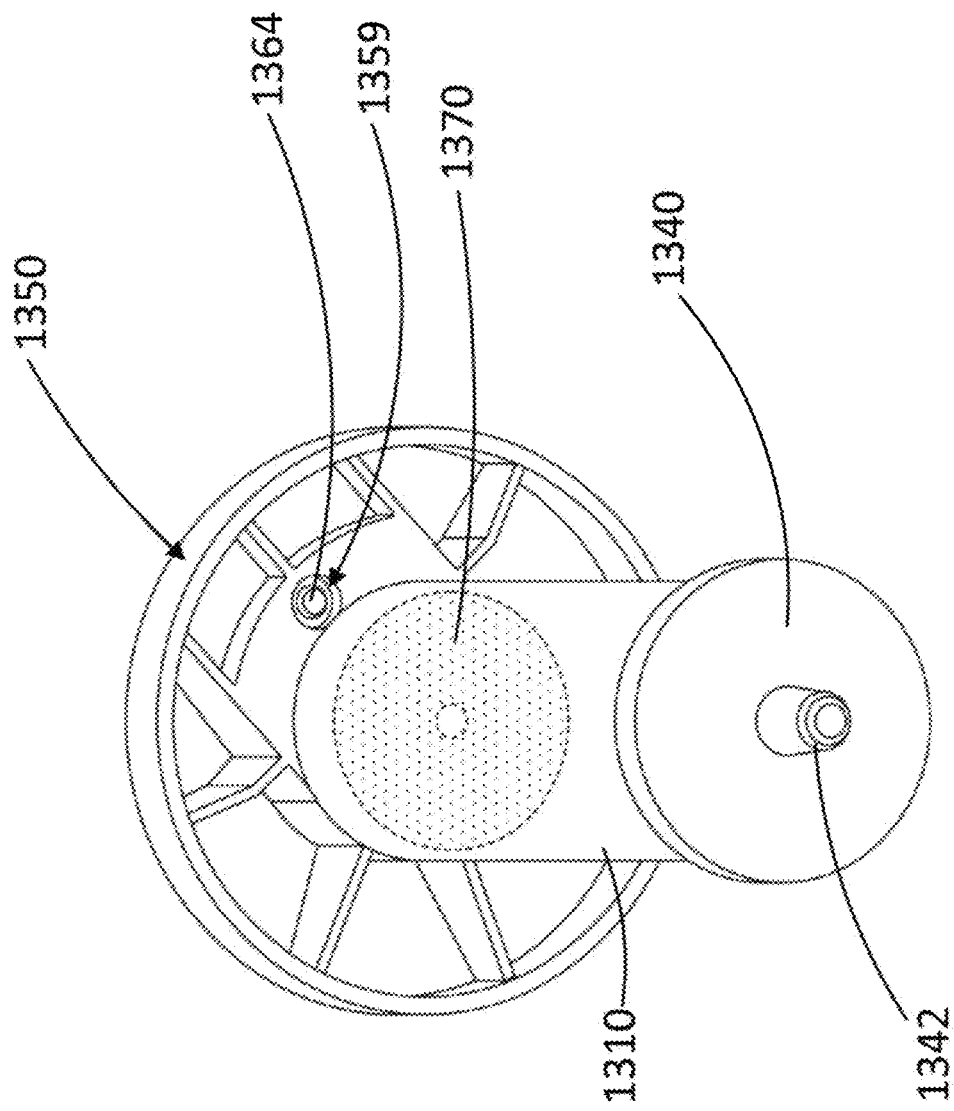
FIG. 13F is a bottom perspective view of the assembly of FIG. 13A.

As shown in FIG. 13F, which is a bottom perspective view of the assembly 1302, the extending portion 1354 of the cap 1350 can extend laterally from the housing 1310 in all directions, forming a brim-shape. Thus, the assembly 1302 can be placed on a surface such that any edge of the lower cap 1340 and any edge of the outer extent of the cap 1350 contact the surface and maintain the central axis of the housing 1310 transverse relative to the surface. Therefore, any portion of the lower cap 1340 and any portion of the cap 1350 lying in the same plane as each other and as the central axis of the housing 1310 can be identified as the first contact point 1307 and the second contact point 1309, respectively.

Figure 13G:
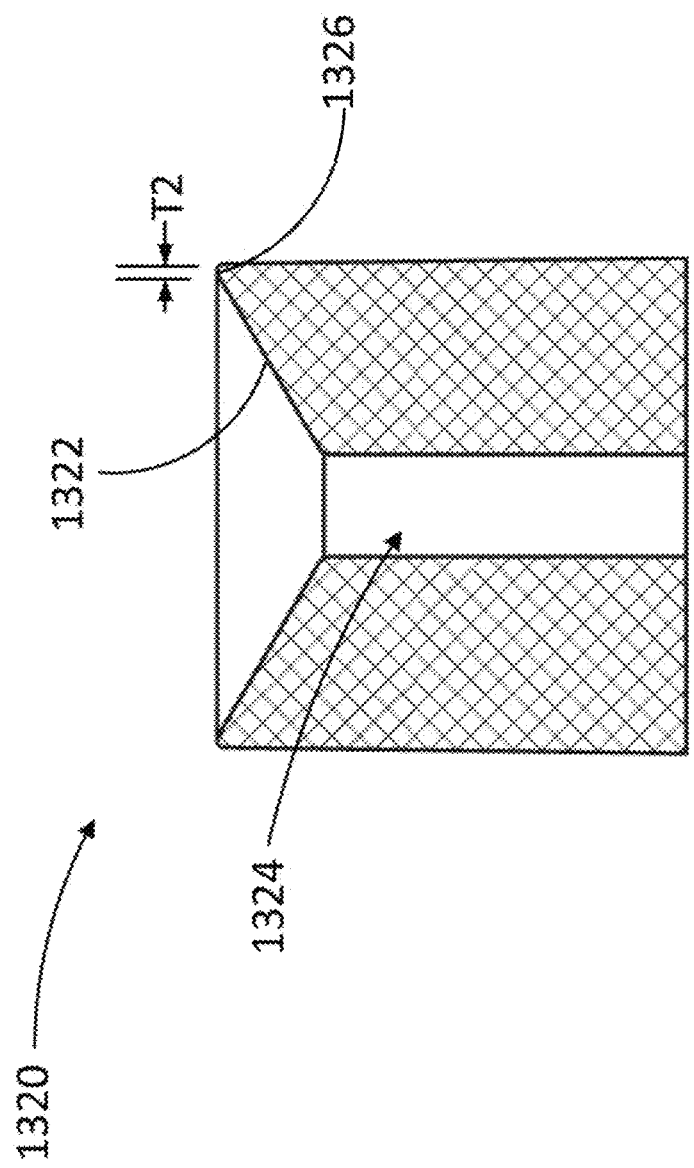
FIG. 13G is a cross-sectional view of a valve seat of the assembly of FIG. 13A.

FIG. 13G is a cross-sectional illustration of the valve seat 1320. As shown in FIG. 13G, the valve seat 1320 can include an upper surface 1326. The upper surface 1326 can be disposed in a plane lying perpendicular to a central axis of the through-hole 1324. The sealing surface 1322 can be disposed at any suitable angle relative to the upper surface 1326 such that the sealing member 1330 can seal with the sealing surface 1322 when a fluid level reaches a threshold minimum fluid level relative to the sealing surface 1322, regardless of whether the housing 1310 is disposed upright (e.g., perpendicular to surface) or transverse relative to a surface. The thickness T2 of the upper surface 1326 of the valve seat 1320 can be sufficiently small such that the sealing member 1330 will not catch on the upper surface 1326 of the valve seat 1320 as the fluid level decreases and the sealing member 1330 approaches the sealing surface 1322.

Figure 14A:
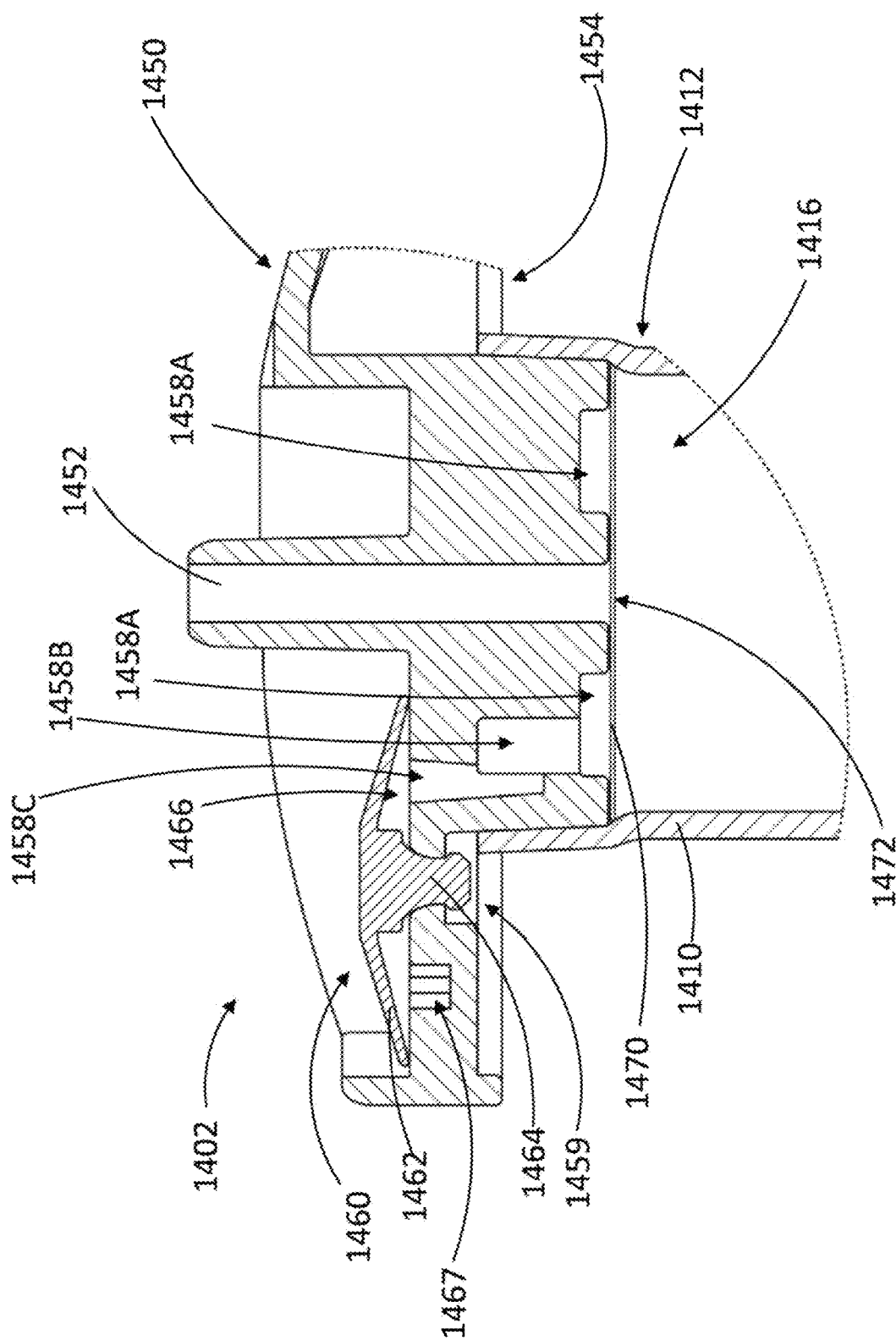
FIG. 14A is a cross-sectional view of a portion of an assembly, according to an embodiment.
Figure 14B:
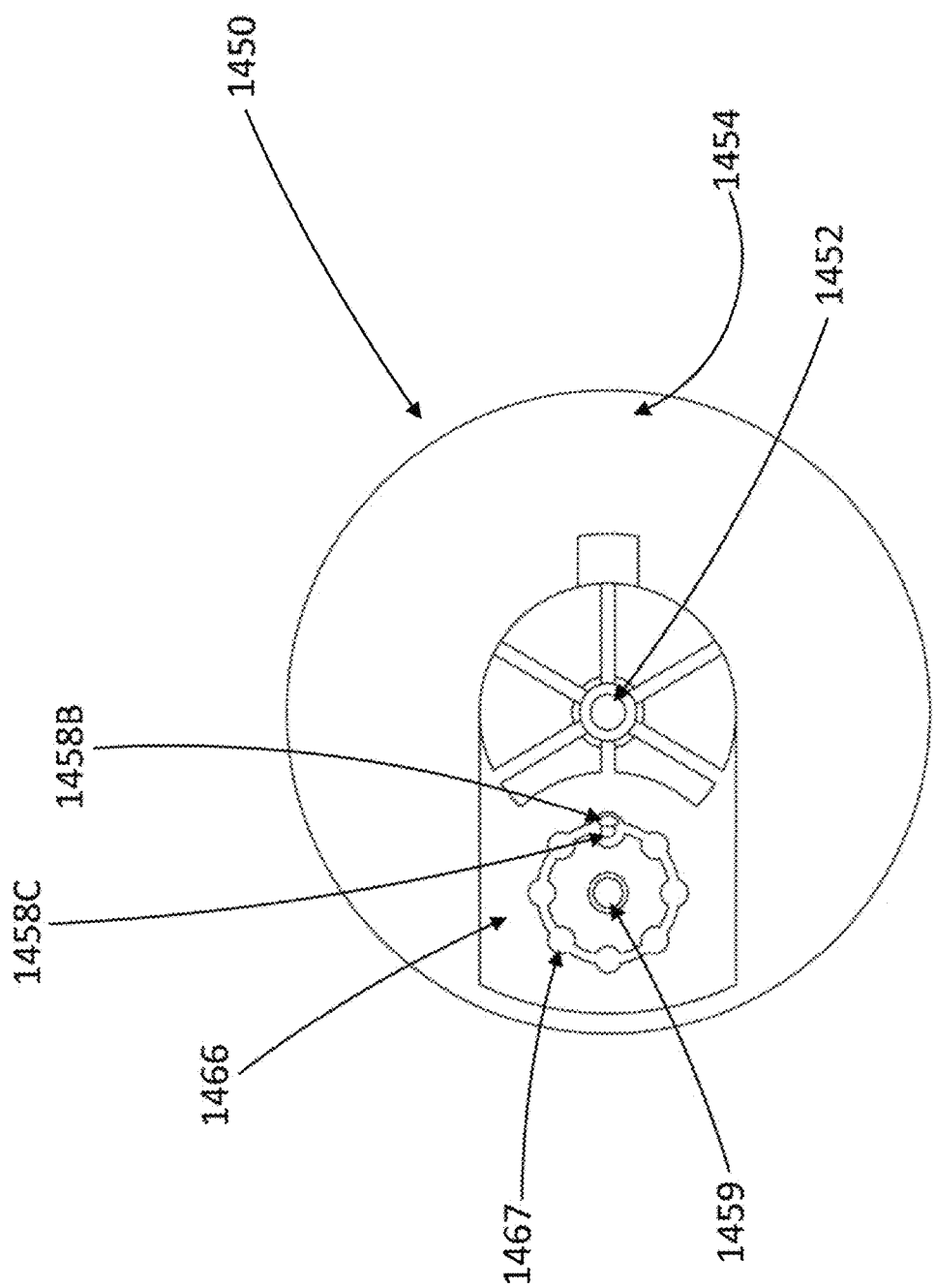
FIG. 14B is a top view of the assembly of FIG. 14A, according to an embodiment.

In some embodiments, an upper cap of an assembly can define three interior regions for air to flow from a reservoir of the assembly to the valve and an annular space to form a portion of a valve interior space. For example, FIGS. 14A and 14B are a cross-sectional view of a portion of an assembly 1402 having a valve 1460 and a top view of a portion of the assembly 1402 with the valve 1460 removed, respectively. The assembly 1402 can be the same or similar in structure and/or function to any of the assemblies described herein. For example, the assembly 1402 can include a housing 1410 and an upper cap 1450. The housing 1410 has a first end 1412 and defines a reservoir 1416. The upper cap 1450 defines an inlet 1452. The upper cap 1450 is sealingly coupled to the housing 1410 and the inlet 1452 can be fluidically coupled to a fluid source (e.g., a fluid source such as the fluid source 180 via tubing such as tubing 104A) such that fluid can be introduced into the reservoir 1416 via the inlet 1452.

The cap 1450 can include a vent 1460 such that fluid, such as air, can exit the reservoir 1416 via the vent 1460. The apparatus 1402 can also include a hydrophobic filter 1470 disposed between the reservoir 1416 and the vent 1460 such that liquid fluid that has been introduced into the reservoir 1416 via the inlet 1452 can be prevented from exiting the reservoir 1416 via the vent 1460. The cap 1450 can also include an extending portion 1454 such that at least a portion of the cap 1450 extends laterally beyond a sidewall of the housing 1410 relative to a central axis of the housing 1410. The extending portion 1454 can be shaped similarly and function in use similarly to the extending portion 354 and the extending portion 1254 described above.

The cap 1450 can be formed as a monolithic structure and can define a valve recess 1459. The valve 1460 can include an umbrella portion 1462 and a stem portion 1464. The stem portion 1464 can be retained within the valve recess 1459 and the umbrella portion 1462 can be movable relative to a cap sealing surface 1457 of the cap 1450 between a sealed and an unsealed configuration. The cap 1450 can define a first interior space 1458A, a second interior space 1458B, and third interior space 1458C. The first interior space 1458 can, for example, surround the inlet 1452 (which extends to the through-hole 1472 of the hydrophobic filter 1470). The second interior space 1458 can be, for example, cylindrically-shaped and can extend from the first interior space 1458A to the second interior space 1458B. The third interior space can be, for example, conically-shaped, and can extend from the second interior space 1458B to an interior valve space 1466. The interior valve space 1466 can be collectively defined by the umbrella portion 1460 and the cap 1450 (e.g., the cap sealing surface 1457 and an annular space 1467 defined by the cap 1450). The annular space 1467 can be the same or similar in structure and/or function to the annular space 1267 described above. The umbrella valve 1460 can be configured such that air can pass through the hydrophobic filter 1470, into the first interior space 1458A, into the second interior space 1458B, into the third interior space 1458C, and into the interior valve space 1466. The air in the interior valve space 1466 can build up and apply pressure to the umbrella valve 1460 until the seal between the umbrella portion 1462 and the cap sealing surface 1457 is disrupted such that air can flow out of the interior valve space 1466.

FIGS. 15A-15L are cross-sectional illustrations of a portion of a system 1500 during various stages of use. The system 1500 can be the same or similar in structure and/or function to any of the systems described herein. The system 1500 can include an assembly 1502, which can be the same or similar in structure and/or function to any of the assemblies described herein. For example, the assembly 1502 can include a housing 1510, an upper cap 1550, and a lower cap 1540. The assembly 1502 can also include a sealing member 1530 and a valve seat 1520 disposed within the housing 1510. The housing 1510 has a first end 1512 opposite the second end 1514 and defines a reservoir 1516. The upper cap 1550 defines an inlet 1552. The upper cap 1550 is sealingly coupled to the housing 1510 and the inlet 1552 can be fluidically coupled to a fluid source via tubing 1504A (e.g., a fluid source such as the fluid source 180) such that fluid can be introduced into the reservoir 1516 via the inlet 1552. The lower cap 1540 can include an outlet 1542 and can be coupled to the second end 1514 of the housing 1510. The valve seat 1520 can be coupled to a barb of the lower cap 1540. The outlet 1542 can be fluidically coupled to a negative pressure source via tubing 1504B such that fluid can flow toward the negative pressure source from the reservoir 1516 via a lumen defined by the outlet 1542. The sealing member 1530 can be configured to seal with a sealing surface 1522 of the valve seat 1520. The valve seat 1520 can define a through-hole 1524 and be disposed relative to the outlet 1542 such that fluid can flow from the reservoir 1516 to the outlet 1542 via the through-hole 1524 of the valve seat 1520.

The valve seat 1520 and the sealing member 1530 can be configured to allow liquid fluid to flow from the reservoir 1516 into the outlet 1542 when the liquid fluid level or volume within the reservoir 1516 is above a minimum threshold fluid level or volume, and to prevent the flow of fluid from the reservoir 1516 through the outlet 1542 when the liquid fluid level or volume within the reservoir 1516 is at or below a minimum threshold fluid level or volume, thus preventing air from flowing into the outlet 1542. For example, the sealing member 1530 can be configured to sealingly engage with the valve seat 1520 such that the sealing member 1530 obstructs the through-hole 1524. The valve seat 1520 and the sealing member 1530 can be configured to remain sealingly engaged such that the reservoir 1516 is fluidically isolated from the outlet 1542 after fluid has been added to the reservoir 1516 such that the fluid level is above the minimum threshold fluid level until the seal between the sealing member 1530 and the valve seat 1520 is manually disrupted via squeezing and deforming the housing 1510 and the valve seat 1520.

The cap 1550 can include a vent 1560 such that fluid, such as air, can exit the reservoir 1516 via the vent 1560. The assembly 1502 can also include a hydrophobic filter 1570 disposed between the reservoir 1516 and the vent 1560 such that liquid fluid that has been introduced into the reservoir 1516 via the inlet 1552 can be prevented from exiting the reservoir 1516 via the vent 1560. The cap 1550 can also include an extending portion 1554 such that at least a portion of the cap 1550 extends laterally beyond a sidewall of the housing 1510 relative to a central axis of the housing 1510. The extending portion 1554 can be shaped similarly and function in use similarly to the extending portion 354 and the extending portion 1254 described above such that the central axis of the housing 1510 can be maintained at a minimum angle relative to horizontal when the extending portion 1554 and the second end 1514 are disposed in contact with a surface such that, when the fluid level within the reservoir decreases to a minimum threshold fluid level, the sealing member 1530 seals with the sealing surface 1522 prior to air flowing into the through-hole 1524 of the sealing member 1520. For example, in some embodiments, a portion of the extending portion 1554 can include a first contact point 1507 and a portion of the lower cap 1509 can include a second contact point 1509 such that, when the assembly 1502 is disposed on a surface (e.g., a horizontal surface), the first contact point 1507 and the second contact point 1509 both contact the surface and the central axis of the through-hole 1524 of the valve seat 1520 and the central axis of the housing 1510 is disposed at at least a minimum angle relative to the surface. For example, the first contact point 1507 on the extending portion 1554 can be located on a lower edge of the cap 1550 and the second contact point 1509 can be on a lower edge of the lower cap 1540 coupled to the housing 1510. The first contact point 1507, the second contact point 1509, and the central axis of the housing 1510 can lie in the same plane, and a line running through the first contact point 1507 and the second contact point 1509 can intersect the central axis of the housing 1510 at an angle corresponding to the angle of the central axis of the housing 1510 relative to a surface upon which the assembly 1502 can be disposed when the assembly 1502 is disposed on the surface.

In use, the sealing member 1530 can float near the top of the reservoir 1516 when the reservoir 1516 is full of liquid fluid and the fluid line FL is near the top of the reservoir 1516. As liquid fluid is drawn from the reservoir 1516 and into the tube 1504B via the through-hole 1524 of the valve seat 1520 and the outlet 1542, additional fluid is drawn due to negative pressure applied by the negative pressure source and/or can flow due to gravity into the reservoir 1516 from the fluid source via the tube 1504A and the inlet 1552. In some embodiments, the negative pressure can be applied cyclically or periodically such that a volume of fluid less than the volume of the reservoir 1516 is drawn through the outlet 1516 during each cycle or period (e.g., during each stroke of a syringe coupled to the tube 1504B).

Figure 15A:
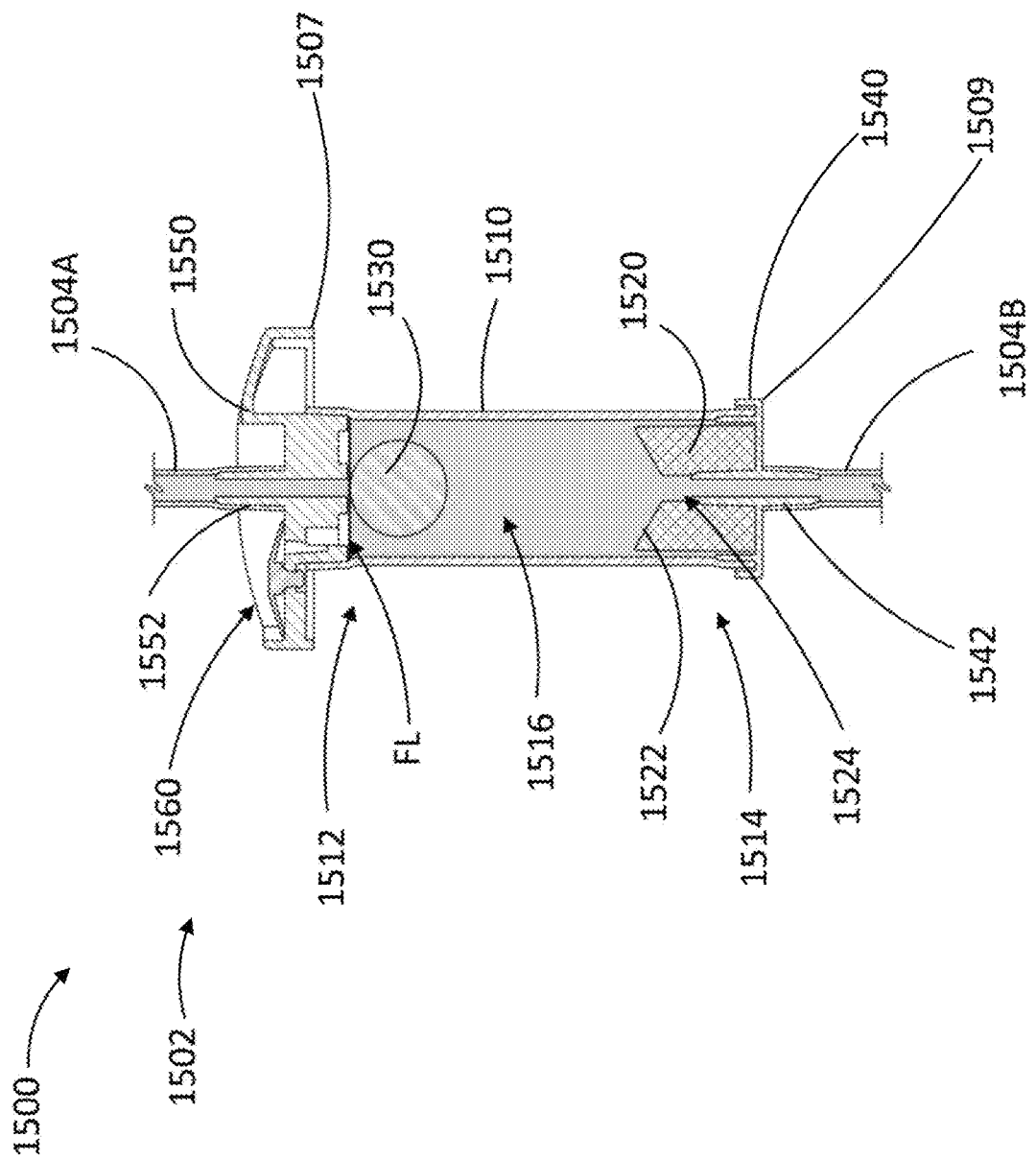
Figure 15B:
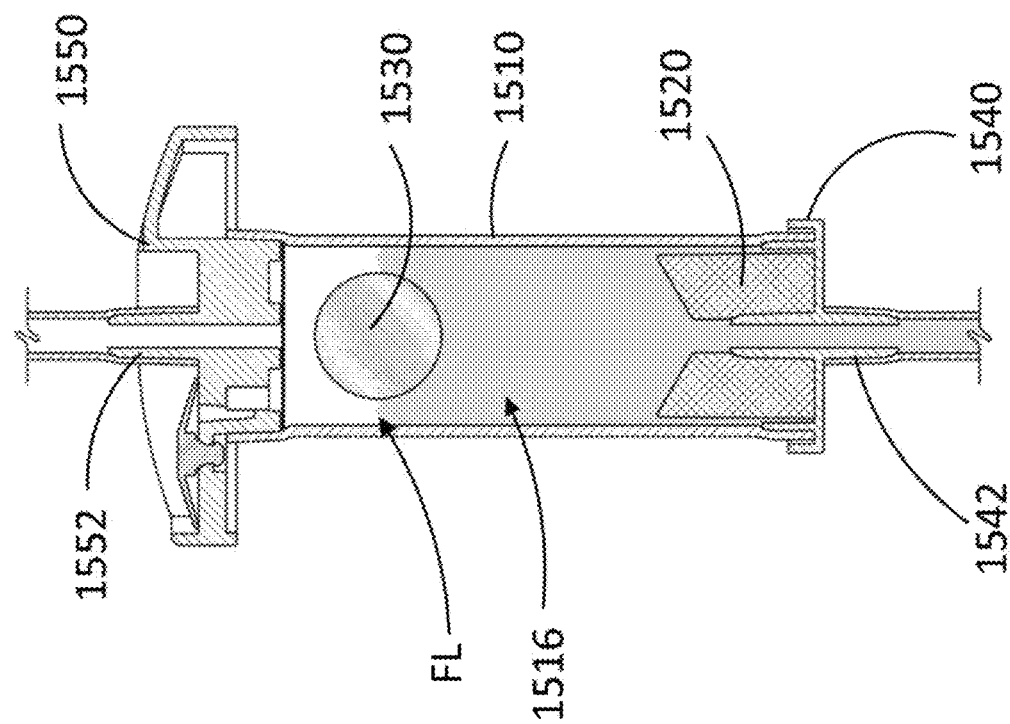
Figure 15C:
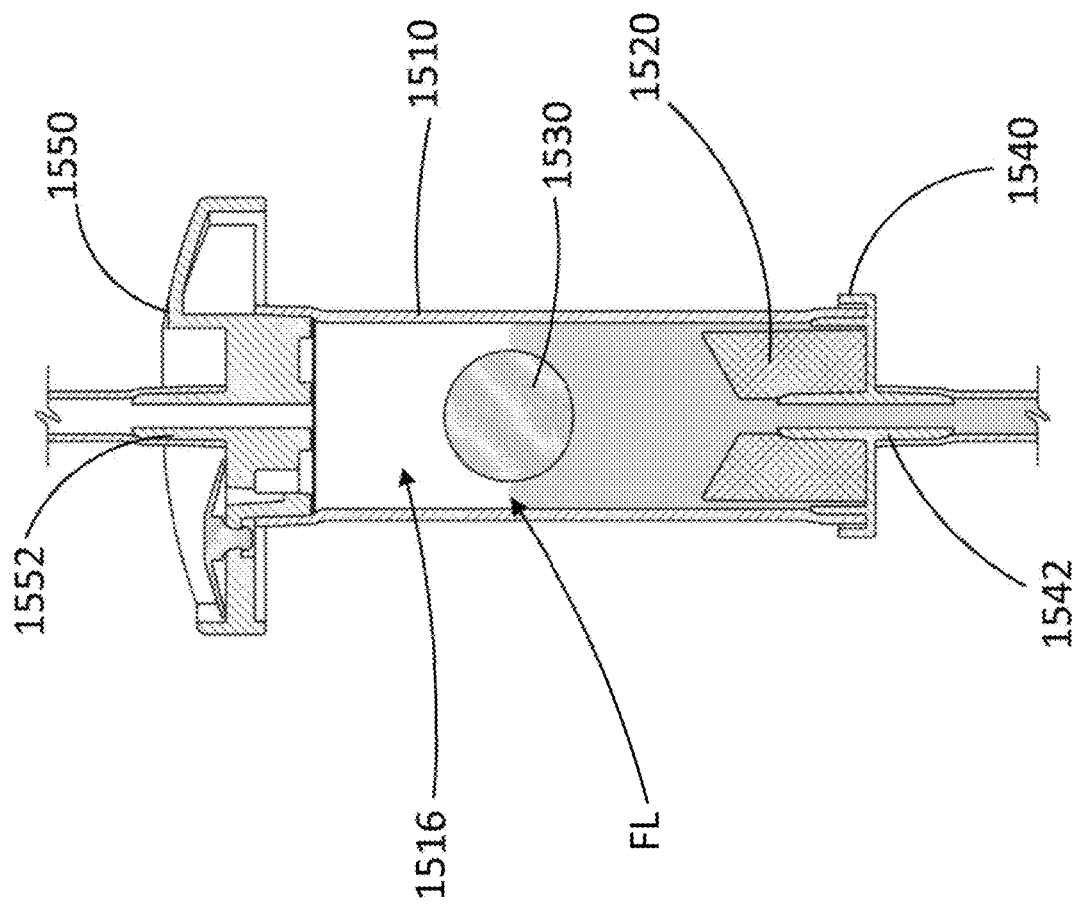
Figure 15D:
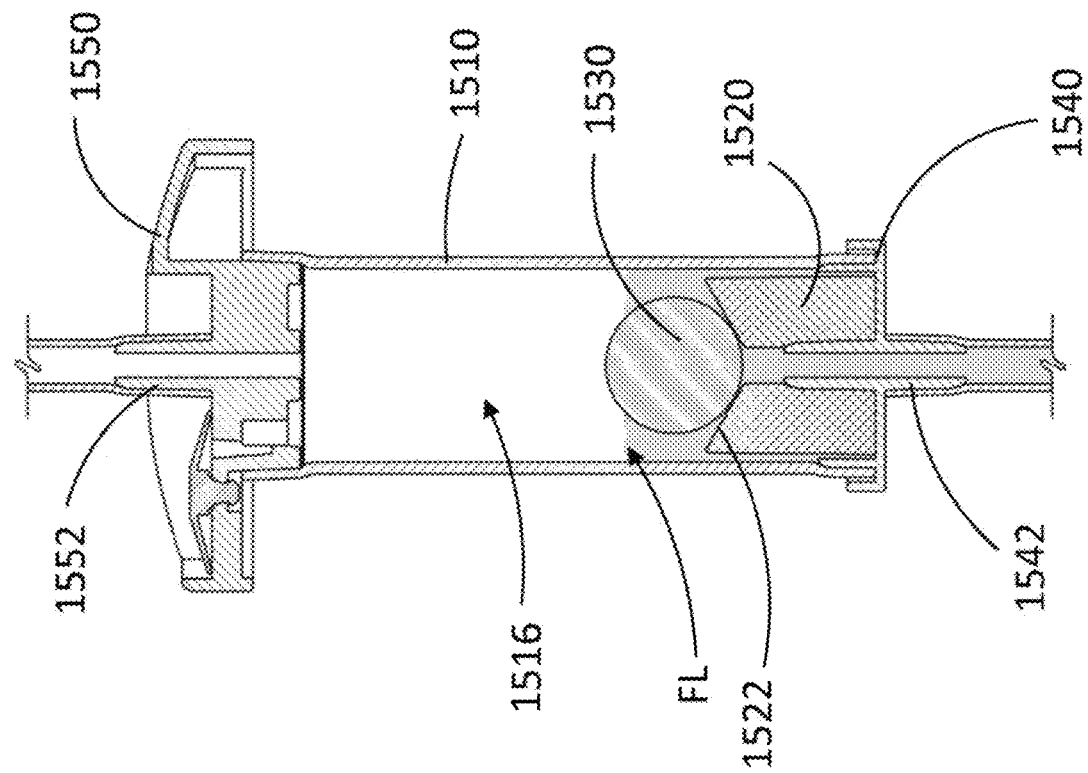

As shown in FIGS. 15B-15D, when substantially all of the fluid contained in the fluid source has been transferred into the reservoir 1516 such that the fluid source is substantially empty (or the fluid source has been moved to a vertical position below the inlet 1552 of the assembly 1502 such that liquid fluid flow into the reservoir 1516 ceases), the volume of liquid fluid in the reservoir 1516 will progressively decrease and the fluid line FL will move toward the outlet 1542 of the assembly 1502 as fluid continues to be drawn through the outlet 1542 by the negative pressure source. As the fluid line FL moves toward the outlet 1542, the sealing member 1530 will also move toward the outlet 1542. For example, if the negative pressure source draws a particular volume of fluid through the outlet 1542 with each cycle of the negative pressure source, the fluid line FL can drop progressively (with alternating fluid transfer and static periods) as shown in FIGS. 15B-15D with each cycle. If the fluid source includes any air that was not removed during an initial purging process, the air can travel through the tubing 1504A, through the inlet 1552, into the reservoir 1516, through the hydrophobic filter 1570, and out of the vent 1560. As the fluid level FL decreases, the sealing member 1530 can move toward the valve seat 1520.

As shown in FIG. 15D, when the fluid level reaches the minimum fluid threshold, the sealing member 1530 can sealingly engage with the valve seat 1520, fluidically isolating the reservoir 1516 from the through-hole 1524 of the valve seat 1520 and the outlet 1542. If the negative pressure source is mid-way though a drawing cycle or period, the sealing of the sealing member 1530 with the valve seat 1520 can cause a drawing mechanism (e.g., a plunger within a syringe) to cease moving (e.g., due to the isolation of fluid flow causing a negative pressure to build in the tubing 1504B downstream of the sealing member 1530). When the sealing member 1530 is sealingly engaged with the valve seat 1520, a static column of fluid can be maintained within the through-hole of the valve seat 1520, the outlet 1542, and the tubing 1504B. With the sealing member 1530 sealingly coupled to the valve seat 1520, the fluid source can be separated from the tubing 1504A. A second fluid source (e.g., a second saline bag) can then be coupled to the tubing 1504A.

For example, with the sealing member 1530 sealingly engaged with the valve seat 1520, a second end of the tubing 1504A can be coupled to a second fluid source. For example, the second end of the tubing 1504A can include a spike and the second fluid source can be a saline fluid bag having an outlet, and the spike can be coupled to the outlet of the saline fluid bag such that the saline fluid bag is fluidically coupled to the reservoir 1516 via the tubing 1504A and the inlet 1552. The saline fluid bag can then be squeeze purged to remove excess air. For example, the air can be removed from the system 1500 by inverting the saline fluid bag such that the outlet is disposed at the top of the saline fluid bag and such that, when the user squeezes the bag, air within the saline fluid bag can flow through the tubing 1504A, into the reservoir 1516, through the hydrophobic filter 1570, and out of the vent 1560. When most or all of the air has been removed from the saline fluid bag, the fluid bag can be reoriented such that the outlet is disposed at the bottom of the saline fluid bag. The saline fluid bag can be raised to a height higher than the assembly 1502 such that liquid fluid flows through the tubing 1504A and the inlet 1552 into the reservoir 1516 based, at least in part, on gravitational forces. The saline fluid bag can also be squeezed by the user to force fluid into the reservoir 1516.

Figure 15E:
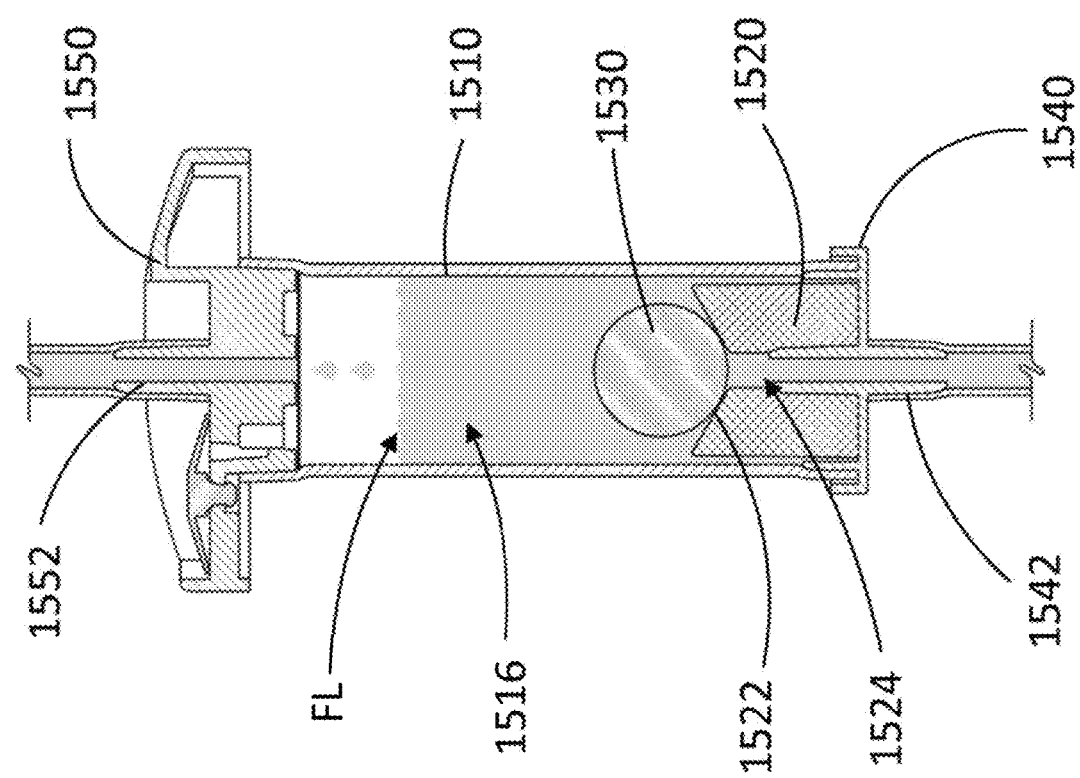
Figure 15F:
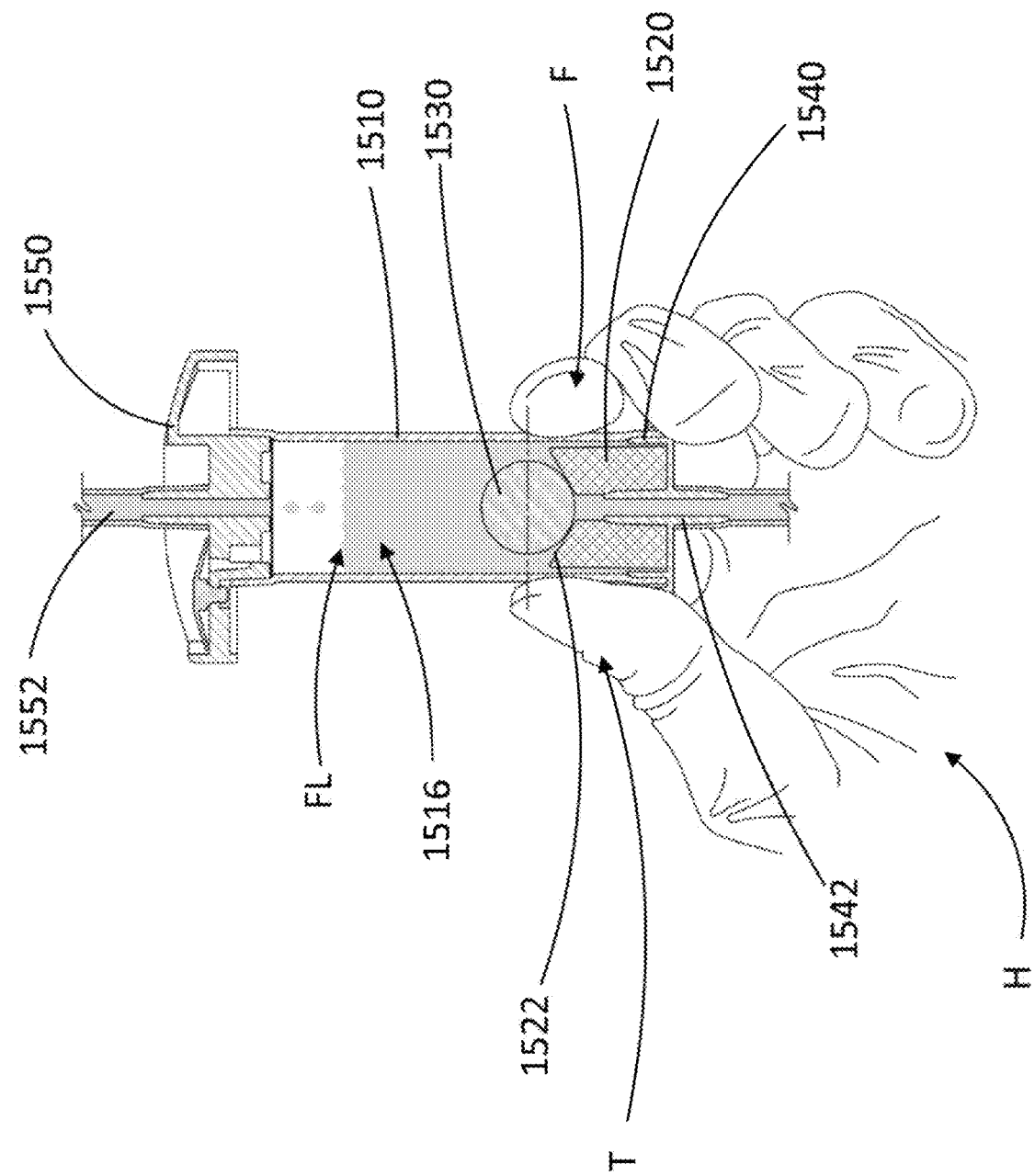
Figure 15G:
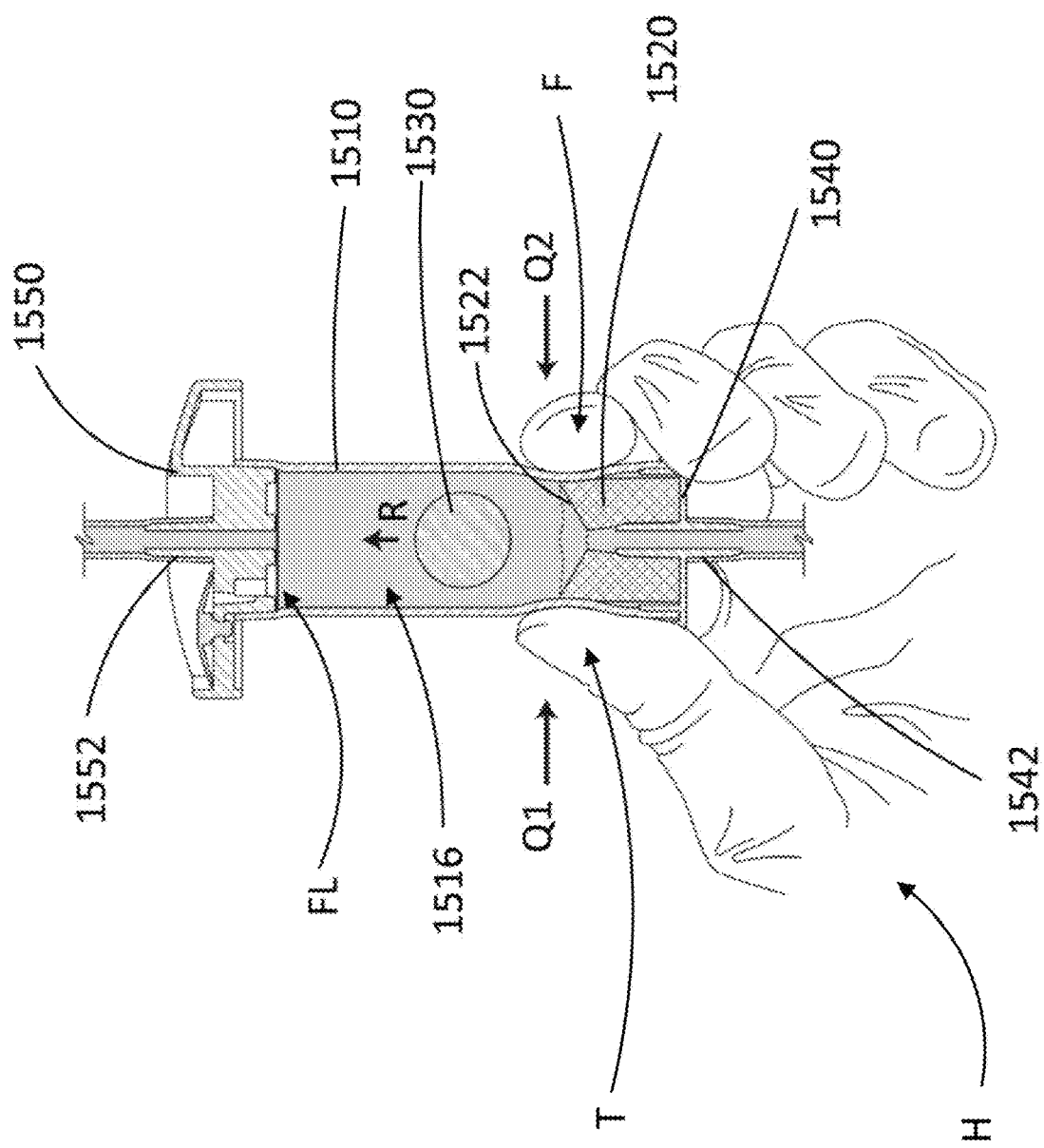

As shown in FIG. 15E, due at least in part to the negative pressure applied to the sealing member 1530 by the negative pressure source and/or static column of fluid maintained within the through-hole of the valve seat 1520, the outlet 1542, and the tubing 1504B, the sealing member 1530 can remain sealed with the valve seat 1520 as the fluid level FL rises above the minimum threshold fluid level. In other words, the downward force applied to the sealing member 1530 by the application of the negative gauge pressure to the portion of the sealing member 1530 that is radially inward from the circular sealing contact region (i.e., sealing interface) with the valve seat 1520 is greater than the buoyant force produced by the difference in density between the sealing member 1530 and the fluid. As shown in FIGS. 15F and 15G, when the fluid level in the reservoir 1516 is at least higher than a minimum threshold fluid level (e.g., when the reservoir 1516 is full of liquid), the user can apply a force to a portion of the outer surface of the housing 1510 between the bottom of the housing 1510 and the center of the sealing member 1530 such that the valve seat 1520 is deformed and the seal is broken between the sealing member 1530 and the valve seat 1520. For example, a thumb T and a finger F of a user's hand H can be oppositely disposed relative to the housing 1510 and squeezed toward each other, applying oppositely directed forces Q1 and Q2 to the housing 1510 and the valve seat 1520 such that the valve seat 1520 is deformed. Deforming the sealing surface 1522 breaks the seal between the sealing member 1530 and the sealing surface 1522, eliminating the downward force applied by the negative gauge pressure, releasing the sealing member 1530 such that the buoyant force on the sealing member 1530 lifts the sealing member 1530 free from the sealing surface 1522, and the sealing member 1530 can then float upwardly in the direction R to the fluid level FL.

Figure 15H:
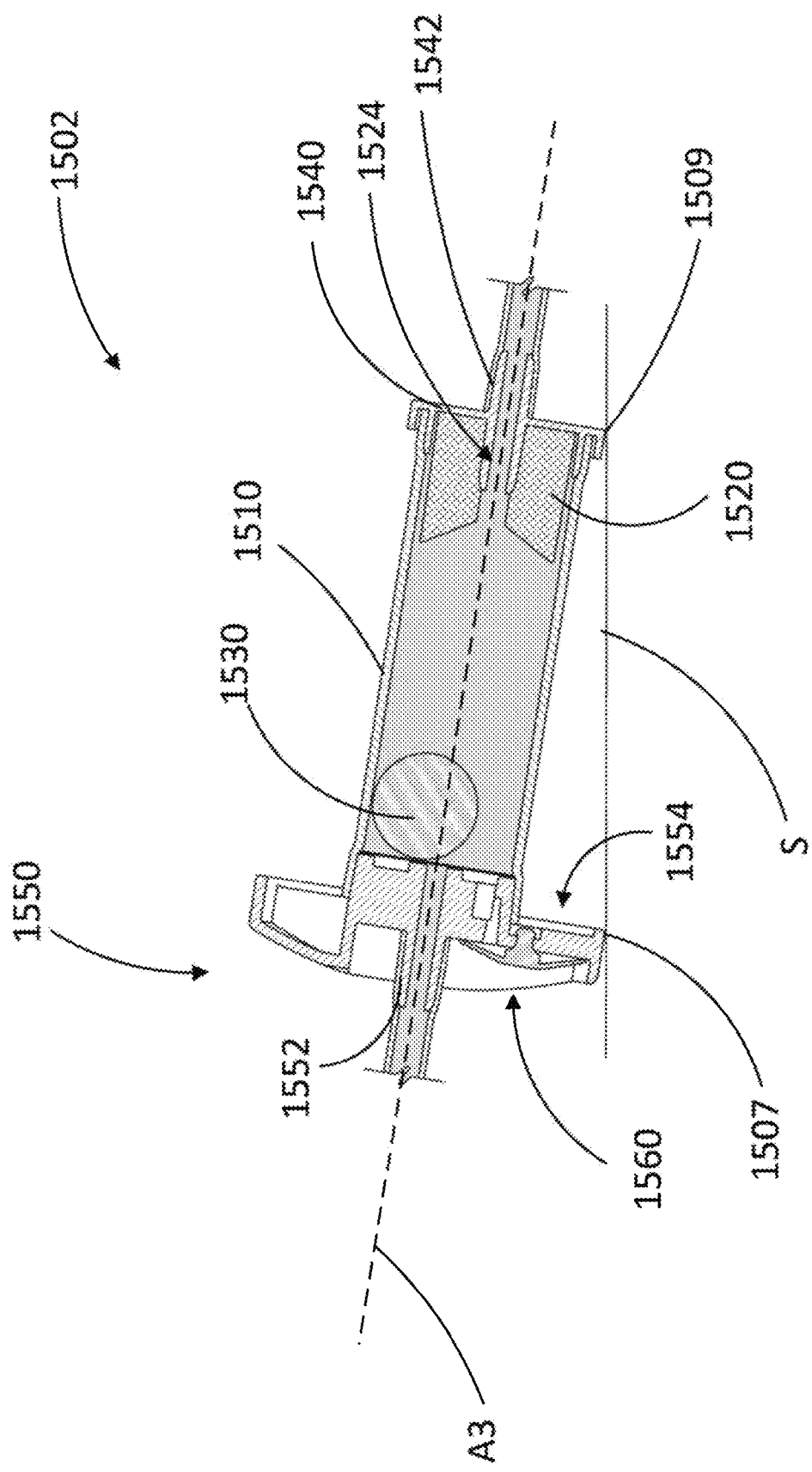

As shown in FIG. 15H, in some embodiments, during the portion of operation in which the sealing member 1530 is floating at or near the fluid line FL and not sealed with the valve seat 1520 and in which fluid is being drawn from the reservoir 1516 into the tubing 1504B by the negative pressure source, the assembly 1502 may be disposed on a surface S such that the assembly 1502 is not vertically-oriented (e.g., the central axis A3 of the housing 1510 and the through-hole 1524 is not vertically-oriented). For example, the assembly 1502 may be placed or inadvertently fall onto a surface S (e.g., a patient's bed) such that the assembly 1502 is disposed with the upper cap 1550 and the lower cap 1540 in contact with the surface S supporting the assembly 1502 and with the central axis A3 at an angle transverse to the horizontal. In such embodiments, the extending portion 1554 of the upper cap 1550 can maintain the assembly 1502 in an orientation relative to the surface S, and thus to the horizontal, such that the sealing member 1530 will still sealingly engage with the valve seat 1520 when the fluid level FL drops below a minimum threshold level. For example, the extending portion 1554 of the upper cap 1550 can include a first contact point 1507 and the lower cap 1540 can include a second contact point 1509, the first contact point 1507 and the second contact point 1509 being in the same plane as the central axis A3. When the first contact point 1507 and the second contact point 1509 are in contact with the surface S, the central axis A3 can be maintained transverse to the surface S and, depending on the angle of the surface S to the horizontal, the central axis A3 can be maintained transverse to the horizontal. The angle between the central axis A3 and the surface S, and to the horizontal, can be sufficiently large such that the sealing member 1530 can still reliably sealingly engage with the valve seat 1520 when the fluid level FL drops below a minimum threshold level.

For example, as shown in FIGS. 15I-K, when substantially all of the fluid contained in the fluid source has been transferred into the reservoir 1516 such that the fluid source is substantially empty (or the fluid source has been moved to a vertical position below the inlet 1552 of the assembly 1502 such that liquid fluid flow into the reservoir 1516 ceases), the volume of liquid fluid in the reservoir 1516 will progressively decrease and the fluid line FL will move toward the surface S and the outlet 1542 of the assembly 1502 as fluid continues to be drawn through the outlet 1542 by the negative pressure source. As the fluid line FL moves toward the outlet 1542, the sealing member 1530 will also move toward the outlet 1542. For example, if the negative pressure source draws a particular volume of fluid through the outlet 1542 with each cycle of the negative pressure source, the fluid line FL can drop progressively (with alternating fluid transfer and static periods) as shown in FIGS. 15I-15K with each cycle. If the fluid source includes any air that was not removed during an initial purging process, the air can travel through the tubing 1504A, through the inlet 1552, into the reservoir 1516, through the hydrophobic filter 1570, and out of the vent 1560. As the fluid level FL decreases, the sealing member 1530 can move toward the valve seat 1520. In some embodiments, the negative pressure applied to the fluid in the reservoir 1516 by the negative pressure source can urge the sealing member 1530 into engagement with the sealing surface 1522 of the valve seat 1520 by creating a fluid flow path form the reservoir 1516 into the through-hole 1524.

Figure 15L:
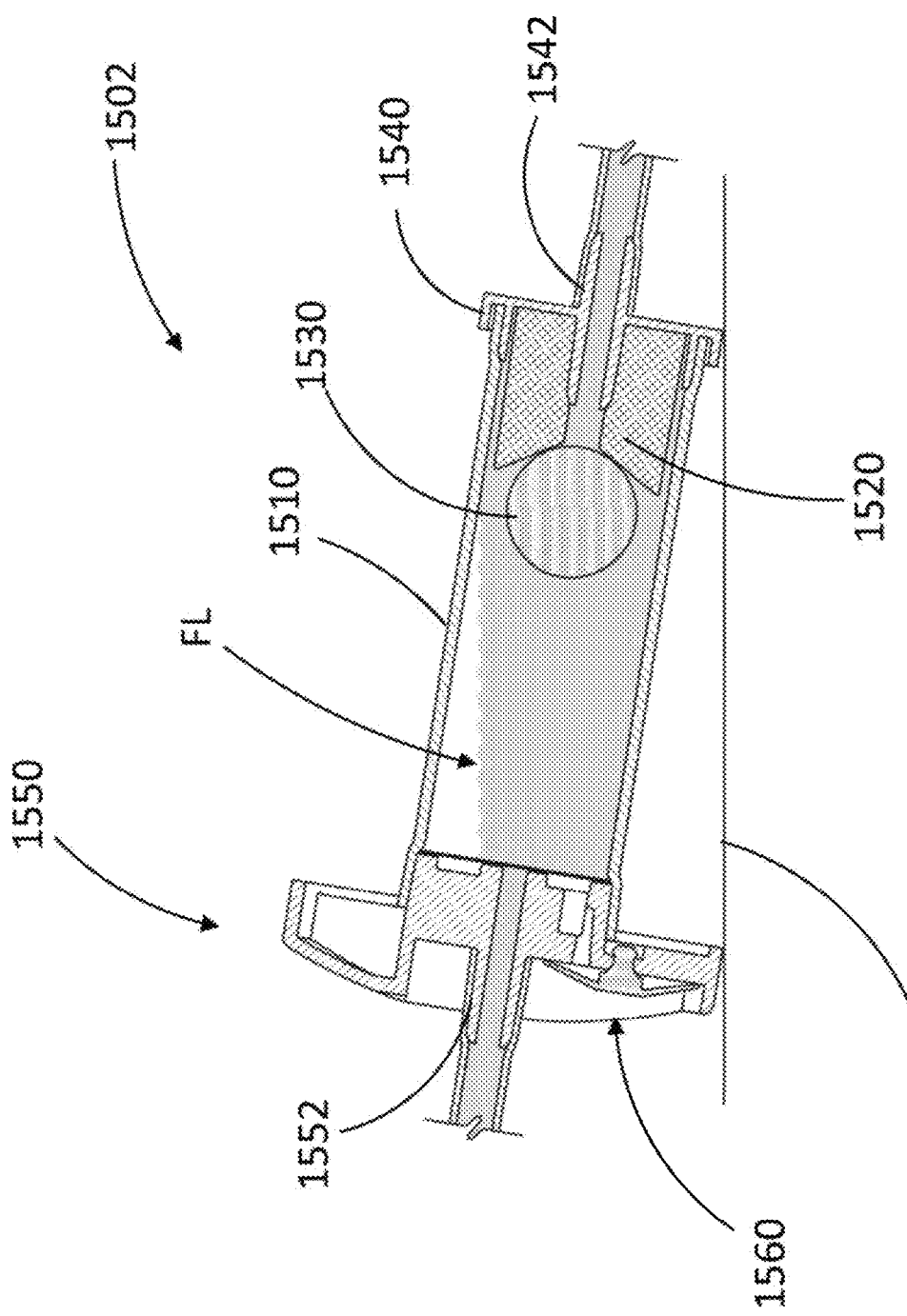

As described above, the minimum threshold level when the assembly 1502 is disposed on the surface S with the upper cap 1550 and the lower cap 1540 in contact with the surface S may be different from the minimum threshold level when the assembly 1502 is vertically-oriented. For example, the sealing member 1530 may sealingly engaged with the valve seat 1520 when more fluid is remaining in the reservoir 1516 when the assembly 1502 is disposed on the surface than when the assembly 1502 is vertically-oriented (e.g., hanging). As shown in FIG. 15K, the sealing member 1530 can sealingly engage with the valve seat 1540 when the assembly 1502 is disposed on surface S similarly to when the assembly 1502 is vertically-oriented (e.g., as shown in FIG. 15D). With the sealing member 1530 sealingly engaged with the valve seat 1520 and the reservoir 1516 fluidically isolated from the outlet 1542, the empty fluid source can be replaced with a second fluid source via the process as described above with reference to FIGS. 15E-15G). When the reservoir 1516 has been filled with liquid fluid from the second fluid source such that the fluid line FL is above the minimum threshold level, as shown in FIG. 15L, the valve seat can be deformed to release the sealing member 1530 as described above (e.g., via squeezing the housing 1510 below the center of the sealing member 1530) and fluid can continue to be drawn through the outlet 1542 by the negative pressure source.

In some embodiments, the fluid source (e.g., a saline fluid bag) can be maintained at a height higher than the assembly 1502 such that liquid fluid flows through the tubing 1504A and the inlet 152 into the reservoir 116 based, at least in part, on gravitational forces. In some embodiments, the fluid source (e.g., a saline fluid bag) can be disposed lower than or even to the assembly 1502 (e.g., on a surface such as a patient bed), and liquid fluid can be drawn through the tubing 1504A and the inlet 152 into the reservoir 116 based, at least in part, on negative pressure applied to the fluid source by the negative pressure source via the reservoir 1516.

Figure 16A:
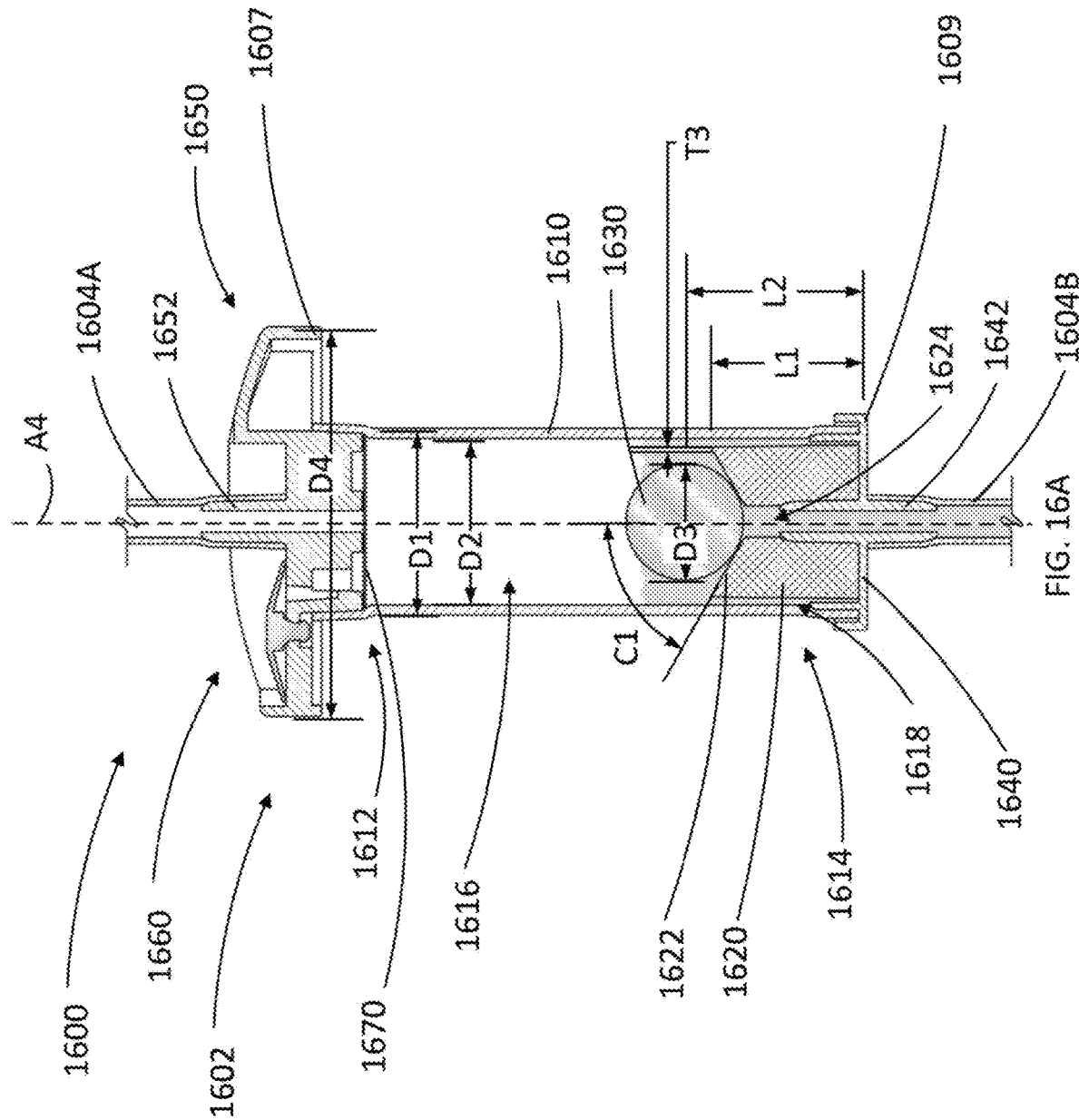

FIGS. 16A and 16B are cross-sectional illustrations of a system 1600 including an assembly 1602 illustrating various exemplary dimensions and relationships between components of the assembly 1602. The system 1600 can be the same or similar in structure and/or function to any of the systems described herein, such as the system 1500. The assembly 1602 can be the same or similar in structure and/or function to any of the assemblies described herein, such as the assembly 1502. For example, the assembly 1602 can include a housing 1610, an upper cap 1650, and a lower cap 1640. The assembly 1602 can also include a sealing member 1630 and a valve seat 1620 disposed within the housing 1610. The housing 1610 has a first end 1612 opposite the second end 1614 and defines a reservoir 1616. The upper cap 1650 defines an inlet 1652. The upper cap 1650 is sealingly coupled to the housing 1610 and the inlet 1652 can be fluidically coupled to a fluid source via tubing 1604A (e.g., a fluid source such as the fluid source 180) such that fluid can be introduced into the reservoir 1616 via the inlet 1652. The lower cap 1640 can include an outlet 1642 and can be coupled to the second end 1614 of the housing 1610. The valve seat 1620 can be coupled to a barb of the lower cap 1640. The outlet 1642 can be fluidically coupled to a negative pressure source via tubing 1604B such that fluid can flow toward the negative pressure source from the reservoir 1616 via a lumen defined by the outlet 1642. The sealing member 1630 can be configured to seal with a sealing surface 1622 of the valve seat 1620. The valve seat 1620 can define a through-hole 1624 and be disposed relative to the outlet 1642 such that fluid can flow from the reservoir 1616 to the outlet 1642 via the through-hole 1624 of the valve seat 1620.

The valve seat 1620 and the sealing member 1630 can be configured to allow liquid fluid to flow from the reservoir 1616 into the outlet 1642 when the liquid fluid level or volume within the reservoir 1616 is above a minimum threshold fluid level or volume, and to prevent the flow of fluid from the reservoir 1616 through the outlet 1642 when the liquid fluid level or volume within the reservoir 1616 is at or below a minimum threshold fluid level or volume, thus preventing air from flowing into the outlet 1642. For example, the sealing member 1630 can be configured to sealingly engage with the valve seat 1620 such that the sealing member 1630 obstructs the through-hole 1624. The valve seat 1620 and the sealing member 1630 can be configured to remain sealingly engaged such that the reservoir 1616 is fluidically isolated from the outlet 1642 after fluid has been added to the reservoir 1616 such that the fluid level is above the minimum threshold fluid level until the seal between the sealing member 1630 and the valve seat 1620 is manually disrupted via squeezing and deforming the housing 1610 and the valve seat 1620.

The cap 1650 can include a vent 1660 such that fluid, such as air, can exit the reservoir 1616 via the vent 1660. The assembly 1602 can also include a hydrophobic filter 1670 disposed between the reservoir 1616 and the vent 1660 such that liquid fluid that has been introduced into the reservoir 1616 via the inlet 1652 can be prevented from exiting the reservoir 1616 via the vent 1660. The hydrophobic filter 1670 can be, for example, an 0.2 micron mesh. The cap 1650 can also include an extending portion 1654 such that at least a portion of the cap 1650 extends laterally beyond a sidewall of the housing 1610 relative to a central axis of the housing 1610. The extending portion 1654 can be shaped similarly and function in use similarly to the extending portion 354 and the extending portion 1254 described above such that the central axis of the housing 1610 can be maintained at a minimum angle relative to horizontal when the extending portion 1654 and the second end 1614 are disposed in contact with a surface such that, when the fluid level within the reservoir decreases to a minimum threshold fluid level, the sealing member 1630 seals with the sealing surface 1622 prior to air flowing into the through-hole 1624 of the sealing member 1620. For example, in some embodiments, a portion of the extending portion 1654 can include a first contact point 1607 and a portion of the lower cap 1609 can include a second contact point 1609 such that, when the assembly 1602 is disposed on a surface (e.g., a horizontal surface), the first contact point 1607 and the second contact point 1609 both contact the surface and the central axis of the through-hole 1624 of the valve seat 1620 and the central axis of the housing 1610 is disposed at at least a minimum angle relative to the surface, and thus to the horizontal. For example, the first contact point 1607 on the extending portion 1654 can be located on a lower edge of the cap 1650 and the second contact point 1609 can be on a lower edge of the lower cap 1640 coupled to the housing 1610. The first contact point 1607, the second contact point 1609, and the central axis of the housing 1610 can lie in the same plane, and a line running through the first contact point 1607 and the second contact point 1609 can intersect the central axis of the housing 1610 at an angle corresponding to the angle of the central axis of the housing 1610 relative to a surface upon which the assembly 1602 can be disposed when the assembly 1602 is disposed on the surface.

As shown in FIG. 16A, in an exemplary embodiment, the housing 1610 can have an outer diameter D1 and an inner diameter D2. The outer diameter D1 can be, for example, about 0.995 inches and the inner diameter D2 can be, for example, about 0.875 inches. In some embodiments, the outer diameter D1 of the housing 1610 can be, for example, less than about 2 inches. In some embodiments, the outer diameter D1 can be greater than or equal to 0.6 inches. The housing 1610 can be sufficiently compliant such that a user can squeeze the housing 1610 to deform the valve seat 1620 and release the sealing member 1630.

The upper cap 1650, including the extending portion 1654, can have an outer diameter of D4. The outer diameter D4 can be, for example, about 2 inches. In some embodiments, the diameter D4 can be between about 1.25 inches and 2.75 inches.

The sealing member 1630 can be spherical and have an outer diameter D3. The outer diameter D3 can be, for example, about 15 mm. In some embodiments, the diameter D3 can be between about 10 mm and about 20 mm. In some embodiments, the ratio of the outer diameter D3 of the sealing member 1630 and the inner diameter D2 of the housing 1610 can be about 67%. In some embodiments, the ratio of the outer diameter D3 of the sealing member 1630 and the inner diameter D2 of the housing 1610 can be between about 50% and about 75%. The density of the sealing member 1630 can be about 0.55 g/cm$^3$.

The valve seat 1620 can have a height L1. The height L1 can be, for example, about 0.75 inches. In some embodiments, the height L1 can be greater than 0.3 inches. In some embodiments, the height L1 can be less than 1.3 inches. In the configuration in which the sealing member 1630 is sealingly engaged with the sealing surface 1622 of the valve seat 1620, the distance from the bottom of the valve seat 1620 to the center of the sealing member 1630 can be, for example, about 0.88 inches.

The upper surface of the valve seat 120 can have a thickness T3. The thickness T3 can be, for example, about 0.14 inches. In some embodiments, the thickness T3 can be, for example, less than about 0.14 inches.

The sealing surface 1622 can be arranged at an angle C1 relative to the central axis A1 of the housing 1610 and the through-hole 1624. The angle C1 can be, for example, 60°. In some embodiments, the angle C1 can be any suitable angle such that the sealing member 1630 is prevented from significantly bouncing off of the sealing surface 1622 and is continually guided toward the through-hole 1624.

As shown in FIG. 16B, the first contact point 1607 can be disposed a distance L3 farther laterally relative to the second contact point 1609 and the central axis A4. The first contact point 1607 can be disposed a distance L5 from the second contact point 1609 along the central axis A4. In some embodiments, the length L5 can be, for example, between about 3 inches and about 1 inch.

A line B passing through the first contact point 1607 and the second contact point 1609 can intersect the central axis A4 at an angle C2. The angle C2 can be, for example, about 8°. In some embodiments, the angle C2 can be greater than 8°. In some embodiments, the angle C2 can be greater than 0° to prevent the assembly 1602 from being inverted such that the sealing member 1630 may involuntarily seal with the valve seat 1620. In some embodiments, the angle C2 can be about 30°.

The lower cap 1640 can have an outer diameter D5. The outer diameter D5 can be any suitable diameter such that the second contact point 1609 is disposed relative to the first contact point 1607 such that the angle C2 is sufficiently large for the sealing member 1630 to seal with the sealing surface 1630 before the fluid level drops below a minimum threshold fluid level if the first contact point 1607 and the second contact point 1609 are disposed on horizontal surface. For example, the sealing surface 1622 can include a circular sealing interface 1623 with which the sealing member 1630 can engage to isolate the reservoir 1616 from the through-hole 1642. The outer diameter D5, the length L3, and the length L5 can each be any suitable length such that the sealing member 1630 sealingly engages with the sealing surface 1622 before the fluid level drops below the vertically highest portion of the sealing interface 1623. The location and size (e.g., diameter) of the sealing interface 1623 can depend on the diameter D3 of the sealing member 1630 and the angle C1 of the sealing surface 1622 to the central axis A4. The diameter of the sealing member 1630 can also be selected based, in part, on the inner diameter D2 of the housing 1610.

The minimum threshold fluid level can depend, in part, on the density of the sealing member 1630 relative to the liquid fluid in the reservoir 1610, the angle C1 of the sealing surface 1622 to the central axis A4, the length L3, and/or the length L5. The minimum threshold fluid level can also depend on the particular orientation of the assembly 1602.

In some embodiments, the outer diameter D4 can be about 2 inches, the outer diameter D1 can be about 0.94 inches, the outer diameter D3 can be 0.59 inches, the outer diameter D5 can be about 1.09 inches, and the length L5 can be about 2.95 inches.

In some embodiments, an assembly can include a spring assembly configured to apply a force to a sealing member. For example, FIG. 17 is a side view of an assembly 1702. The assembly 1702 can be the same or similar in structure and/or function to any of the assemblies described herein. For example, the assembly 1702 can include a housing 1710, an upper cap 1750, and a lower cap 1740. The assembly 1702 can also include a sealing member 1730 and a valve seat 1720 disposed within the housing 1710. The housing 1710 has a first end 1712 opposite the second end 1714 and defines a reservoir 1716. The upper cap 1750 defines an inlet 1752. The upper cap 1750 is sealingly coupled to the housing 1710 and the inlet 1752 can be fluidically coupled to a fluid source via tubing (e.g., a fluid source such as the fluid source 180 via tubing such as tubing 104A) such that fluid can be introduced into the reservoir 1716 via the inlet 1752. The lower cap 1740 can include an outlet 1742 and can be coupled to the second end 1714 of the housing 1710. The valve seat 1720 can be coupled to a barb of the lower cap 1740. The outlet 1742 can be fluidically coupled to a negative pressure source via tubing (e.g., a negative pressure source such as the negative pressure source 190 via tubing such as tubing 104B) such that fluid can flow toward the negative pressure source from the reservoir 1716 via a lumen defined by the outlet 1742. The valve seat 1720 can define a through-hole 1724 and be disposed relative to the outlet 1742 such that fluid can flow from the reservoir 1716 to the outlet 1742 via the through-hole 1724 of the valve seat 1720.

The sealing member 1730 can be configured to seal with a sealing surface 1722 of the valve seat 1720. The valve seat 1720 and the sealing member 1730 can be configured to allow liquid fluid to flow from the reservoir 1716 into the outlet 1742 when the liquid fluid level or volume within the reservoir 1716 is above a minimum threshold fluid level or volume, and to prevent the flow of fluid from the reservoir 1716 through the outlet 1742 when the liquid fluid level or volume within the reservoir 1716 is at or below a minimum threshold fluid level or volume, thus preventing air from flowing into the outlet 1742. For example, the sealing member 1730 can be configured to sealingly engage with the valve seat 1720 such that the sealing member 1730 obstructs the through-hole 1724. The valve seat 1720 and the sealing member 1730 can be configured to remain sealingly engaged such that the reservoir 1716 is fluidically isolated from the outlet 1742 after fluid has been added to the reservoir 1716 such that the fluid level is above the minimum threshold fluid level until the seal between the sealing member 1730 and the valve seat 1720 is manually disrupted via squeezing and deforming the housing 1710 and the valve seat 1720.

As shown in FIG. 17, the assembly 1702 can include a spring assembly 1785. The spring assembly 1785 can include a spring 1786, a first end element 1787, and a second end element 1788. The spring 1786 can have a first end coupled to the first end element 1787 and a second end coupled to the second end element 1788. The first end element 1787 and the second end element 1788 can each have any suitable shape, such as a disc-shape. The second end element 1788 can be configured to engage with the sealing member 1730 such that the spring 1786 can maintain the sealing member 1730 in sealing engagement with the valve seat 1720 when the fluid level is at or below the minimum threshold fluid level. The spring 1786 can be shaped and sized to apply a sufficient force to the sealing member 1730 such that the seal between the sealing member 1730 is maintained when the fluid level is at or below the minimum threshold fluid level, but the sealing member 1730 can float at the fluid level (and apply a force against the second end element 1788 to compress the spring 1786 toward the first end element 1787) when the fluid level is above the minimum threshold fluid level, i.e., when buoyant forces can overcome the opposing spring force.

The cap 1750 can include a vent 1760 such that fluid, such as air, can exit the reservoir 1716 via the vent 1760. The assembly 1702 can also include a hydrophobic filter 1770 disposed between the reservoir 1716 and the vent 1760 such that liquid fluid that has been introduced into the reservoir 1716 via the inlet 1752 can be prevented from exiting the reservoir 1716 via the vent 1760. The cap 1750 can also include an extending portion 1754 such that at least a portion of the cap 1750 extends laterally beyond a sidewall of the housing 1710 relative to a central axis of the housing 1710. The extending portion 1754 can be shaped similarly and function in use similarly to the extending portion 354 and the extending portion 1254 described above such that the central axis of the housing 1710 can be maintained at a minimum angle relative to horizontal when the extending portion 1754 and the second end 1714 are disposed in contact with a surface such that, when the fluid level within the reservoir decreases to a minimum threshold fluid level, the sealing member 1730 seals with the sealing surface 1722 prior to air flowing into the through-hole 1724 of the sealing member 1720.

Figure 18:
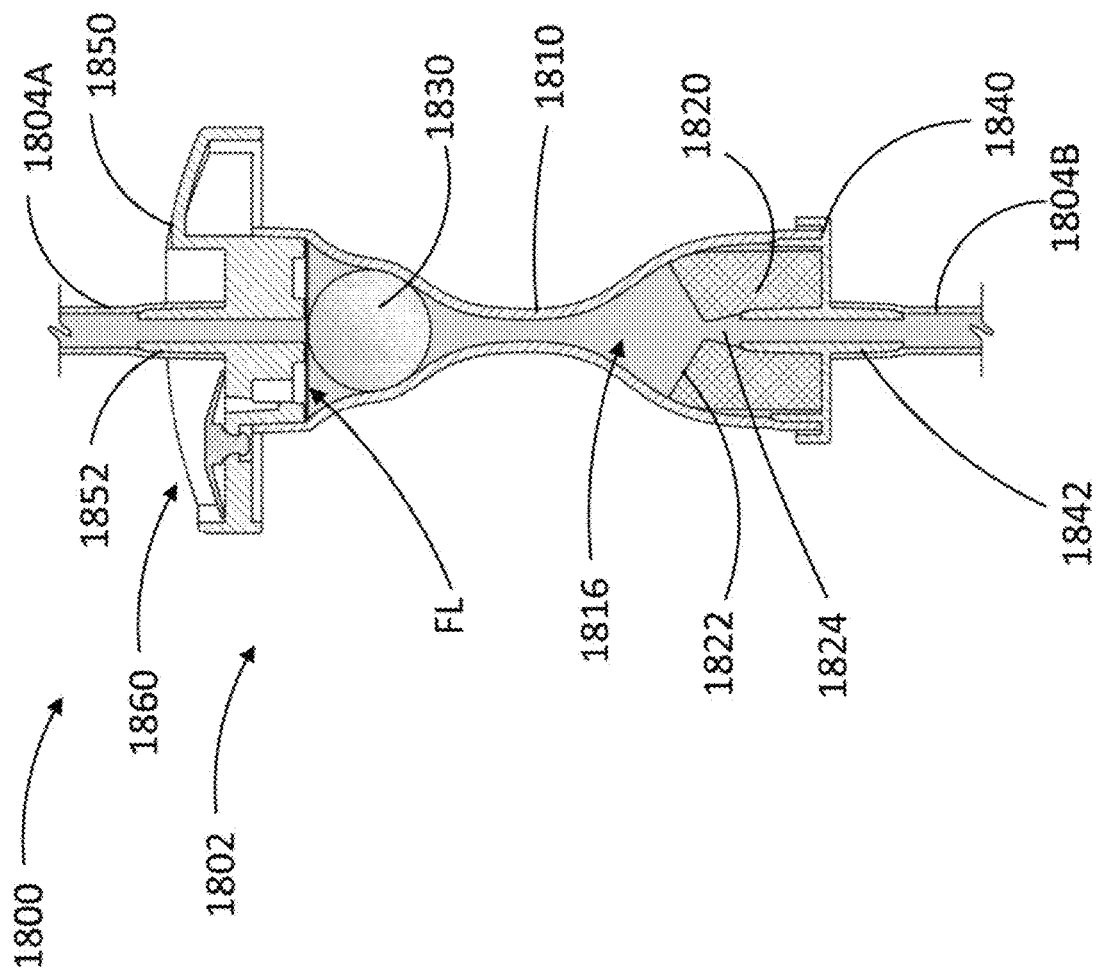
FIG. 18 is a side view of an assembly, according to an embodiment.

In some embodiments, a housing of an assembly may be sufficiently flexible such that the housing is susceptible to collapsing due to negative pressure applied to a reservoir defined by the housing. For example, FIG. 18 is a cross-sectional illustration of a system 1800 including an assembly 1802. The system 1800 can be the same or similar in structure and/or function to any of the systems described herein, such as the system 1500. The assembly 1802 can be the same or similar in structure and/or function to any of the assemblies described herein, such as the assembly 1502. For example, the assembly 1802 can include a housing 1810, an upper cap 1850, and a lower cap 1840. The assembly 1802 can also include a sealing member 1830 and a valve seat 1820 disposed within the housing 1810. The housing 1810 defines a reservoir 1816. The upper cap 1850 defines an inlet 1852. The upper cap 1850 is sealingly coupled to the housing 1810 and the inlet 1852 can be fluidically coupled to a fluid source via tubing 1804A (e.g., a fluid source such as the fluid source 180) such that fluid can be introduced into the reservoir 1816 via the inlet 1852. The lower cap 1840 can include an outlet 1842 and can be coupled to the bottom of the housing 1810. The valve seat 1820 can be coupled to a barb of the lower cap 1840. The outlet 1842 can be fluidically coupled to a negative pressure source via tubing 1804B such that fluid can flow toward the negative pressure source from the reservoir 1816 via a lumen defined by the outlet 1842. The sealing member 1830 can be configured to seal with a sealing surface 1822 of the valve seat 1820. The valve seat 1820 can define a through-hole 1824 and be disposed relative to the outlet 1842 such that fluid can flow from the reservoir 1816 to the outlet 1842 via the through-hole 1824 of the valve seat 1820. The cap 1850 can include a vent 1860 such that fluid, such as air, can exit the reservoir 1816 via the vent 1860. The assembly 1802 can also include a hydrophobic filter 1870 disposed between the reservoir 1816 and the vent 1860 such that liquid fluid that has been introduced into the reservoir 1816 via the inlet 1852 can be prevented from exiting the reservoir 1816 via the vent 1860. The cap 1850 can also include an extending portion 1854 such that at least a portion of the cap 1850 extends laterally beyond a sidewall of the housing 1810 relative to a central axis of the housing 1810. The extending portion 1854 can be shaped similarly and function in use similarly to the extending portion 354 and the extending portion 1254 described above such that the central axis of the housing 1810 can be maintained at a minimum angle relative to horizontal when the extending portion 1854 and the second end of the housing 1810 are disposed in contact with a surface such that, when the fluid level within the reservoir decreases to a minimum threshold fluid level, the sealing member 1830 seals with the sealing surface 1822 prior to air flowing into the through-hole 1824 of the sealing member 1820.

As shown in FIG. 18, in some embodiments, the housing 1810 may be sufficiently flexible or not sufficiently rigid such that the housing 1810 is susceptible to collapsing due to negative pressure applied to the reservoir 1816 defined by the housing 1810. The negative pressure source fluidically coupled to the reservoir 1816 via the tubing 1804B may draw fluid from the reservoir 1816 at such a rate that a negative gauge pressure may be created within the reservoir 1816 of sufficient magnitude to collapse the walls inward, preventing the sealing member 1830 from being able to reach and seal with the sealing surface 1822 of the valve seat 1820.

Figure 19:
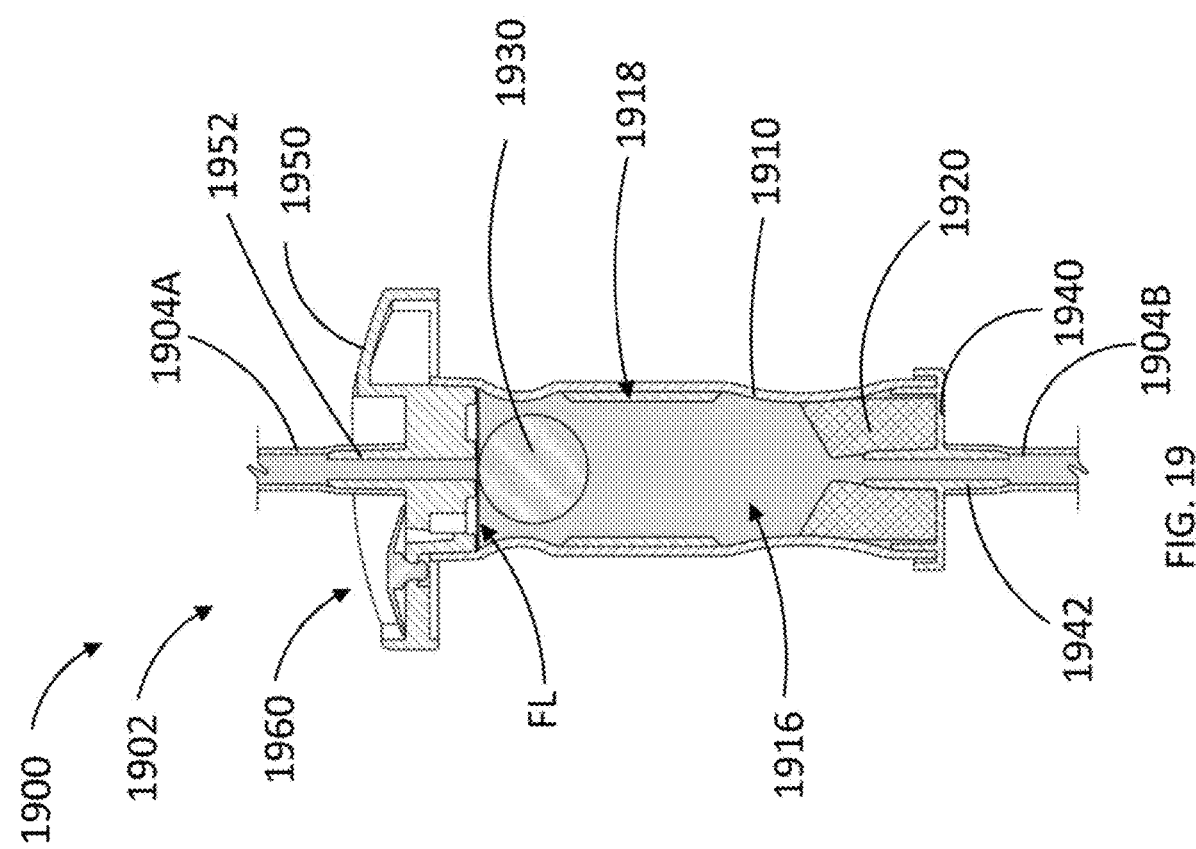
FIG. 19 is a side view of an assembly, according to an embodiment.

Therefore, in some embodiments, a housing may include a rigid support disposed between the valve seat and the upper cap sufficiently rigid to prevent the sidewalls of the housing from collapsing under the negative gauge pressure produced by the negative pressure source. For example, FIG. 19 is a cross-sectional illustration of a system 1900 including an assembly 1902. The system 1900 can be the same or similar in structure and/or function to any of the systems described herein, such as the system 1500. The assembly 1902 can be the same or similar in structure and/or function to any of the assemblies described herein, such as the assembly 1502. For example, the assembly 1902 can include a housing 1910, an upper cap 1950, and a lower cap 1940. The assembly 1902 can also include a sealing member 1930 and a valve seat 1920 disposed within the housing 1910. The housing 1910 defines a reservoir 1916. The upper cap 1950 defines an inlet 1952. The upper cap 1950 is sealingly coupled to the housing 1910 and the inlet 1952 can be fluidically coupled to a fluid source via tubing 1904A (e.g., a fluid source such as the fluid source 180) such that fluid can be introduced into the reservoir 1916 via the inlet 1952. The lower cap 1940 can include an outlet 1942 and can be coupled to the bottom of the housing 1910. The valve seat 1920 can be coupled to a barb of the lower cap 1940. The outlet 1942 can be fluidically coupled to a negative pressure source via tubing 1904B such that fluid can flow toward the negative pressure source from the reservoir 1916 via a lumen defined by the outlet 1942. The sealing member 1930 can be configured to seal with a sealing surface 1922 of the valve seat 1920. The valve seat 1920 can define a through-hole 1924 and be disposed relative to the outlet 1942 such that fluid can flow from the reservoir 1916 to the outlet 1942 via the through-hole 1924 of the valve seat 1920. The cap 1950 can include a vent 1960 such that fluid, such as air, can exit the reservoir 1916 via the vent 1960. The assembly 1902 can also include a hydrophobic filter 1970 disposed between the reservoir 1916 and the vent 1960 such that liquid fluid that has been introduced into the reservoir 1916 via the inlet 1952 can be prevented from exiting the reservoir 1916 via the vent 1960. The cap 1950 can also include an extending portion 1954 such that at least a portion of the cap 1950 extends laterally beyond a sidewall of the housing 1910 relative to a central axis of the housing 1910. The extending portion 1954 can be shaped similarly and function in use similarly to the extending portion 354 and the extending portion 1254 described above such that the central axis of the housing 1910 can be maintained at a minimum angle relative to horizontal when the extending portion 1954 and the second end of the assembly 1902 are disposed in contact with the surface such that, when the fluid level within the reservoir decreases to a minimum threshold fluid level, the sealing member 1930 seals with the sealing surface 1922 prior to air flowing into the through-hole 1924 of the sealing member 1920.

As shown in FIG. 19, the assembly 1920 includes a rigid support 1918 disposed between the valve seat 1920 and the upper cap 1950. The rigid support 1918 can be sufficiently rigid to prevent the sidewalls of the housing from collapsing under the negative gauge pressure produced by the negative pressure source. The rigid support 1918 can be formed as a tubular structure. The rigid support 1918 can have a length sufficiently small such that the rigid support does not obstruct the portion of the housing 1910 adjacent the valve member 1920 so that the rigid support 1918 does not prevent dislodgment of the sealing member 1930 from the valve seat 1920 via squeezing the housing 1910 and deforming the valve seat 1920.

In some embodiments, the rigid support 1918 is disposed on an inner surface of the housing 1910. In some embodiments, the rigid support 1918 is embedded within the sidewall of the housing 1910. In some embodiments, the rigid support 1918 is coupled on an outer surface of the housing 1910 via, for example, adhesive, so that the rigid support 1918 can prevent the portion of the housing 1910 coupled to the rigid support 1918 from shifting inward.

Figure 20:
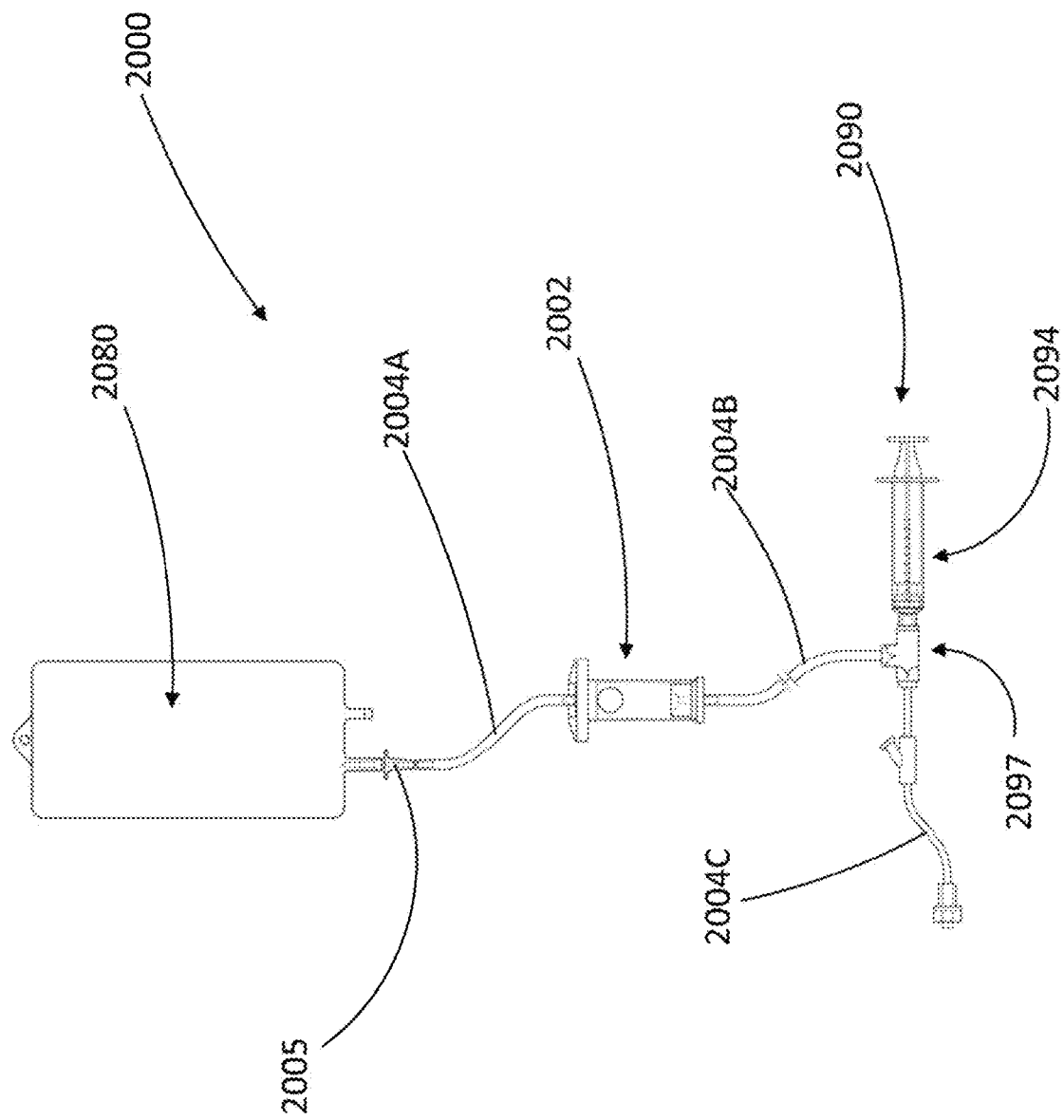
FIG. 20 is a schematic illustration of a system, according to an embodiment.

FIG. 20 is a schematic illustration of a system 2000. The system 2000 can be the same or similar in structure and/or function to any of the systems described herein, such as, for example, system 100. The system 2000 can include a fluid source 2080, an assembly 2002, and a negative pressure source 2090. The fluid source 2080 can be coupled to the assembly 2002 via a tubing 2004A. The tubing 2004A can include a fluid spike 2005 configured to engage with the fluid source 2080 such that the fluid source 2080 and the tubing 2004A are in fluidic communication. The assembly 2002 can be coupled to the negative pressure source 2090 via the tubing 2004B.

The fluid source 2080 can be, for example, saline fluid bag. The assembly 2002 can be the same or similar in structure and/or function to any of the assemblies described herein. The negative pressure source 2090 can include a dual check valve 2097 and a syringe 2094. An inlet of the dual check valve 2097 can be coupled to the tubing 2004B such that the syringe 2094 can be in fluidic communication with the assembly 2002 via the tubing 2004B and the dual check valve 2097. Tubing 2004C can be coupled to an outlet of the dual check valve 2097 such that the syringe 2094 can be in fluidic communication with a patient (e.g., the patient's vasculature system) via the dual check valve 2097 and the tubing 2004C.

Figure 21:
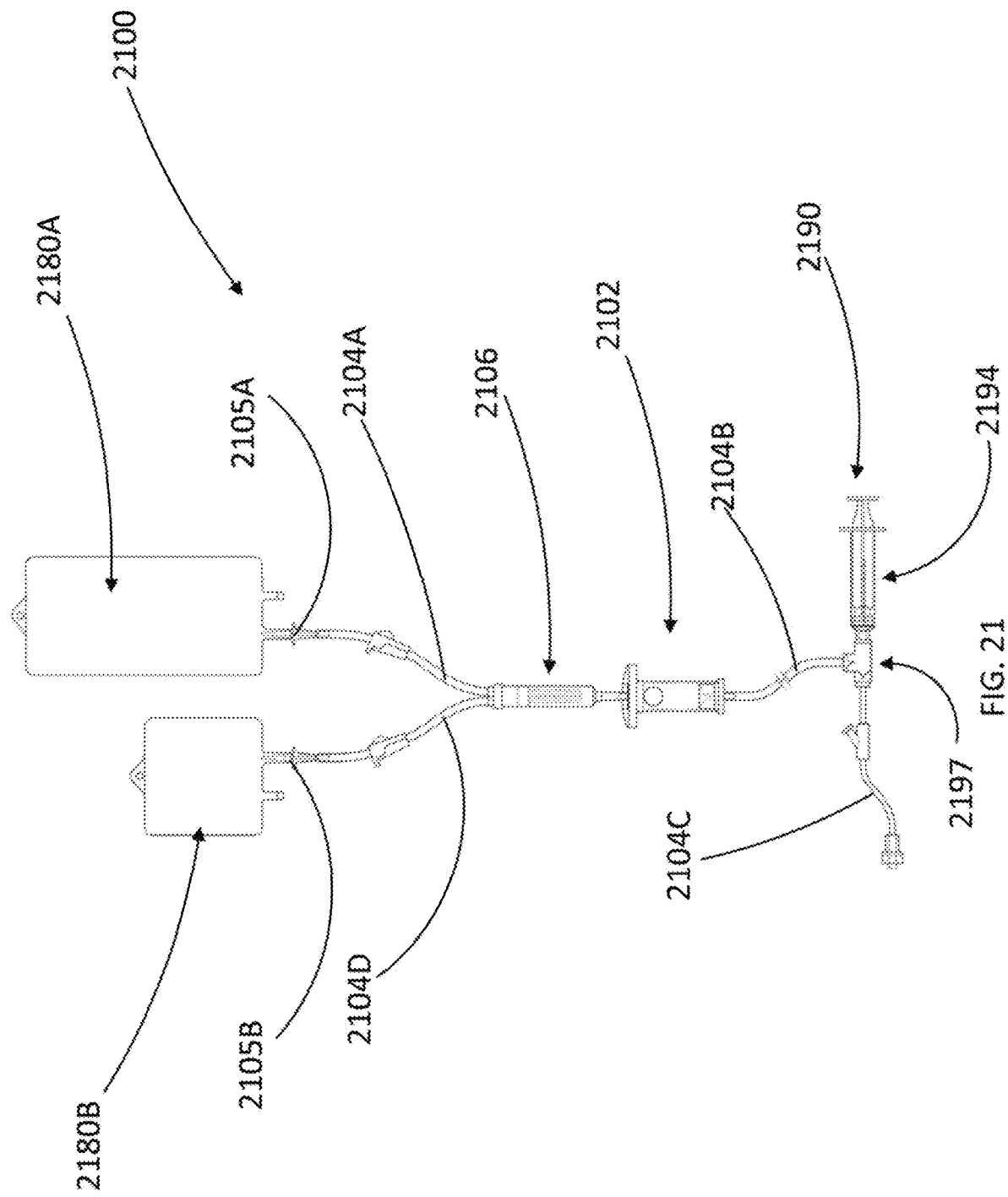
FIG. 21 is a schematic illustration of a system, according to an embodiment.

FIG. 21 is a schematic illustration of a system 2100. The system 2100 can be the same or similar in structure and/or function to any of the systems described herein, such as, for example, system 100. The system 2100 can include a first fluid source 2180A, a second fluid source 2180B, a blood filter 2106, an assembly 2102, and a negative pressure source 2190. The first fluid source 2180A can be coupled to the blood filter 2106 via a tubing 2104A. The tubing 2104A can include a first fluid spike 2105A configured to engage with the first fluid source 2180A such that the first fluid source 2180A and the tubing 2104A are in fluidic communication. The second fluid source 2180B can be coupled to the blood filter 2106 via a tubing 2104D. The tubing 2104D can include a second fluid spike 2105B configured to engage with the second fluid source 2180B such that the second fluid source 2180B and the tubing 2104D are in fluidic communication. The blood filter 2106 can be in fluidic communication with the assembly 2102. In some embodiments, the blood filter 2106 can be directly coupled to the assembly 2102. In some embodiments, the blood filter 2106 can be coupled to the assembly 2102 via tubing. The assembly 2102 can be coupled to the negative pressure source 2190 via the tubing 2104B.

The first fluid source 2180A can be, for example, a fluid bag containing saline. The second fluid source 2180B can be, for example, a fluid bag containing blood. The blood filter 2106 can include a filter housing and any suitable filter (e.g., a macrofilter) configured to filter precipitated or coagulated particles from blood prior to infusion into a patient. The assembly 2102 can be the same or similar in structure and/or function to any of the assemblies described herein. The negative pressure source 2190 can include a dual check valve 2197 and a syringe 2194. An inlet of the dual check valve 2197 can be coupled to the tubing 2104B such that the syringe 2194 can be in fluidic communication with the assembly 2102 via the tubing 2104B and the dual check valve 2197. Tubing 2104C can be coupled to an outlet of the dual check valve 2197 such that the syringe 2194 can be in fluidic communication with a patient (e.g., the patient's vasculature system) via the dual check valve 2197 and the tubing 2104C.

Although not shown, in some configurations, rather than having one assembly (e.g., assembly 2102) coupled to two fluid sources (e.g., the first fluid source 2180A and the second fluid source 2180B), each fluid source can be coupled to an individual assembly. For example a first assembly 2102 can be coupled to the first fluid source 2180A and a second assembly 2102 can be coupled to the second fluid source 2180B.

Figure 22:
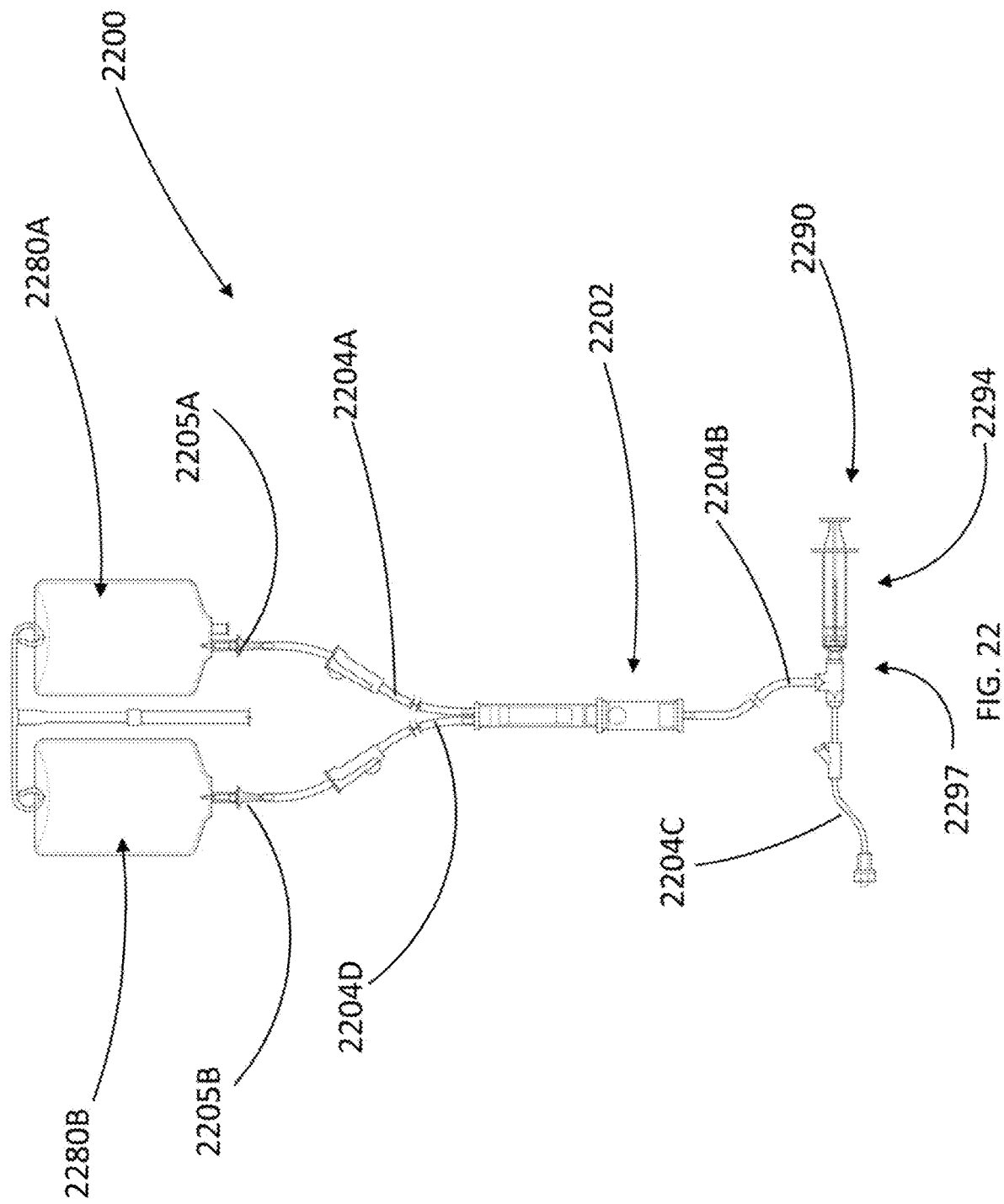
FIG. 22 is a schematic illustration of a system, according to an embodiment.

In some embodiments, rather than coupling an assembly to a blood filter, an assembly such as any of the assemblies described herein can include a blood filter. For example, FIG. 22 shows a system 2200. The system 2200 can be similar in structure and/or function to any of the systems described herein, such as, for example, system 100 and/or system 2100. The system 2200 can include a first fluid source 2280A, a second fluid source 2280B, an assembly 2202, and a negative pressure source 2290. The first fluid source 2280A can be coupled to the assembly 2202 via a tubing 2204A. The tubing 2204A can include a first fluid spike 2205A configured to engage with the first fluid source 2280A such that the first fluid source 2280A and the tubing 2204A are in fluidic communication. The second fluid source 2280B can be coupled to the assembly 2202 via a tubing 2204D. The tubing 2204D can include a second fluid spike 2205B configured to engage with the second fluid source 2280B such that the second fluid source 2280B and the tubing 2204D are in fluidic communication. The assembly 2202 can be coupled to the negative pressure source 2290 via the tubing 2204B.

Figure 23:
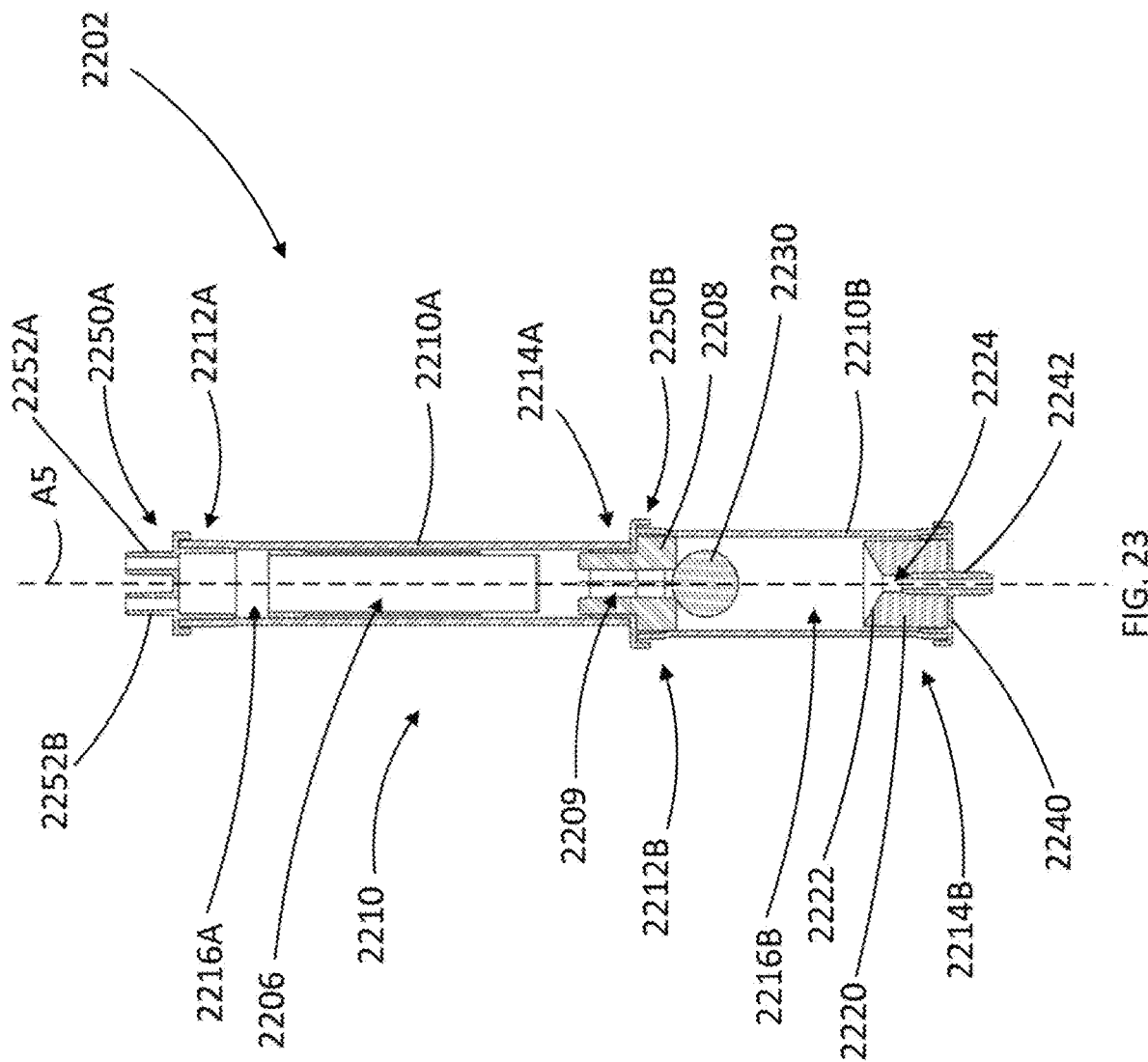
FIG. 23 is a cross-sectional view of an assembly, according to an embodiment.

The assembly 2202 can be similar in structure and/or function to any of the assemblies described herein and can include a blood filter 2206. For example, FIG. 23 shows a cross-sectional illustration of the assembly 2202. The assembly 2202 can include a housing 2210, an upper cap 2250A (also referred to herein as a third cap), and a lower cap 2240 (also referred to herein as a second cap). The housing 2210 can include a first housing portion 2210A, an intermediate cap 2250B (also referred to herein as a first cap), and a second housing portion 2210B. The first housing portion 2210A and the second housing portion 2210B can be coaxial along a central axis A5. The assembly 2202 can also include a sealing member 2230 and a valve seat 2220 disposed within the housing 2210. The assembly 2202 can also include a retention member 2208 that defines a through-hole 2209. In some embodiments, the retention member 2208 can be included in or coupled to the intermediate cap 2250B. In some embodiments, the retention member 2208 and the intermediate cap 2250B can be integrally formed as a one-piece monolithic structure.

The first housing portion 2210A has a first end 2212A opposite a second end 2214A and defines a first reservoir 2216A. The blood filter 2206 can be disposed within the first reservoir 2216A. The second housing portion 2210B has a first end 2212B opposite a second end 2214B and defines a second reservoir 2216B. The sealing member 2230 and the valve seat 2220 can be disposed within the second reservoir 2216B. The upper cap 2250A defines a first inlet 2252A and a second inlet 2252B. The upper cap 2250A is sealingly coupled to the first end 2212A of the first housing portion 2210A and the first inlet 2252A and the second inlet 2252B can be fluidically coupled to the first fluid source 2280A and the second fluid source 2280B via tubing 2204A and tubing 2204D, respectively, such that fluid can be introduced into the first reservoir 2216A via the first inlet 2252A and the second inlet 2252B. The second end 2214A of the first housing portion 2210A can be coupled to a first surface of the intermediate cap 2250B and the first end 2214B of the second housing portion 2210B can be coupled to a second surface of the intermediate cap 2250B. In some embodiments, the second surface can be opposite the first surface. The lower cap 2240 can include an outlet 2242 and can be sealingly coupled to the second end 2214B of the second housing portion 2210B. The valve seat 2220 can be coupled to a barb of the lower cap 2240. The outlet 2242 can be fluidically coupled to the negative pressure source 2290 via the tubing 2204B shown in FIG. 21 such that fluid can flow toward the negative pressure source 2290 from the second reservoir 2216B via a lumen defined by the outlet 2242. The sealing member 2230 can be configured to seal with a sealing surface 2222 of the valve seat 2220. The valve seat 2220 can define a through-hole 2224 and be disposed relative to the outlet 2242 such that fluid can flow from the second reservoir 2216B to the outlet 2242 via the through-hole 2224 of the valve seat 2220.

The first reservoir 2216A and the second reservoir 2216B can be in fluidic communication such that fluid that flows into the first reservoir 2216A via the first inlet 2252A and/or the second inlet 2252B can flow into the second reservoir. The retention member 2208 can be coupled to the intermediate cap 2250B and can be configured to obstruct the sealing member 2230 from traveling from the second reservoir 2216B to the first reservoir 2216A (e.g., in the event the fluid level in the housing 2210 rises above the level of the intermediate cap 2250B). For example, the retention member 2208 can include ribs that project toward the central axis A5 (e.g., towards the central axis of the through-hole 2209) and reduce the width of the through-hole 2209 in one, two, or more directions.

The first fluid source 2280A can be, for example, a fluid bag containing saline. The second fluid source 2280B can be, for example, a fluid bag containing blood. The blood filter 2206 can be any suitable filter (e.g., a macrofilter) configured to filter precipitated or coagulated particles from blood prior to infusion into a patient. The negative pressure source 2290 can include a dual check valve 2297 and a syringe 2294. An inlet of the dual check valve 2297 can be coupled to the tubing 2204B such that the syringe 2294 can be in fluidic communication with the assembly 2202 via the tubing 2204B and the dual check valve 2297. Tubing 2204C can be coupled to an outlet of the dual check valve 2297 such that the syringe 2294 can be in fluidic communication with a patient (e.g., the patient's vasculature system) via the dual check valve 2297 and the tubing 2204C.

As shown in FIGS. 22 and 23, the assembly 2202 can be formed without an air vent. The second housing portion 2210B can be formed of a deformable material such that, in use, a user can deform (e.g., squeeze) the second housing portion 2210B to reduce the volume of the reservoir 2216B and force air out of the assembly 2202 and into the first fluid source 2280A and/or the second fluid source 2280B via the first reservoir 2216A and the first inlet 2252A and/or the second inlet 2252B. For example, in a configuration in which the sealing member 2230 is sealed with the valve seat 2220, liquid fluid can be introduced into the first reservoir 2216A and the second reservoir 2216B such that a fluid level within the second reservoir 2216B rises. Any air trapped in the second reservoir 2216B can be pushed out of the second reservoir 2216B and through the through-hole 2209 of the retention member 2208 via squeezing opposite sidewall portions of the second housing portion 2210B toward each other such that the volume of the second reservoir 2216B decreases and the air travels out of the second reservoir 2216B.

Although the housing 2210 is shown as including separate components coupled together, in some embodiments, any suitable components of the housing 2210 can be formed as a unitary structure. For example, the first housing portion 2210A and the intermediate cap 2250B can be monolithically formed, the second housing portion 2210B and the intermediate cap 2250B can be monolithically formed, or the first housing portion 2210A, the second housing portion 2210B, and the intermediate cap 2250B can be monolithically formed.

Figure 25:
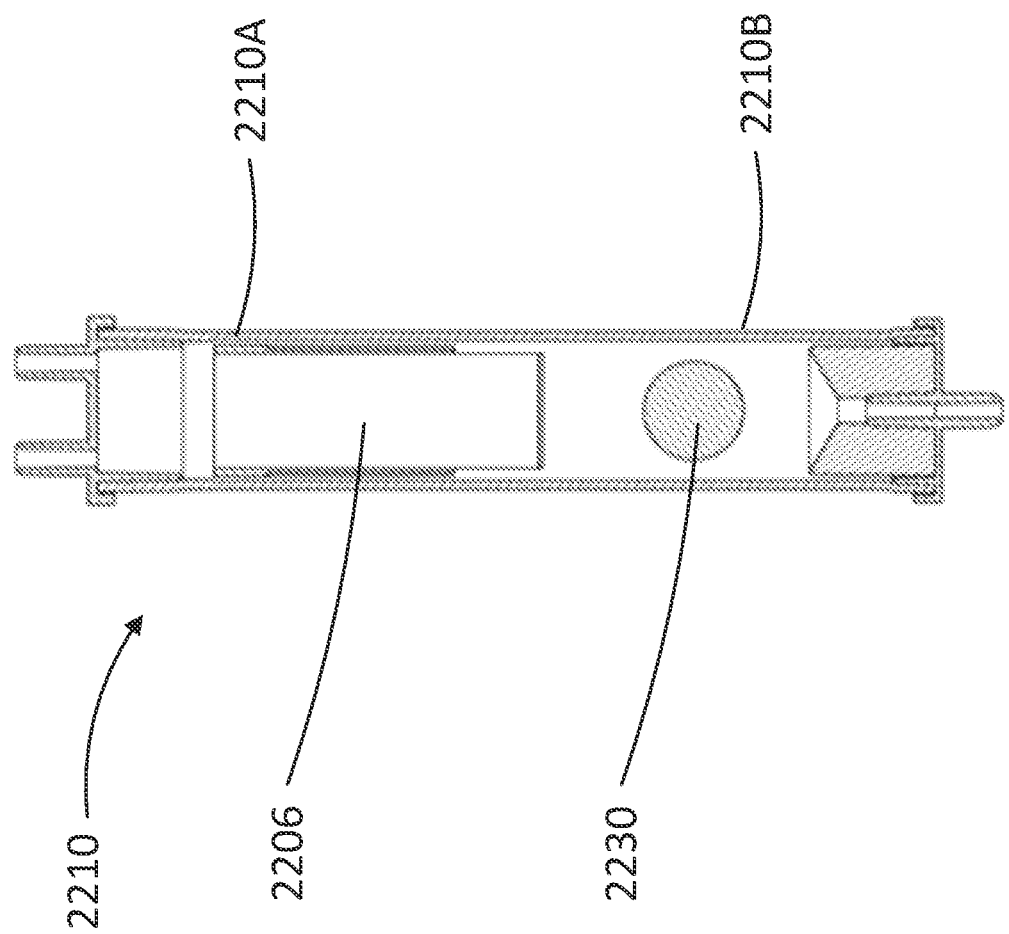
FIG. 25 is a schematic illustration of a system, according to an embodiment.

Although the first housing portion 2210A is shown has having a smaller diameter (e.g., inner and/or outer diameter) than the diameter (e.g., inner and/or outer diameter) of the second housing portion 2210B, in some embodiments, such as is shown in FIG. 25, the first housing portion 2210A of the housing 2210 can have a diameter (e.g., inner and/or outer diameter) that is substantially equal to or greater than the diameter (e.g., inner and/or outer diameter) of the second housing portion 2210B. As shown in FIG. 25, in some embodiments, the first housing portion 2210A and the second housing portion 2210B can have substantially equal diameters and can be coupled directly to each other without the need for the intermediate cap 2250B and/or retention member 2208. For example, the first housing portion 2210A and the second housing portion 2210B can be formed as a unitary structure. For example, as shown in FIG. 25, the first housing portion 2210A and the second housing portion 2210B can form a single tube and the first reservoir 2316A and the second reservoir 2316B can collectively define a cylindrical reservoir. Rather than an upper limit of travel of the sealing member 2230 being defined by the retention member 2208, a bottom end of the blood filter 2206 can define the upper limit of travel of the sealing member 2230. In some embodiments, the first housing portion 2210A and the second housing portion 2210B can be coupled to each other via the intermediate cap 2250B, but the assembly 2202 can include no retention member between the first reservoir 2216A and the second reservoir 2216B such that the blood filter 2206 can define the upper limit of travel of the sealing member 2230.

Figure 24:
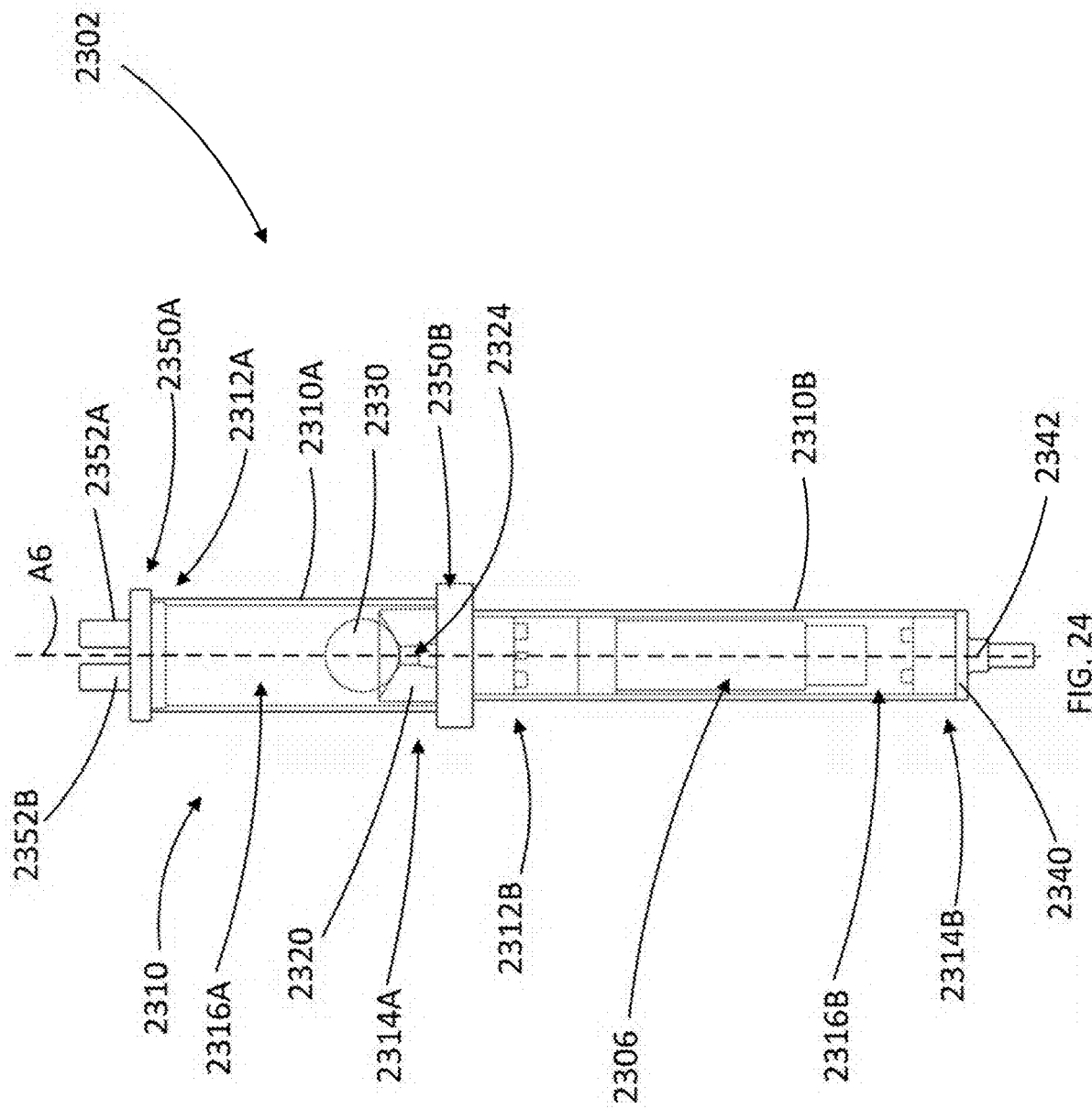
FIG. 24 is a front view of an assembly, according to an embodiment.

In some embodiments, rather than including a blood filter upstream of a sealing member and valve seat, the blood filter can be coupled to an outlet of an assembly and/or included downstream of the sealing member and valve seat. For example, FIG. 24 shows a front view of an assembly 2302. The assembly 2302 can be similar in structure and/or function to any of the assemblies described herein, such as the assembly 2202. Additionally, the assembly 2302 can be included in a system similar to any of the systems described herein, such as the system 2200 as a substitute for the assembly 2202.

The assembly 2302 can include a blood filter 2306. The blood filter 2306 can be any suitable filter (e.g., a macrofilter) configured to filter precipitated or coagulated particles from blood prior to infusion into a patient. The assembly 2302 can include a housing 2310, an upper cap 2350A (also referred to herein as a first cap), and a lower cap 2340 (also referred to herein as a second cap). The housing 2310 can include a first housing portion 2310A, an intermediate cap 2350B (also referred to herein as a third cap), and a second housing portion 2310B. The first housing portion 2310A and the second housing portion 2310B can be coaxial along a central axis A6. The assembly 2302 can also include a sealing member 2330 and a valve seat 2320 disposed within the housing 2310.

The first housing portion 2310A has a first end 2312A opposite a second end 2314A and defines a first reservoir 2316A. The sealing member 2330 and the valve seat 2320 can be disposed within the first reservoir 2316A. The second housing portion 2310B has a first end 2312B opposite a second end 2314B and defines a second reservoir 2316B. The blood filter 2306 can be disposed within the second reservoir 2316B. The upper cap 2350A defines a first inlet 2352A and a second inlet 2352B. The upper cap 2350A is sealingly coupled to the first end 2312A of the first housing portion 2310A and the first inlet 2352A and the second inlet 2352B can be fluidically coupled to a first fluid source and a second fluid source via tubing such that fluid can be introduced into the first reservoir 2316A via the first inlet 2352A and the second inlet 2352B. The second end 2314A of the first housing portion 2310A can be coupled to a first surface of the intermediate cap 2350B and the first end 2314B of the second housing portion 2310B can be coupled to a second surface of the intermediate cap 2350B. In some embodiments, the second surface can be opposite the first surface. The valve seat 2320 can be coupled to a barb of the intermediate cap 2350B. The sealing member 2330 can be configured to seal with a sealing surface 2322 of the valve seat 2320. The valve seat 2320 can define a through-hole 2324 and be disposed relative to an inlet of the intermediate cap 2350B such that fluid can flow from the first reservoir 2316A to the second reservoir 2316B via the through-hole 2324 of the valve seat 2320. The lower cap 2340 can include an outlet 2342 and can be sealingly coupled to the second end 2314B of the second housing portion 2310B. The outlet 2342 can be fluidically coupled to a negative pressure source via tubing such that fluid can flow toward the negative pressure source from the second reservoir 2316B via a lumen defined by the outlet 2342.

As shown in FIG. 24, the assembly 2302 can be formed without an air vent. The first housing portion 2310A can be formed of a deformable material such that, in use, a user can deform (e.g., squeeze) the first housing portion 2310A to reduce the volume of the first reservoir 2316A and force air out of the assembly 2302 via the first inlet 2352A and/or the second inlet 2352B. For example, in a configuration in which the sealing member 2330 is sealed with the valve seat 2320, liquid fluid can be introduced into the first reservoir 2316A such that a fluid level within the first reservoir 2316A rises. Any air trapped in the first reservoir 2316A can be pushed out of the first reservoir 2316A via squeezing opposite sidewall portions of the first housing portion 2310A toward each other such that the volume of the first reservoir 2316A decreases and the air travels out of the first reservoir 2316A.

Although the first housing portion 2310A is shown has having a smaller diameter (e.g., inner and/or outer diameter) than the diameter (e.g., inner and/or outer diameter) of the second housing portion 2310B, in some embodiments, the first housing portion 2310A can have a diameter (e.g., inner and/or outer diameter) that is substantially equal to or greater than the diameter (e.g., inner and/or outer diameter) of the second housing portion 2310B. Although the housing 2310 is shown as including separate components coupled together, in some embodiments, any suitable components of the housing 2310 can be formed as a unitary structure. For example, the first housing portion 2310A and the intermediate cap 2350B can be monolithically formed, the second housing portion 2310B and the intermediate cap 2350B can be monolithically formed, or the first housing portion 2310A, the second housing portion 2310B, and the intermediate cap 2350B can be monolithically formed.

While various embodiments have been described above, it should be understood that they have been presented by way of example only, and not limitation. For example, although various embodiments described herein include a negative pressure source and/or the application of negative pressure on an assembly by a negative pressure source, in some embodiments, the systems and/or apparatus described herein can be used without applying a negative pressure source such that fluid flows under gravitational forces through the systems and/or apparatus. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. An apparatus, comprising:
a first housing portion having a first end, a second end, and defining a first reservoir portion;
a second housing portion having a first end, a second end, and a sidewall extending between the first end and the second end of the housing portion and having an inner surface defining a second reservoir portion, the sidewall configured to be deformed between an undeformed and a deformed configuration, the first end of the second housing portion coupled to the second end of the first housing portion;
an upper cap coupled to the first end of the first housing portion and defining an inlet;
a lower cap defining an outlet, the lower cap coupled to the second end of the second housing portion;
a filter disposed within the first reservoir portion;
a valve seat having a first end, a second end, an outer surface extending between the first end and the second end, and a sealing surface, the valve seat being deformable, the valve seat defining a through-hole from the first end to the second end, the second end of the valve seat coupled to the lower cap such that the through-hole is in fluid communication with the outlet of the lower cap, the valve seat disposed within the second housing portion such that the outer surface is surrounded by the inner surface of the second housing portion, the valve seat being formed of a first material and the second housing portion being formed of a second material different from the first material; and
a sealing member configured to float at a liquid fluid level within the second reservoir portion and to seal with the sealing surface of the valve seat prior to the liquid fluid level within the second reservoir portion decreasing below a minimum threshold fluid level, the sealing member configured to transition from a sealed configuration in which the sealing member is engaged with the sealing surface to an unsealed configuration in which the sealing member floats at the liquid fluid level when the liquid fluid level is above the minimum threshold fluid level in response to the sidewall of the second housing portion being flexed to the deformed configuration to contact and deform the valve seat to disrupt a seal between the sealing member and the sealing surface.

2. The apparatus of claim 1, wherein the first housing portion has a first diameter and the second housing portion has a second diameter the same as the first diameter.

3. The apparatus of claim 1, wherein the first end of the second housing portion is directly coupled to the second end of the first housing portion.

4. The apparatus of claim 1, wherein the first housing portion and the second housing portion form a tube and the first reservoir portion and the second reservoir portion collectively form a cylindrical reservoir.

5. The apparatus of claim 1, wherein a bottom end of the filter defines an upper limit of travel of the sealing member.

6. The apparatus of claim 1, wherein the inlet of the upper cap is a first inlet, the upper cap defining a second inlet, the first inlet and the second inlet in fluid communication with the first reservoir portion.

7. The apparatus of claim 1, wherein the sealing member and the sealing surface form a circular sealing interface, and the minimum threshold fluid level is disposed within a horizontal plane corresponding to the highest vertical portion of the circular sealing interface.

8. The apparatus of claim 1, further comprising a negative pressure source fluidically coupled to the outlet, the apparatus configured such that, when the sealing member is in the sealed configuration, the negative pressure source maintains a force on the sealing member to maintain the sealing member in the sealed configuration when the fluid level is above the minimum threshold fluid level, the valve seat is undeformed, and the sidewall is in the undeformed configuration.

9. The apparatus of claim 1, wherein the second material has a higher durometer than the first material.

10. The apparatus of claim 9, wherein the first material is silicone and the second material is polyvinyl chloride.

11. The apparatus of claim 1, wherein the valve seat has an outer diameter smaller than an inner diameter of the second housing portion such that a circumferential gap is defined between the inner surface of the second housing portion and the outer surface of the valve seat.

12. An apparatus, comprising:
a first housing portion having a first end, a second end, and defining a first reservoir;
a second housing portion having a first end, a second end, and a cylindrical sidewall extending between the first end and the second end of the second housing portion and having an inner surface defining a second reservoir, the cylindrical sidewall configured to be deformed between an undeformed and a deformed configuration, the cylindrical sidewall having a constant thickness between the first end and the second end of the second housing portion in the undeformed configuration;
an upper cap coupled to the first end of the first housing portion and defining an inlet;
an intermediate cap defining a through-hole, the intermediate cap coupled the second end of the first housing portion and to the first end of the second housing portion such that the first reservoir is in fluid communication with the second reservoir via the through-hole;
a lower cap defining an outlet, the lower cap coupled to the second end of the second housing portion;
a filter disposed within the first reservoir;
a valve seat having a first end, a second end, an outer surface extending between the first end and the second end, and a sealing surface, the valve seat being deformable, the valve seat defining a through-hole from the first end to the second end, the second end coupled to the lower cap such that the through-hole is in fluid communication with the outlet of the lower cap, the valve seat disposed within the second housing portion such that the outer surface is surrounded by the inner surface of the second housing portion, the valve seat having an outer diameter smaller than an inner diameter of the second housing portion such that a circumferential gap is defined between the inner surface of the second housing portion and the outer surface of the valve seat, the circumferential gap bounded on a lower end by the lower cap, the valve seat being formed of a first material and the second housing portion being formed of a second material different from the first material; and
a sealing member configured to float at a liquid fluid level within the second reservoir and to seal with the sealing surface of the valve seat prior to the liquid fluid level within the second reservoir decreasing below a minimum threshold fluid level, the sealing member configured to transition from a sealed configuration in which the sealing member is engaged with the sealing surface to an unsealed configuration in which the sealing member floats at the liquid fluid level when the liquid fluid level is above the minimum threshold fluid level in response to the cylindrical sidewall of the second housing portion being flexed to the deformed configuration to contact and deform the valve seat to disrupt a seal between the sealing member and the sealing surface.

13. The apparatus of claim 12, wherein the sealing member and the sealing surface form a circular sealing interface, and the minimum threshold fluid level is disposed within a horizontal plane corresponding to the highest vertical portion of the circular sealing interface.

14. The apparatus of claim 12, wherein the filter is a blood filter.

15. The apparatus of claim 12, further comprising a negative pressure source fluidically coupled to the outlet, the apparatus configured such that, when the sealing member is in the sealed configuration, the negative pressure source maintains a force on the sealing member to maintain the sealing member in the sealed configuration when the fluid level is above the minimum threshold fluid level, the valve seat is undeformed, and the cylindrical sidewall is in the undeformed configuration.

16. The apparatus of claim 12, wherein the inlet of the upper cap is a first inlet, the upper cap defining a second inlet, the first inlet and the second inlet in fluid communication with the first reservoir.

17. The apparatus of claim 12, wherein the intermediate cap includes a retention portion that is configured to prevent the sealing member from floating from the second reservoir into the first reservoir.

18. The apparatus of claim 17, wherein the retention portion includes ribs projecting inward from a sidewall portion of the retention portion defining the through-hole of the intermediate cap toward a central axis of the through-hole of the intermediate cap.

19. The apparatus of claim 12, wherein the intermediate cap is coupled to a retention member that is configured to prevent the sealing member from floating from the second reservoir into the first reservoir.

20. The apparatus of claim 12, wherein the first housing portion and/or the second housing portion are monolithically formed with the intermediate cap.

21. An apparatus, comprising:
a first housing portion having a first end, a second end, and defining a first reservoir;
a second housing portion having a first end, a second end, and defining a second reservoir;
an upper cap defining an inlet, the upper cap coupled to the first end of the first housing portion;
an intermediate cap defining a through-hole, the intermediate cap coupled to the second end of the first housing portion and to the first end of the second housing portion such that the first reservoir is in fluid communication with the second reservoir via the through-hole;
a lower cap defining an outlet, the lower cap coupled to the second end of the second housing portion;
a filter disposed within the second reservoir;
a valve seat having a first end, a second end, and a sealing surface, the valve seat defining a through-hole from the first end to the second end, the second end coupled to the intermediate cap such that the through-hole of the valve seat is in fluid communication with the through-hole of the intermediate cap; and a sealing member configured to float at a liquid fluid level within the first reservoir and to seal with the sealing surface of the valve seat prior to the liquid fluid level within the first reservoir decreasing below a minimum threshold fluid level, the sealing member configured to transition from a sealed configuration in which the sealing member is engaged with the sealing surface to an unsealed configuration in which the sealing member floats at the liquid fluid level when the liquid fluid level is above the minimum threshold fluid level.

22. The apparatus of claim 21, wherein the sealing member and the sealing surface form a circular sealing interface, and the minimum threshold fluid level is disposed within a horizontal plane corresponding to the highest vertical portion of the circular sealing interface.

23. The apparatus of claim 21, wherein the filter is a blood filter.

24. The apparatus of claim 21, wherein the valve seat is deformable, the first housing portion including a cylindrical sidewall defining the first reservoir, the cylindrical sidewall is configured to be deformed between an undeformed and a deformed configuration, and the sealing member is configured to transition from a sealed configuration in which the seal is engaged with the sealing surface to an unsealed configuration in which the sealing member floats at the liquid fluid level when the liquid fluid level is above the minimum threshold fluid level and the cylindrical sidewall is flexed to the deformed configuration such that the valve seat is deformed and a seal between the sealing member and the sealing surface is disrupted.

25. The apparatus of claim 24, further comprising a negative pressure source fluidically coupled to the outlet such that, when the sealing member is in the sealed configuration, the negative pressure source maintains a force on the sealing member to maintain the sealing member in the sealed configuration when fluid is introduced to the first reservoir via the inlet of the upper cap such that the fluid level is above the minimum threshold fluid level and the cylindrical sidewall is in the undeformed configuration.

26. The apparatus of claim 21, wherein the inlet of the upper cap is a first inlet, the upper cap defining a second inlet, the first inlet and the second inlet in fluid communication with the first reservoir.

27. The apparatus of claim 21, wherein the first housing portion and/or the second housing portion are monolithically formed with the intermediate cap.

* * * * *